(12) United States Patent
Kuwabara et al.

(10) Patent No.: US 8,313,671 B2
(45) Date of Patent: Nov. 20, 2012

(54) HETEROCYCLIC COMPOUND AND USE THEREOF

(75) Inventors: Hirokazu Kuwabara, Tokyo (JP); Masaaki Ikeda, Tokyo (JP); Kazuo Takimiya, Hiroshima (JP)

(73) Assignees: Hiroshima University, Hiroshima (JP); Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/126,771

(22) PCT Filed: Nov. 20, 2009

(86) PCT No.: PCT/JP2009/069688
§ 371 (c)(1),
(2), (4) Date: Apr. 29, 2011

(87) PCT Pub. No.: WO2010/058833
PCT Pub. Date: May 27, 2010

(65) Prior Publication Data
US 2011/0204295 A1    Aug. 25, 2011

(30) Foreign Application Priority Data

Nov. 21, 2008 (JP) .................. 2008-298805
Mar. 12, 2009 (JP) .................. 2009-059980

(51) Int. Cl.
*C09K 19/34* (2006.01)
*H01B 1/12* (2006.01)
*C07D 495/14* (2006.01)
*C07D 209/86* (2006.01)

(52) U.S. Cl. .................. 252/299.61; 252/500; 548/445; 549/42

(58) Field of Classification Search .................. None
See application file for complete search history.

(56) References Cited

U.S. PATENT DOCUMENTS

| | | |
|---|---|---|
| 3,663,568 A | 5/1972 | Roos et al. |
| 5,370,820 A | 12/1994 | Boden et al. |
| 2009/0001357 A1 | 1/2009 | Takimiya et al. |
| 2009/0065770 A1 | 3/2009 | Miura et al. |
| 2010/0137617 A1 | 6/2010 | Kuwabara et al. |

FOREIGN PATENT DOCUMENTS

| | | |
|---|---|---|
| EP | 0364185 A2 | 4/1990 |
| EP | 1847544 A1 | 10/2007 |
| EP | 2006291 A1 | 12/2008 |
| FR | 2028476 A1 | 10/1970 |
| GB | 1259563 A | 1/1972 |
| JP | 2-208391 A | 8/1990 |
| JP | 7-306317 A | 11/1995 |
| JP | 2001-196182 A | 7/2001 |
| JP | 2003-13054 A | 1/2003 |
| JP | 2005-156822 A | 6/2005 |
| JP | 2006-89413 A | 4/2006 |
| JP | 2007-269775 A | 10/2007 |
| JP | 2008-147256 A | 6/2008 |
| JP | 2008-258592 A | 10/2008 |
| WO | 2006/077888 A | 7/2006 |
| WO | 2007/105386 A1 | 9/2007 |
| WO | 2007/125671 A1 | 11/2007 |
| WO | 2008/146597 A1 | 12/2008 |

OTHER PUBLICATIONS

Taerum et al., caplus an 2009:809625.*
Kashiki et al., caplus an 2009:565715.*
Kashiki-et-al-full, Organic Letters, 2009, 11, 2473-2475.*
Taerum-et-al-full, Organic Letters, 2009, 11, 3230-3233.*
Roos et al., caplus an 1970:487909.*
Nicolas et al., caplus an 2003:996231.*
International Search Report dated Dec. 22, 2009 in corresponding foreign patent application PCT/JP2009/069688.
Journal of Organic Chemistry, 1989, vol. 54, pp. 4203-4205, "Photocyclization of Terthiophenes", Jayasuriya, et al.

(Continued)

*Primary Examiner* — Sun Jae Loewe
(74) *Attorney, Agent, or Firm* — Nields, Lemack & Frame, LLC

(57) ABSTRACT

Disclosed are a heterocyclic compound characterized by being represented by formula (1), and a composition of the compound. Also disclosed is an organic electronic device using the compound. (In formula (1), $X^1$, $X^2$ and $X^3$ each independently represents a sulfur atom or a selenium atom; and $R^1$-$R^6$ each independently represents an aromatic hydrocarbon group, an aliphatic hydrocarbon group, a halogen atom, a hydroxyl group, an alkoxyl group, a mercapto group, an alkylthio group, a boronic acid group, a nitro group, a substituted amino group, an amide group, an acyl group, a carboxyl group, an acyloxy group, a cyano group, a sulfo group, a sulfamoyl group, an alkylsulfamoyl group, a carbamoyl group, an alkylcarbamoyl group or a hydrogen atom, provided that all the $R^1$-$R^6$ are not hydrogen atoms at the same time.) The compound represented by formula (1) is suitable for use in an organic electronic device such as an organic EL element, an organic transistor element and a liquid crystal element.

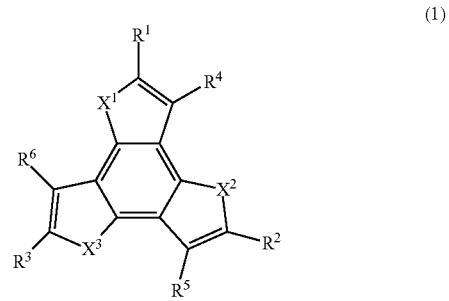

(1)

36 Claims, 5 Drawing Sheets

OTHER PUBLICATIONS

Spectrochimica Acta Part A 56 (2000), pp. 1179-1190, "Structural chemistry of polycyclic heteroaromatic compounds. Part XI. Photoelectron spectra and electronic structures of tetracyclic hetarenes of the triphenylene type", Rademacher, et al.

Organic Letters, 2004, vol. 6, No. 2, pp. 273-276, "Planarized Star-Shaped Oligothiophenes with Enhanced Pi-Electron Delocalization", Nicolas, et al.

Organic Letters, 2009, vol. 11, No. 11, pp. 2473-2475, "One-pot Synthesis of Benzo[b]thiophenes and Benzo[b] selenophenes from o-Halo-Substituted Ethynylbenzenes: Convenient approach to Mono-, Bis-, and Tris- Chalcogenophene-Annulated Benzenes", Kashiki, et al.

Organic Letters, 2009, vol. 11, No. 15, pp. 3230-3233, "Synthesis, Polymerization, and Unusual Properties of New Star-Shaped Thiophene Oligomers", Taerum, et al.

* cited by examiner

HETEROCYCLIC COMPOUND AND USE THEREOF

TECHNICAL FIELD

The present invention relates to a novel heterocyclic compound and use thereof. More specifically, the present invention relates to a specific heterocyclic organic compound and an organic electronics device characterized by containing the same.

BACKGROUND ART

Recently, organic electronics devices have drawn increasing attention. As a feature thereof, the devices have flexible structures, capable of realizing area enlargement, further enabling a cheap and high speed printing method in electronics device manufacturing processes. Examples of representative devices include a liquid crystal device, an organic solar cell device, an organic photoelectric conversion device, an organic EL device and an organic transistor device. The liquid crystal, in which a liquid crystal device is used, has built a global industry as a flat panel display. The organic EL device is expected as a main target as being used continuously in a next generation display. The organic EL device is applied particularly to displays of mobile phones to TV sets and the like, and continuously developed with a view toward further higher functions. Research and development have been made on other devices, e.g., organic solar battery devices with a view toward organic solar batteries serving as a low-cost energy source, and e.g., organic transistor devices toward flexible displays and inexpensive ICs.

To develop these organic electronics devices, it is very important to develop materials constituting the devices. For this, various materials have been studied in individual fields; however, they have not exhibited sufficient performances. Even now, development of materials useful for various devices has been aggressively made.

Of them, a triphenylene derivative has been developed in various ways as materials for organic electronics. For example, among the applications put in practical use is an optical compensation film for enlarging the view angle of a liquid crystal display. Other than this, studies have been made on a charge transport material and a host material for an organic EL material and a semiconductor layer of an organic transistor (Patent Documents 1 and 2).

On the other hand, a benzotrithiophene derivative obtained by replacing the phenyl moiety of triphenylene with thiophene has been synthesized; however, the number of types of derivatives is extremely low and application development thereof has not yet been made at present (Non Patent Documents 1 and 2).

PRIOR ART DOCUMENT

Patent Document

Patent Document 1: JP 7-306317 A
Patent Document 2: JP 2005-156822 A

Non Patent Document

Non Patent Document 1: Org. Chem. 1989, Vol. 54, 4203-4205
Non Patent Document 2: Org. Lett., Vol. 6, No. 2, 273-276 (2004)

SUMMARY OF INVENTION

Problems to be Solved by the Invention

The present invention is to provide a novel heterocyclic compound for use in an organic electronics device and application thereof. More specifically, the present invention is to provide a novel benzotrithiophene (hereinafter, simply referred to as BTT) derivative having a liquid crystalline property and a semiconductor property and being applicable to organic electronics device such as a liquid crystal display, an organic EL device, an organic solar battery device and an organic transistor device.

Means for Solving Problems

The present inventors developed a novel BTT derivative with a view to solving the aforementioned problem, further studied possibility as an organic electronics device and accomplished the present invention.

More specifically, the present invention has the following constitutions:

(1) A heterocyclic compound represented by the following formula (1):

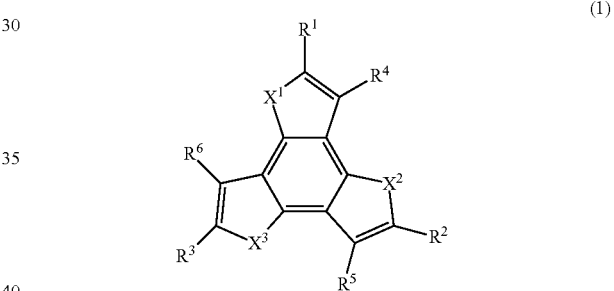

wherein $X^1$, $X^2$ and $X^3$ each independently represent a sulfur atom or a selenium atom; $R^1$ to $R^6$ each independently represent an aromatic hydrocarbon group, an aliphatic hydrocarbon group, a halogen atom, a hydroxyl group, an alkoxyl group, a mercapto group, an alkylthio group, a boronic acid group, a nitro group, a substituted amino group, an amide group, an acyl group, a carboxyl group, an acyloxy group, a cyano group, a sulfo group, a sulfamoyl group, an alkylsulfamoyl group, a carbamoyl group, an alkylcarbamoyl group or a hydrogen atom, provided that they do not simultaneously represent a hydrogen atom.

(2) The heterocyclic compound according to item (1) in which, in the formula (1), $X^1$, $X^2$ and $X^3$ each are a sulfur atom.

(3) The heterocyclic compound according to item (1) or (2) in which, in the formula (1), three or more of $R^1$ to $R^6$ each independently represent an aromatic hydrocarbon group, an aliphatic hydrocarbon group, a halogen atom, a hydroxyl group, an alkoxyl group, a mercapto group, an alkylthio group, a boronic acid group, a nitro group, a substituted amino group, an amide group, an acyl group, a carboxyl group, an acyloxy group, a cyano group, a sulfo group, a sulfamoyl group, an alkylsulfamoyl group, a carbamoyl group or an alkylcarbamoyl group, and the remainder are hydrogen atom(s).

(4) The heterocyclic compound according to any one of items (1) to (3), obtained by a process including a step of reacting a compound represented by the following formula (1-2) with a sulfur compound or a selenium compound.

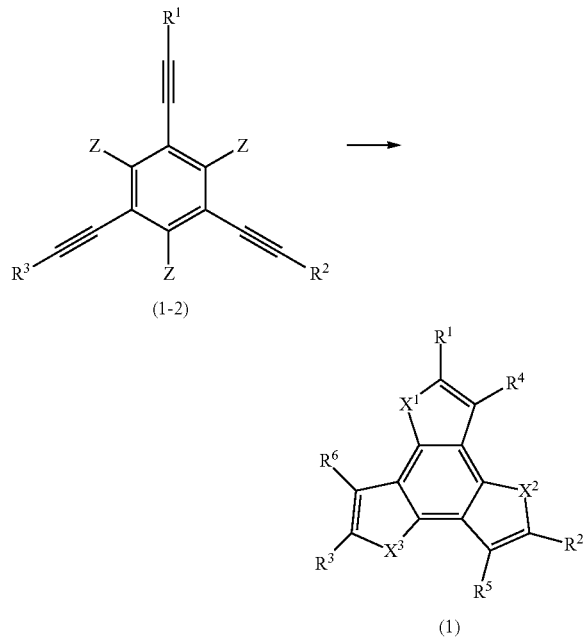

wherein $X^1$, $X^2$ and $X^3$ in formula (1) each independently represent a sulfur atom or a selenium atom; $R^1$ to $R^6$ in formula (1-2) and formula (1) each independently represent an aromatic hydrocarbon group, an aliphatic hydrocarbon group, a halogen atom, a hydroxyl group, an alkoxyl group, a mercapto group, an alkylthio group, a boronic acid group, a nitro group, a substituted amino group, an amide group, an acyl group, a carboxyl group, an acyloxy group, a cyano group, a sulfo group, a sulfamoyl group, an alkylsulfamoyl group, a carbamoyl group, an alkylcarbamoyl group or a hydrogen atom, provided that they do not simultaneously represent a hydrogen atom, and Z in formula (1-2) represents a halogen atom.

(5) The heterocyclic compound according to any one of items (1) to (4), in which, in formula (1), at least one of $R^1$ to $R^6$ is an aromatic hydrocarbon group.

(6) The heterocyclic compound according to item (5), in which the aromatic hydrocarbon group has an amino group.

(7) The heterocyclic compound according to item (5) or (6), in which, in formula (1), $R^1$, $R^3$ and $R^5$ each are an aromatic hydrocarbon group and $R^2$, $R^4$ and $R^6$ each are a hydrogen atom.

(8) The heterocyclic compound according to any one of items (1) to (4), in which, in formula (1), at least one of $R^1$ to $R^6$ is an aliphatic hydrocarbon group.

(9) The heterocyclic compound according to item (8), in which, in formula (1), $R^1$, $R^3$ and $R^5$ each are an aliphatic hydrocarbon group and $R^2$, $R^4$ and $R^6$ each are a hydrogen atom.

(10) The heterocyclic compound according to item (8) or (9), in which the aliphatic hydrocarbon group is a linear or branched alkyl group.

(11) The heterocyclic compound according to any one of items (1) to (4), in which, in formula (1), at least one of $R^1$ to $R^6$ is a halogen atom.

(12) The heterocyclic compound according to item (11), in which, in formula (1), $R^1$ to $R^6$ each are a halogen atom.

(13) The heterocyclic compound according to item (11), in which, in formula (1), $R^1$, $R^3$ and $R^5$ each are a halogen atom and $R^2$, $R^4$ and $R^6$ each are a hydrogen atom.

(14) The heterocyclic compound according to any one of items (11) to (13), in which, the halogen atom is a bromine atom.

(15) The heterocyclic compound according to any one of items (1) to (3), in which, in formula (1), at least one of $R^1$ to $R^6$ is an aldehyde group.

(16) A composition containing the heterocyclic compound according to any one of items (1) to (15), further containing a solvent and (or) a binder.

(17) A thin film formed of the heterocyclic compound according to any one of items (1) to (15) or the composition according to item (16).

(18) An organic semiconductor material containing the heterocyclic compound according to any one of items (1) to (15) or the composition according to item (16).

(19) A liquid crystal material containing the heterocyclic compound according to any one of items (1) to (15) or the composition according to item (16).

(20) An organic electronics device containing the heterocyclic compound according to any one of items (1) to (15), the composition according to item (16), the organic semiconductor material according to item (18) or a liquid crystal material according to item (19).

(21) The organic electronics device according to item (20), in which the device is a photoelectric conversion device, an organic solar battery device, an organic EL device, an organic semiconductor laser device, a liquid crystal display or a thin-film transistor device.

(22) An organic EL device or a thin-film transistor device containing the organic semiconductor material according to item (18).

(23) An organic EL display apparatus composed of the organic EL device according to item (22).

(24) A liquid crystal display device containing the liquid crystal material according to item (19).

(25) A liquid crystal display apparatus having the liquid crystal display device according to item (24) installed therein.

ADVANTAGEOUS EFFECTS OF INVENTION

The present invention relates to a BTT derivative. Since a semiconductor property and a liquid crystalline property can be exhibited, the present invention can provide an organic electronics device and also can provide a flexible electronics product.

MODE FOR CARRYING OUT THE INVENTION

Figure 1:
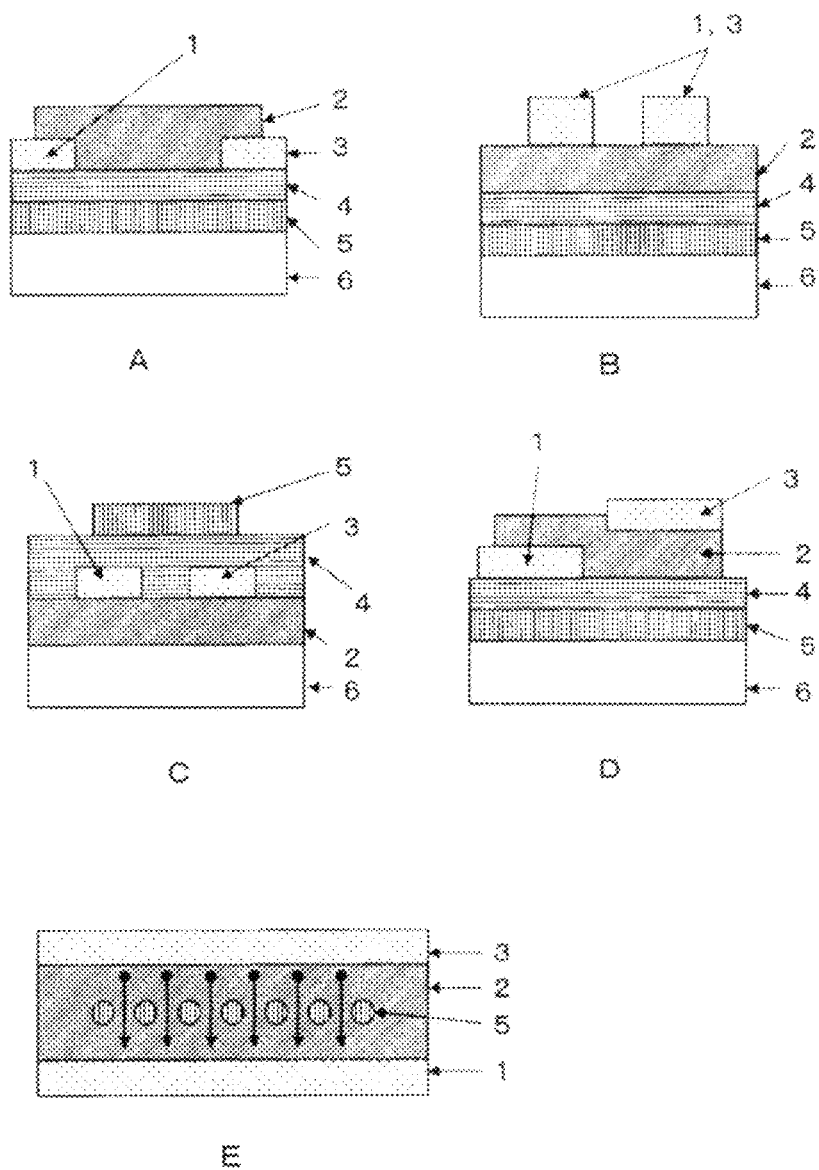
FIG. 1 is a schematic view showing embodiments of the thin-film transistor of the present invention.

Hereinafter, the present invention will be described in more detail.

The present invention relates to a specific heterocyclic compound, i.e., a BTT derivative, and use thereof. First, the compounds of the formula (1) will be described.

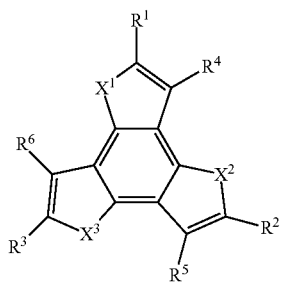

(1)

wherein $X^1$, $X^2$ and $X^3$ each independently represent a sulfur atom or a selenium atom; $R^1$ to $R^6$ each independently represent an aromatic hydrocarbon group, an aliphatic hydrocarbon group, a halogen atom, a hydroxyl group, an alkoxyl group, a mercapto group, an alkylthio group, a boronic acid group, a nitro group, a substituted amino group, an amide group, an acyl group, a carboxyl group, an acyloxy group, a cyano group, a sulfo group, a sulfamoyl group, an alkylsulfamoyl group, a carbamoyl group, an alkylcarbamoyl group or a hydrogen atom, provided that they do not simultaneously represent a hydrogen atom.

$X^1$, $X^2$ and $X^3$ are each independently a sulfur atom or a selenium atom, and preferably a sulfur atom. Furthermore, $X^1$, $X^2$ and $X^3$ are preferably the same.

Examples of the aromatic hydrocarbon groups represented by $R^1$ to $R^6$ include a phenyl group, a naphthyl group, an anthryl group, a phenanthryl group, a pyrenyl group and a benzopyrenyl group. Of these, a phenyl group, a naphthyl group and a pyrenyl group are preferable.

Examples of the substituent that the aromatic hydrocarbon groups may have include, but are not particularly limited to, an aliphatic hydrocarbon group that may have a substituent (examples of the substituent include a halogen atom, a hydroxyl group, a mercapto group, a carboxylic acid group, a sulfonic acid group, a nitro group, an alkoxyl group, an alkyl-substituted amino group, an aryl-substituted amino group, an unsubstituted amino group, an aryl group, an acyl group and an alkoxycarbonyl group); an aromatic hydrocarbon group that may have a substituent (examples of the substituent include an alkyl group, a halogen atom, a hydroxyl group, a mercapto group, a carboxylic acid group, a sulfonic acid group, a nitro group, an alkoxyl group, an alkyl-substituted amino group, an aryl-substituted amino group, an unsubstituted amino group, an aryl group, an acyl group and an alkoxycarbonyl group); a cyano group; an isocyano group; a thiocyanate group; an isothiocyanate group; a nitro group; a nitroso group; an acyl group; an acyloxy group; a halogen atom such as a fluorine atom, a chlorine atom, a bromine atom and an iodine atom; a hydroxyl group; a mercapto group; a substituted or unsubstituted amino group; an alkoxyl group; an alkoxyalkyl group; a thioalkyl group; an aromatic oxy group that may have a substituent; a sulfonic acid group; a sulfinyl group; a sulfonyl group; a sulfonic acid ester group; a sulfamoyl group; a carboxyl group; a carbamoyl group; a formyl group; and an alkoxycarbonyl group. Of them, an aliphatic hydrocarbon group that may have a substituent, an aromatic hydrocarbon group that may have a substituent, a cyano group, a nitro group, an acyl group, a halogen atom, a hydroxyl group, a mercapto group, a substituted or unsubstituted amino group, an alkoxyl group and an aryloxy group that may have a substituent are preferable.

Examples of the aromatic hydrocarbon group mentioned therein include a condensed polycyclic hydrocarbon group such as a pyrenyl group and a benzopyrenyl group; a heterocyclic hydrocarbon group such as a pyridyl group, a pyrazyl group, a pyrimidyl group, a quinolyl group, an isoquinolyl group, a pyrrolyl group, an indolenyl group, an imidazolyl group, a carbazolyl group, a thienyl group, a furyl group, a pyranyl group and a pyridonyl group; and a condensed heterocyclic hydrocarbon group such as a benzoquinolyl group, an anthraquinolyl group, a benzothienyl group and a benzofuryl group.

Furthermore, examples of the aliphatic hydrocarbon groups represented by $R^1$ to $R^6$ include a saturated or unsaturated and linear, branched or cyclic aliphatic hydrocarbon group, and the group preferably has 1 to 20 carbon atoms. Examples of the saturated or unsaturated and linear or branched aliphatic hydrocarbon group include a methyl group, an ethyl group, a propyl group, an isopropyl group, a n-butyl group, an iso-butyl group, an allyl group, a t-butyl group, a n-pentyl group, a n-hexyl group, a n-octyl group, a n-decyl group, a n-dodecyl group, a n-stearyl group and a n-butenyl group. Furthermore, examples of the cyclic aliphatic hydrocarbon group include a cycloalkyl group having 3 to 12 carbon atoms such as a cyclohexyl group, a cyclopentyl group, an adamantyl group and a norbornyl group.

Furthermore, examples of the substituent that an aliphatic hydrocarbon group may have include, but are not particularly limited to, a halogen atom, a cyano group, a hydroxyl group, a mercapto group, a nitro group, an alkoxyl group, a carboxylic acid group, a sulfonic acid group, an alkyl-substituted amino group, an aryl-substituted amino group, an unsubstituted amino group, an acyl group and an aromatic hydrocarbon group that may have a substituent (examples of the substituent include an alkyl group, a halogen atom, a hydroxyl group, a mercapto group, a carboxylic acid group, a sulfonic acid group, a nitro group, an alkoxyl group, an alkyl-substituted amino group, an aryl-substituted amino group, an unsubstituted amino group, an aryl group, an acyl group and an alkoxycarbonyl group). Of them, an aromatic hydrocarbon group that may have a substituent, a cyano group, a nitro group, an acyl group, a halogen atom, a hydroxyl group, a mercapto group, a substituted or unsubstituted amino group, an alkoxyl group and an aryloxy group that may have a substituent are preferable. The aromatic hydrocarbon groups shown therein are the same as mentioned above.

Examples of the halogen atom include a fluorine atom, a chlorine atom, a bromine atom and an iodine atom, and a fluorine atom, a chlorine atom and a bromine atom are preferable.

Examples of the alkoxyl group include an alkoxyl group having 1 to 24 carbon atoms and an alkoxyl group having 1 to 18 carbon atoms is preferable.

Examples of the alkylthio group include an alkylthio group having 1 to 24 carbon atoms and an alkylthio group having 1 to 18 carbon atoms is preferable.

Examples of the amino group include an unsubstituted amino group, a monosubstituted amino group and a disubstituted amino group. Examples of the substituent include an aromatic hydrocarbon group that may have a substituent (examples of the substituent include an alkyl group, a halogen atom, a hydroxyl group, a mercapto group, a carboxylic acid group, a sulfonic acid group, a nitro group, an alkoxyl group, an alkyl-substituted amino group, an aryl-substituted amino group, an unsubstituted amino group, an aryl group, an acyl group and an alkoxycarbonyl group), an aliphatic hydrocarbon group that may have a substituent (examples of the substituent include a halogen atom, a hydroxyl group, a mercapto group, a carboxylic acid group, a sulfonic acid group, a nitro group, an alkoxyl group, an alkyl-substituted amino group, an aryl-substituted amino group, an unsubstituted amino group, an aryl group, an acyl group and an alkoxycarbonyl group). The aromatic hydrocarbon groups and aliphatic hydrocarbon groups are the same as previously mentioned ones.

Examples of the amide group include an amide group having an aliphatic hydrocarbon group such as acetamide and an amide group having an aromatic hydrocarbon group such as benzamide.

Examples of the acyl group include a formyl group, an acyl group having an aliphatic hydrocarbon group such as an acetyl group and an acyl group having an aromatic hydrocarbon group such as a benzoyl group. The acyl group of the acyloxy group is the same as previously mentioned as to the acyl group. Examples of the sulfamoyl group include an unsubstituted sulfamoyl group and a substituted sulfamoyl group. Furthermore, examples of the carbamoyl group include an unsubstituted carbamoyl group and a substituted carbamoyl group. Examples of the substituent of them include an aromatic hydrocarbon group that may have a substituent (examples of the substituent include an alkyl group, a halogen atom, a hydroxyl group, a mercapto group, a carboxylic acid group, a sulfonic acid group, a nitro group, an alkoxyl group, an alkyl-substituted amino group, an aryl-substituted amino group, an unsubstituted amino group, an aryl group, an acyl group and an alkoxycarbonyl group), an aliphatic hydrocarbon group that may have a substituent (examples of the substituent include a halogen atom, a hydroxyl group, a mercapto group, a carboxylic acid group, a sulfonic acid group, a nitro group, an alkoxyl group, an alkyl-substituted amino group, an aryl-substituted amino group, an unsubstituted amino group, an aryl group, an acyl group and an alkoxycarbonyl group). The aromatic hydrocarbon groups and aliphatic hydrocarbon groups each are the same as previously described ones. The aromatic hydrocarbon group and aliphatic hydrocarbon group mentioned herein whose hydrogen atom(s) may be substituted with an appropriate substituent(s).

A heterocyclic compound represented by formula (1) can be synthesized, as described in a known method disclosed in Non Patent Document 2, by reacting dibromothiophene as a raw material with tetrahydrothiophen-3-one by use of butyl lithium at a low temperature of −70° C. and then reacting with 2-thienyl magnesium bromide subsequently, and finally condensing to form a ring by a photooxidation reaction. When the BTT derivative thus obtained is tribrominated, as described in the following Scheme 1, a compound of formula (3) can be easily obtained. With this, an acetylene derivative is reacted in accordance with the Sonogashira reaction to obtain a compound of formula (4) having an unsaturated aliphatic hydrocarbon group. This is furthermore subjected to a reductive reaction to obtain a compound of formula (5) having a saturated aliphatic hydrocarbon group. Furthermore, cross-coupling of this compound with a boronic acid derivative of an aromatic hydrocarbon is performed to obtain a compound of formula (6) having an aromatic hydrocarbon group (Scheme 2). Starting from trichloro triiodobenzene of formula (7), a compound of formula (8) can be easily synthesized through the Sonogashira reaction using the corresponding acetylene derivative.

Furthermore, as shown in Scheme 3, the compound of formula (8) is subjected to a cyclization reaction to directly and efficiently obtain a BTT derivative of formula (9). The reaction of Scheme 3 is, unlike the aforementioned conventional method, related to a process for synthesizing a benzochalcogen derivative in which a desired compound of formula (9) can be easily obtained at low cost and in a high yield by reacting a sulfur compound (or selenium compound) in a solvent under heating conditions.

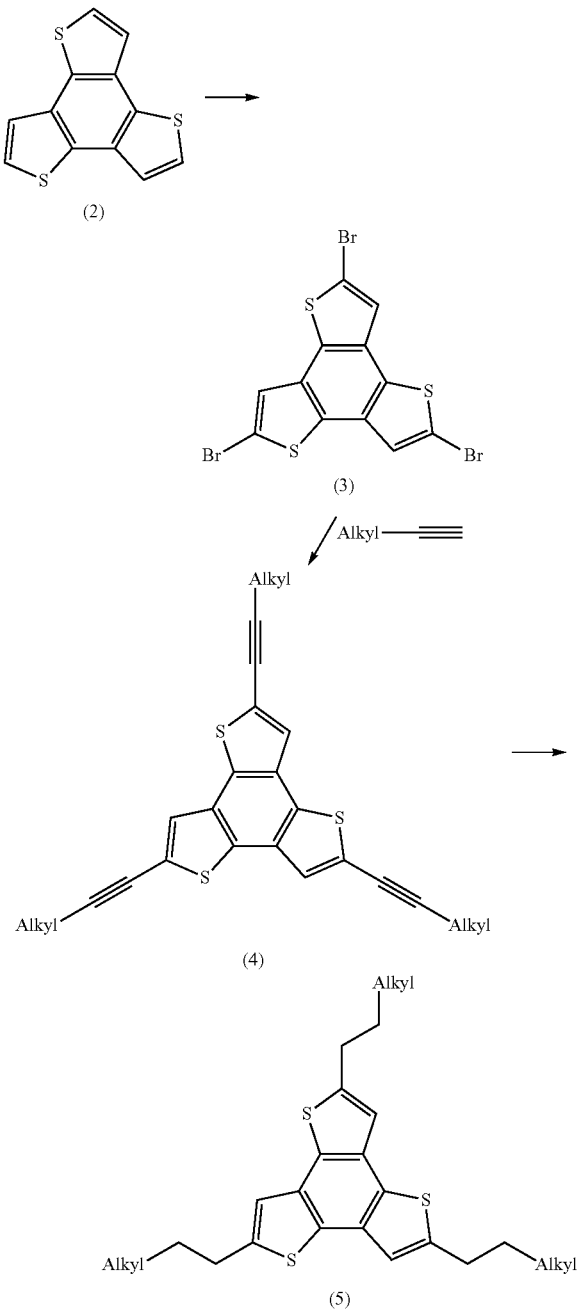

Scheme 1

Scheme 2

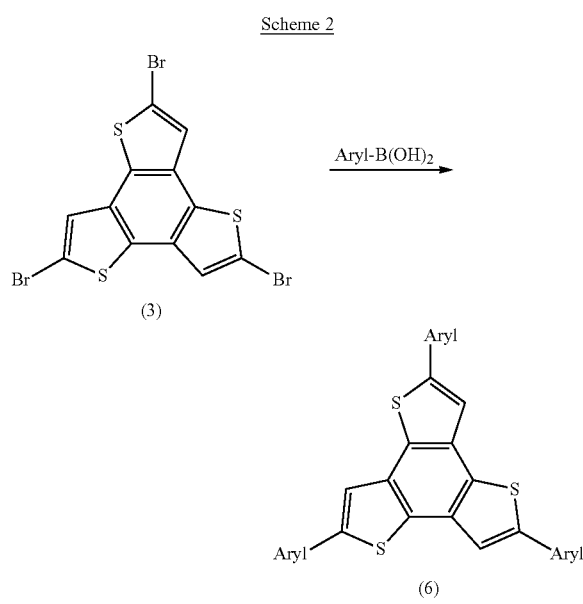

Scheme 3

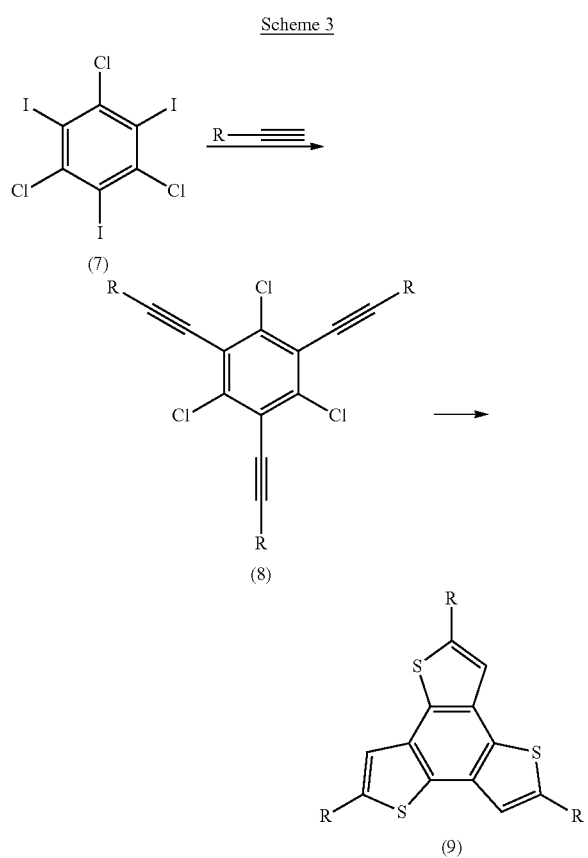

R is the corresponding substituent

Next, the process for synthesizing a compound of formula (9) from a compound of formula (8) shown in the reaction formula of Scheme 3 above will be more specifically described with reference to Scheme 4 below, as follows. A compound of formula (1-2) of Scheme 4 corresponds to a compound of formula (8) described in Scheme 3 above, more specifically, corresponds to a compound obtained by replacing the chlorine atoms of the compound of formula (8) with halogen atoms.

Scheme 4

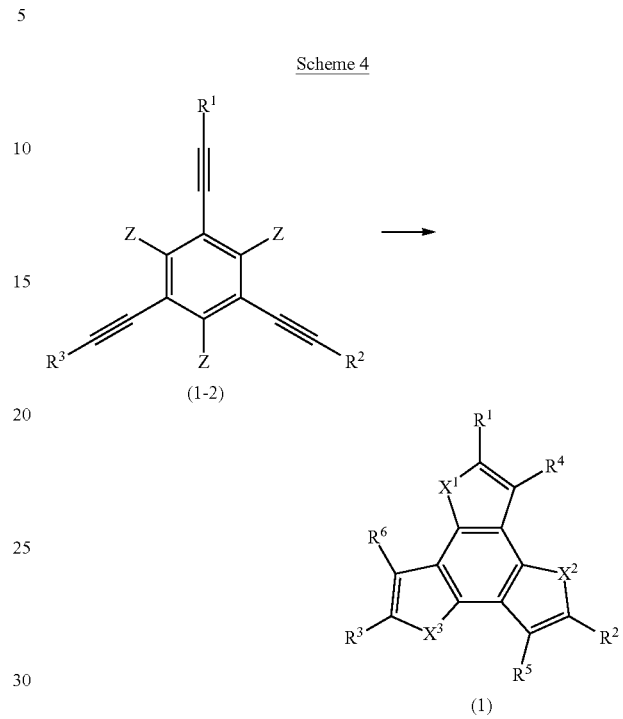

wherein $X^1$, $X^2$ and $X^3$ each independently represent a sulfur atom or a selenium atom; $R^1$ to $R^6$ in formula (1-2) and formula (1) each independently an aromatic hydrocarbon group, an aliphatic hydrocarbon group, a halogen atom, a hydroxyl group, an alkoxyl group, a mercapto group, an alkylthio group, a boronic acid group, a nitro group, an amino group, an amide group, an acyl group, a carboxyl group, an acyloxy group, a cyano group, a sulfo group, a sulfamoyl group, an alkyl sulfamoyl group, a carbamoyl group, an alkyl carbamoyl group or a hydrogen atom, provided that they do not simultaneously represent a hydrogen atom, Z is a halogen atom; in $R^1$, $R^2$, and $R^3$ above, the description including preferable substituents follows the description regarding the compound of formula (1) above.

In the above formula (1-2), examples of the halogen atom represented by Z include a chlorine atom, a bromine atom and an iodine atom and a chlorine atom is preferable.

The sulfur compound used in Scheme 4 above is usually at least one selected from the group consisting of sulfur, hydrogen sulfide, a metal hydrosulfide and a metal sulfide. They may be used singly or in combination. Examples of the metal hydrosulfide include hydrous and/or anhydrous alkali metal hydrosulfides. Preferable specific examples thereof include sodium hydrosulfide and potassium hydrosulfide. Examples of the metal sulfide include hydrous and/or anhydrous alkali metal sulfides and a transition metal sulfide. Specific examples thereof include sodium sulfide, potassium sulfide, iron sulfide and copper sulfide. Preferable examples of the sulfur compound include sulfur, hydrous and/or anhydrous sodium hydrosulfide, hydrous and/or anhydrous sodium sulfide, and more preferably hydrous sodium hydrosulfide and hydrous sodium hydrosulfide.

Examples of the selenium compound used in Scheme 4 include a metal selenium, NaSeH, KSeH and selenium oxide. Preferred are a metal selenium and NaSeH, and more preferred is a metal selenium.

In a manufacturing method for a compound of formula (1) of Scheme 4 above, the sulfur compound or selenium compound for the reaction is used usually in an amount of 3 to 30 moles relative to one mole of a compound of formula (1-2), preferably 4 to 16 moles and more preferably 5 to 12 moles.

In the manufacturing method of Scheme 4 above, at least one type of solvent is preferably contained in a reaction mixture. This is preferable, because a rate of the reaction for manufacturing a compound of formula (1) is improved by addition of a solvent.

Preferable examples of the solvent used in Scheme 4 include an amide such as N-methyl-2-pyrrolidone, N,N-dimethyl formamide and N,N-dimethyl acetamide; a glycol such as ethylene glycol, propylene glycol and polyethylene glycol; or a sulfoxide such as dimethyl sulfoxide. More preferred are N-methyl-2-pyrrolidone, N,N-dimethyl formamide and N,N-dimethyl acetamide, and particularly preferred is a solvent having a boiling point of 100° C. or more.

The solvent may be used in an amount of 0.01 to 100 moles relative to 1 mole of a compound of formula (8), preferably 0.1 to 80 moles and more preferably 20 to 50 moles. In the manufacturing method, the reaction is preferably performed at a temperature of −50° C. to 300° C. If necessary, the reaction temperature may be changed within the temperature range. The temperature is preferably −10° C. to 250° C. and more preferably 40° C. to 200° C.

In performing a synthesis reaction of a compound represented by the compound of formula (9), addition of a catalyst is not essential; however, the reaction often proceeds smoothly by using a catalyst. If the reaction does not proceed smoothly, a catalyst is preferably used. Examples of the metal catalyst to be used include a copper atom, a metal halide such as copper chloride (I), copper chloride (II), copper bromide (I), copper bromide (II), copper iodide (I) and copper iodide (II), and particularly preferred is copper halide. More preferred are a copper atom, a copper bromide (I) and copper iodide (I).

The use amount of catalyst is 0.01 to 1 mole relative to 1 mole of a compound of formula (8), preferably 0.1 to 0.5 moles and more preferably 0.1 to 0.2 moles. The reaction time is usually one hour to 50 hours. However, so as to finish the reaction within about 24 hours, the reaction temperature and the amounts of a halogenation agent and a sulfur compound or a selenium compound are preferably appropriately controlled.

Other substituents are reacted as follows. For example, a compound of formula (2), a compound of formula (5), a compound of formula (6) and a compound of formula (9) can be subjected to the Vilsmeier reaction to produce a formyl derivative. A general sulfonation reaction can produce a sulfone derivative. A general nitration reaction can produce a nitro derivative. The Friedel-Crafts reaction with halogenation acyl can produce an acyl derivative. Cyano substitution can be performed by use of a bromo compound of formula (3) to produce a cyano derivative. The Ullmann reaction with an amino compound can produce an amino derivative. A reaction with an alcohol compound can produce an alkoxyl derivative. A reaction with a thiol compound can produce an alkylthio derivative. The Grignard reaction can produce a boronic acid derivative. Hydrolysis with a cyano group can produce a carboxyl derivative. The reduction with a nitro group can produce an amino derivative. The reaction of an amino derivative with a halogenated acyl can produce an amide derivative. The aforementioned reactions can be used in combination to synthesize various types of derivatives.

Furthermore, BTT (2) can be subjected to not only tribromination but also mono bromination, dibromination to tetrabromination, pentabromination, hexabromination, halogenation with a xenogeneic halogen atom, or a combination of these reactions to control the number and types of substituents $R^1$ to $R^6$. In the reaction formula, an example where X is a sulfur atom is mentioned, a compound of a selenium atom can be obtained in the same manner.

A method for purifying a heterocyclic compound represented by the above formula (1) is not particularly limited and a known method such as recrystallization, column chromatography and vacuum sublimation purification can be employed. Furthermore, if necessary, these methods may be used in combination.

In Table 1 below, specific examples of a heterocyclic compound represented by the formula (1) are listed. In the Table, a cyclohexyl group is represented by CH; a phenyl group by Ph, 4-dodecyl phenyl group by DP, 1-naphthyl group by Np and 2-thienyl group by Th.

TABLE 1

| No. | $X^1$ | $X^2$ | $X^3$ | $R^1$ | $R^4$ | $R^2$ | $R^5$ | $R^3$ | $R^6$ |
|---|---|---|---|---|---|---|---|---|---|
| 1 | S | S | S | CH3 | CH3 | CH3 | CH3 | CH3 | CH3 |
| 2 | S | S | S | CH3 | H | CH3 | H | CH3 | H |
| 3 | S | S | S | CH3 | C6H13 | CH3 | C6H13 | CH3 | C6H13 |
| 4 | S | S | S | H | C8H17 | H | C8H17 | H | C8H17 |
| 5 | S | S | S | C6H13 | H | C6H13 | H | C6H13 | H |
| 6 | S | S | S | C10H21 | C10H21 | C10H21 | C10H21 | C10H21 | C10H21 |
| 7 | S | S | S | C10H21 | H | C10H21 | H | C10H21 | H |
| 8 | S | S | S | C12H25 | H | C12H25 | H | C12H25 | H |
| 9 | S | S | S | C=CHC4H9 | H | C=CHC4H9 | H | C=CHC4H9 | H |
| 10 | S | S | S | C=CHC6H13 | H | C=CHC6H13 | H | C=CH6H13 | H |
| 11 | S | S | S | C=CC8H17 | H | C=CC8H17 | H | C=CC8H17 | H |
| 12 | S | S | S | C18H37 | H | C18H37 | H | C18H37 | H |
| 13 | S | S | S | C18H37 | C18H37 | C18H37 | C18H37 | C18H37 | C18H37 |
| 14 | S | S | S | C24H49 | H | C24H49 | H | C24H49 | H |
| 15 | S | S | S | C8F17 | H | C8F17 | H | C8F17 | H |
| 16 | S | S | S | C2H4C3F7 | H | C2H4C3F7 | H | C2H4C3F7 | H |
| 17 | S | S | S | C4H8Cl | C4H8Cl | C4H8Cl | C4H8Cl | C4H8Cl | C4H8Cl |
| 18 | S | S | S | C4H9 | C18H37 | C4H9 | C18H37 | C4H9 | C18H37 |
| 19 | Se | Se | Se | C10H25 | H | C10H25 | H | C10H25 | H |
| 20 | Se | Se | Se | C12H25 | H | C12H25 | H | C12H25 | H |
| 21 | Se | Se | Se | C12H25 | C12H25 | C12H25 | C12H25 | C12H25 | C12H25 |
| 22 | S | S | S | CH2CH=CH2 | H | CH2CH=CH2 | H | CH2CH=CH2 | H |
| 23 | S | S | S | C(CH3)3 | H | C(CH3)3 | H | C(CH3) | H |
| 24 | S | S | S | CH(CH3)2 | H | H | H | CH(CH3)2 | H |
| 25 | S | S | S | CH | H | CH | H | CH | H |

TABLE 1-continued

| No. | $X^1$ | $X^2$ | $X^3$ | $R^1$ | $R^4$ | $R^2$ | $R^5$ | $R^3$ | $R^6$ |
|---|---|---|---|---|---|---|---|---|---|
| 26 | S | S | S | C2H4CN | C2H4CN | C2H4CN | C2H4CN | C2H4CN | C2H4CN |
| 27 | S | S | S | CH2Ph | CH2Ph | CH2Ph | CH2Ph | CH2Ph | CH2Ph |
| 27 | S | S | S | CH2Ph | H | CH2Ph | H | CH2Ph | H |
| 28 | S | S | S | C4H8Np | C4H8Np | C4H8Np | C4H8Np | C4H8Np | C4H8Np |
| 29 | S | S | S | C5H10OH | C5H10OH | C5H10OH | C5H10OH | C5H10OH | C5H10OH |
| 30 | S | S | S | C2H4COOH | C2H4COOH | C2H4COOH | C2H4COOH | C2H4COOH | C2H4COOH |
| 31 | S | S | S | C2H4NH2 | H | C2H4NH2 | H | C2H4NH2 | H |
| 32 | S | S | S | Cl | H | Cl | H | Cl | H |
| 33 | S | S | S | Br | H | Br | H | Br | H |
| 34 | S | S | S | Br | H | H | H | H | H |
| 35 | S | S | S | Br | H | Br | H | H | H |
| 36 | S | S | S | Br | Br | Br | H | Br | H |
| 37 | S | S | S | Br | Br | Br | Br | Br | H |
| 38 | S | S | S | Br | Br | Br | Br | Br | Br |
| 39 | S | S | S | F | F | F | F | F | F |
| 40 | S | S | S | I | H | H | H | H | H |
| 41 | S | S | S | I | H | I | H | I | H |
| 42 | S | S | S | I | I | I | I | I | I |
| 43 | S | S | S | OCH3 | H | OCH3 | H | OCH3 | H |
| 44 | S | S | S | OC8H17 | H | OCH8H17 | H | OC8H17 | H |
| 45 | S | S | S | OC12H25 | OC12H25 | OC12H25 | OC12H25 | OC12H25 | OC12H25 |
| 46 | Se | Se | Se | OC12H25 | OC12H25 | OC12H25 | OC12H25 | OC12H25 | OC12H25 |
| 47 | S | S | S | OC18H37 | OC18H37 | OC18H37 | OC18H37 | OC18H37 | OC18H37 |
| 48 | S | S | S | C2H4OCH3 | H | C2H4OCH3 | H | C2H4OCH3 | H |
| 49 | S | S | S | C2H4OCH3 | C2H4OCH3 | C2H4OCH3 | C2H4OCH3 | C2H4OCH3 | C2H4OCH3 |
| 50 | S | S | S | OC8H16OCH3 | OC8H16OCH3 | OC8H16OCH3 | OC8H16OCH3 | OC8H16OCH3 | OC8H16OCH3 |
| 51 | S | S | S | OC8H16OCH3 | H | OC8H16OCH3 | H | OC8H16OCH3 | H |
| 52 | S | S | S | OC8H16OC4H9 | OC8H16OC4H9 | OC8H16OC4H9 | OC8H16OC4H9 | OC8H16OC4H9 | OC8H16OC4H9 |
| 53 | S | S | S | OC2H4Ph | OC2H4Ph | OC2H4Ph | OC2H4Ph | OC2H4Ph | OC2H4Ph |
| 54 | S | S | S | OC2H4Ph | H | OC2H4Ph | H | OC2H4Ph | H |
| 55 | S | S | S | OC8H16OPh | OC8H16OPh | OC8H16OPh | OC8H16OPh | OC8H16OPh | OC8H16OPh |
| 56 | S | S | S | C8H16OPh | C8H16OPh | C8H16OPh | C8H16OPh | C8H16OPh | C8H16OPh |
| 57 | S | S | S | SC12H25 | SC12H25 | SC12H25 | SC12H25 | SC12H25 | SC12H2 |
| 58 | S | S | S | C12H25 | SC12H25 | C12H25 | SC12H25 | C12H25 | SC12H25 |
| 59 | S | S | S | SC12H25 | H | SC12H25 | H | SC12H25 | H |
| 60 | S | S | S | NHCH3 | NHCH3 | NHCH3 | NH2 | NHCH3 | NHCH3 |
| 61 | S | S | S | NHCH3 | H | NHCH3 | H | NHCH3 | H |
| 62 | S | S | S | NHC4H9 | NHC4H9 | NHC4H9 | NHC4H9 | NHC4H9 | NHC4H9 |
| 63 | S | S | S | NHC12H25 | H | NHC12H25 | H | NHC12H25 | H |
| 64 | S | S | S | N(C12H25)2 | H | N(C12H25)2 | H | N(C12H25)2 | H |
| 65 | S | S | S | N(C12H25)2 | N(C12H25)2 | N(C12H25)2 | N(C12H25)2 | N(C12H25)2 | N(C12H25)2 |
| 66 | S | S | S | NHPh | NHPh | NHPh | NHPh | NHPh | NHPh |
| 67 | S | S | S | N(Ph)2 | H | N(Ph)2 | H | N(Ph)2 | H |
| 68 | S | S | S | N(Ph)2 | N(Ph)2 | N(Ph)2 | N(Ph)2 | N(Ph)2 | N(Ph)2 |
| 69 | S | S | S | NPhNp | H | NPhNp | H | NPhNp | H |
| 70 | S | S | S | NPhNp | NPhNp | NPhNp | NPhNp | NPhNp | NPhNp |
| 71 | S | S | S | NHCOCH3 | H | NHCOCH3 | H | NHCOCH3 | H |
| 72 | S | S | S | NHCOCH3 | NHCOCH3 | NHCOCH3 | NHCOCH3 | NHCOCH3 | NHCOCH3 |
| 73 | S | S | S | NHCOCH3 | H | H | H | H | H |
| 74 | S | S | S | NHCOC5H11 | H | NHCOC5H11 | H | NHCOC5H11 | H |
| 75 | S | S | S | NHCOC10H21 | NHCOC10H21 | NHCOC10H21 | NHCOC10H21 | NHCOC10H21 | NHCOC10H21 |
| 76 | S | S | S | NHCOPh | H | NHCOPh | H | NHCOPh | H |
| 77 | S | S | S | NHCOPh | NHCOPh | NHCOPh | NHCOPh | NHCOPh | NHCOPh |
| 78 | S | S | S | NHCOPh | H | H | H | H | H |
| 79 | S | S | S | NHCOTh | NHCOTh | NHCOTh | NHCOTh | NHCOTh | NHCOTh |
| 80 | S | S | S | CHO | H | H | H | H | H |
| 81 | S | S | S | CHO | H | CHO | H | CHO | H |
| 82 | S | S | S | CHO | CHO | CHO | CHO | CHO | CHO |
| 83 | Se | Se | Se | CHO | H | H | H | H | H |
| 84 | Se | Se | Se | CHO | H | CHO | H | CHO | H |
| 85 | S | S | S | COCH3 | H | H | H | H | H |
| 86 | S | S | S | COCH3 | COCH3 | COCH3 | COCH3 | COCH3 | COCH3 |
| 87 | S | S | S | COCH3 | H | COCH3 | H | COCH3 | H |
| 88 | S | S | S | COCF3 | COCF3 | COCF3 | COCF3 | COCF3 | COCF3 |
| 89 | S | S | S | COC8H17 | COC8H17 | COC8H17 | COC8H17 | COC8H17 | COC8H17 |
| 90 | S | S | S | COC18H37 | H | COC18H37 | H | COC18H37 | H |
| 91 | S | S | S | COPh | COPh | COPh | COPh | COPh | COPh |
| 92 | S | S | S | COPh | H | COPh | H | COPh | H |
| 93 | S | S | S | CONp | H | CONp | H | CONp | H |
| 94 | S | S | S | COC3H6Ph | COC3H6Ph | COC3H6Ph | COC3H6Ph | COC3H6Ph | COC3H6Ph |
| 95 | S | S | S | OCOCH3 | H | H | H | H | H |
| 96 | 5 | S | S | OCOCH3 | H | OCOCH3 | H | OCOCH3 | H |
| 97 | S | S | S | OCOCH3 | OCOCH3 | OCOCH3 | OCOCH3 | OCOCH3 | OCOCH3 |
| 98 | S | S | S | OCOC8H17 | H | OCOC8H17 | H | OCOC8H17 | H |
| 99 | S | S | S | OCOC8H17 | OCOC8H17 | OCOC8H17 | OCOC8H17 | OCOC8H17 | OCOC8H17 |
| 100 | S | S | S | OCOC12H25 | H | OCOC12H25 | H | OCOC121125 | H |

TABLE 1-continued

| No. | X¹ | X² | X³ | R¹ | R⁴ | R² | R⁵ | R³ | R⁶ |
|---|---|---|---|---|---|---|---|---|---|
| 101 | S | S | S | OCOC12H25 | OCOC12H25 | OCOC12H25 | OCOC12H25 | OCOC12H25 | OCOC12H25 |
| 102 | S | S | S | C12H25 | OCOC12H25 | C12H25 | OCOC12H25 | C12H25 | OCOC12H25 |
| 103 | S | S | S | OCOPh | H | OCOPh | H | OCOPh | H |
| 104 | S | S | S | OCOPh | OCOPh | OCOPh | OCOPh | OCOPh | OCOPh |
| 105 | S | S | S | OCONp | H | OCONp | H | OCONp | H |
| 106 | S | S | S | OCODP | H | OCODP | H | OCODP | H |
| 107 | S | S | S | OCODP | OCODP | OCODP | OCODP | OCODP | OCODP |
| 108 | S | S | S | OH | H | H | H | H | H |
| 109 | S | S | S | OH | OH | OH | OH | OH | OH |
| 110 | S | S | S | OH | H | OH | H | OH | H |
| 111 | S | S | S | SH | H | SH | H | SH | H |
| 112 | S | S | S | SH | SH | SH | SH | SH | SH |
| 113 | S | S | S | B(OH)2 | H | H | H | H | H |
| 114 | S | S | S | B(OH)2 | H | B(OH)2 | H | B(OH)2 | H |
| 115 | S | S | S | B(OH)2 | B(OH)2 | B(OH)2 | B(OH)2 | B(OH)2 | B(OH)2 |
| 116 | S | S | S | NO2 | H | H | H | H | H |
| 117 | S | S | S | NO2 | H | NO2 | H | H | H |
| 118 | S | S | S | NO2 | H | NO2 | H | NO2 | H |
| 119 | S | S | S | NO2 | NO2 | NO2 | H | NO2 | H |
| 120 | S | S | S | NO2 | NO2 | NO2 | NO2 | NO2 | NO2 |
| 121 | S | S | S | SO3H | H | H | H | H | H |
| 122 | S | S | S | SO3H | H | SO3H | H | SO3H | H |
| 123 | S | S | S | SO3H | SO3H | SO3H | H | SO3H | H |
| 124 | S | S | S | SO3Na | H | SO3Na | H | SO3Na | H |
| 125 | S | S | S | SO2Cl | H | H | H | H | H |
| 126 | S | S | S | SO2Cl | H | SO2Cl | H | SO2Cl | H |
| 127 | S | S | S | COOH | H | H | H | H | H |
| 128 | S | S | S | COOH | H | COOH | H | COOH | H |
| 129 | S | S | S | COOH | COOH | COOH | COOH | COOH | COOH |
| 130 | S | S | S | COCl | H | COCl | H | COCl | H |
| 131 | S | S | S | CONHCH3 | H | CONHCH3 | H | CONHCH3 | H |
| 132 | S | S | S | CONHC8H17 | H | CONHC8H17 | H | CONHC8H17 | H |
| 133 | S | S | S | CONHC8H17 | CONHC8H17 | CONHC8H17 | CONHC8H17 | CONHC8H17 | CONHC8H17 |
| 134 | S | S | S | CONHPh | H | CONHPh | H | CONHPh | H |
| 135 | S | S | S | CONH2 | H | CONH2 | H | CONH2 | H |
| 136 | S | S | S | SO2NH2 | H | SO2NH2 | H | SO2NH2 | H |
| 137 | S | S | S | SO2NHC4H9 | H | SO2NHC4H9 | H | SO2NHC4H9 | H |
| 138 | S | S | S | CN | H | H | H | H | H |
| 139 | S | S | S | CN | H | CN | H | CN | H |
| 140 | S | S | S | CN | CN | CN | CN | CN | CN |
| 141 | S | S | S | CN | Br | CN | Br | CN | Br |
| 142 | S | S | S | Ph | H | Ph | H | Ph | H |
| 143 | S | S | S | Ph | Ph | Ph | Ph | Ph | Ph |
| 144 | S | S | S | Np | H | Np | H | Np | H |
| 145 | Se | S | Se | Ph | H | Ph | H | Ph | H |
| 146 | Se | Se | Se | Ph | Ph | Ph | Ph | Ph | Ph |
| 147 | S | S | S | DP | H | DP | H | DP | H |
| 148 | S | S | S | DP | Ph | DP | Ph | DP | Ph |
| 149 | S | S | S | C4H9 | Br | C4H9 | Br | C4H9 | Br |
| 150 | S | S | S | C12H25 | Br | C12H25 | Br | C12H25 | Br |
| 151 | S | S | S | OC12H25 | Br | OC12H25 | Br | OC12H25 | Br |
| 152 | S | S | S | N(C12H25)2 | Br | N(C12H25)2 | Br | N(C12H25)2 | Br |
| 153 | S | S | S | Ph | Br | Ph | Br | Ph | Br |
| 154 | S | S | S | Ph | I | Ph | I | Ph | I |
| 155 | S | S | S | C6H13 | C12H25 | C6H13 | C12H25 | C6H13 | C12H25 |
| 156 | S | S | S | C6H13 | OC6H13 | C6H13 | OC6H13 | C6H13 | OC6H13 |
| 157 | S | S | S | C4H9 | Ph | C4H9 | Ph | C4H9 | Ph |
| 158 | S | S | S | C≡CPh | C12H25 | C≡CPh | C12H25 | C≡CPh | C12H25 |
| 159 | S | S | S | C≡CPh | H | C≡CPh | H | C≡CPh | H |
| 160 | S | S | S | C≡CDP | C12H25 | C≡CDP | C12H25 | C≡CDP | C12H25 |
| 161 | S | S | S | C≡CDP | OC12H25 | C≡CDP | OC12H25 | C≡CDP | OC12H25 |

17
1001
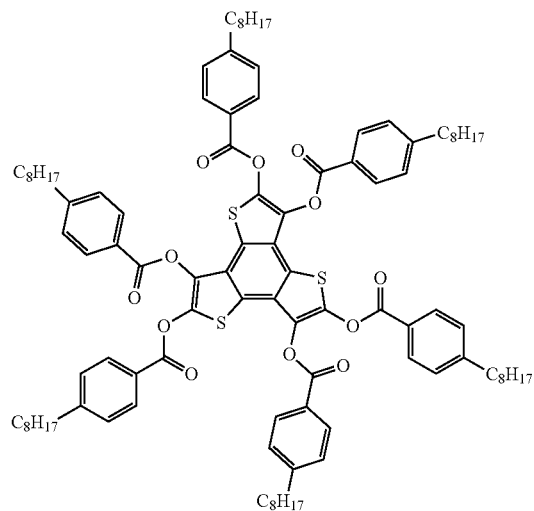
18
1002
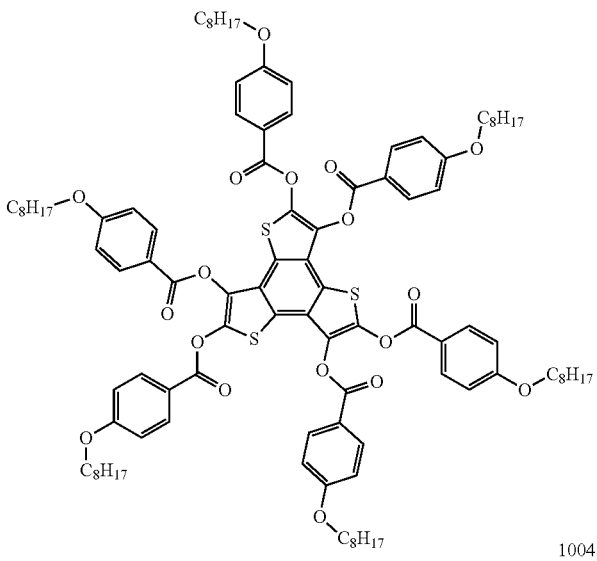
1003
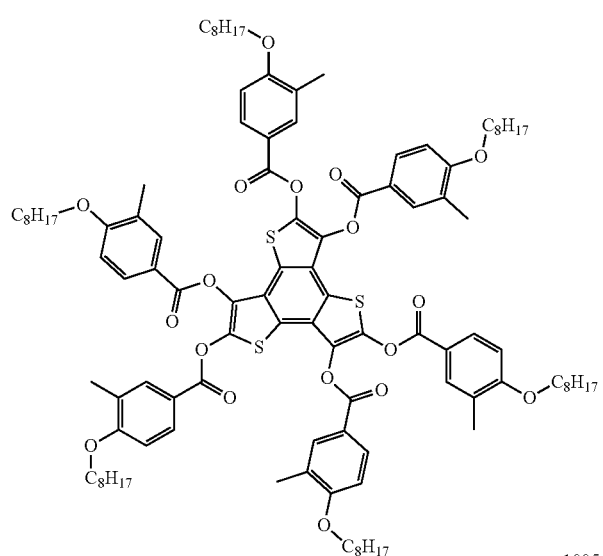
1004
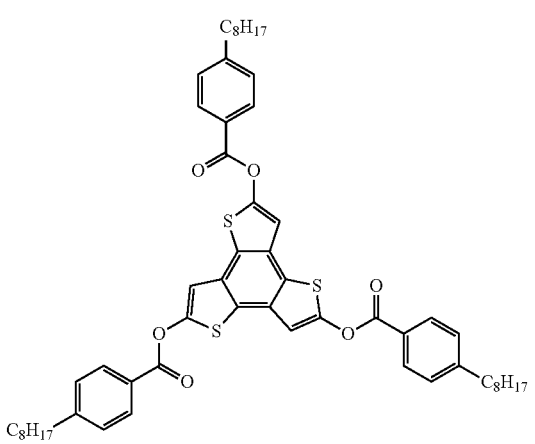
1005
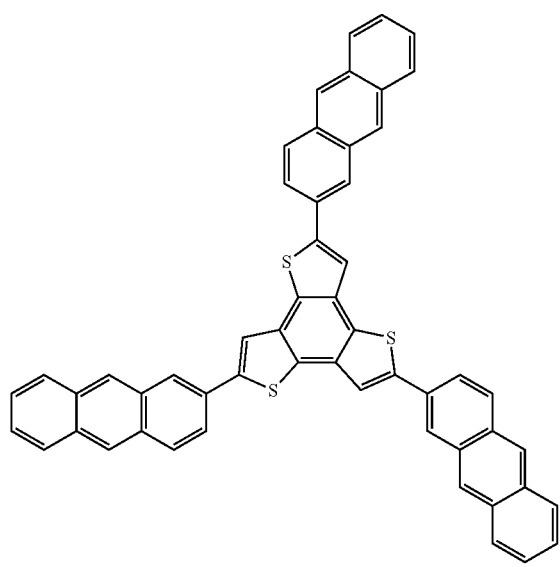
1006
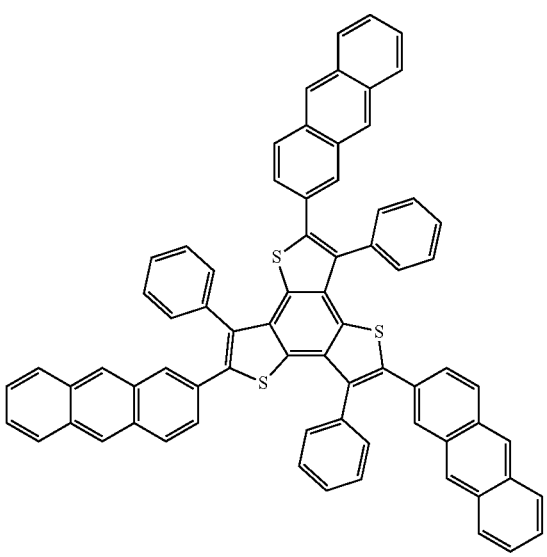

-continued
1007
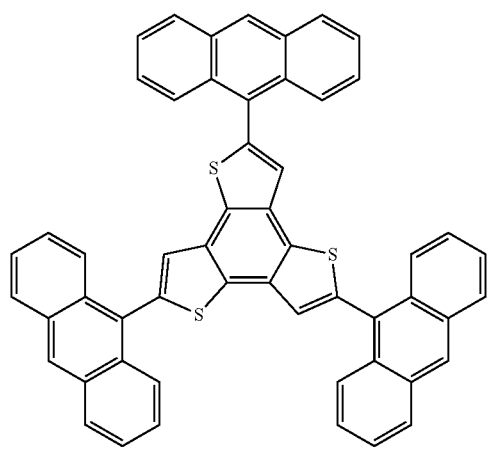
1008
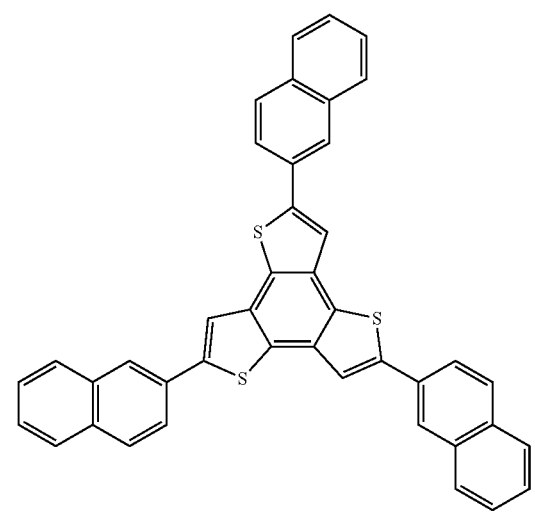
1009
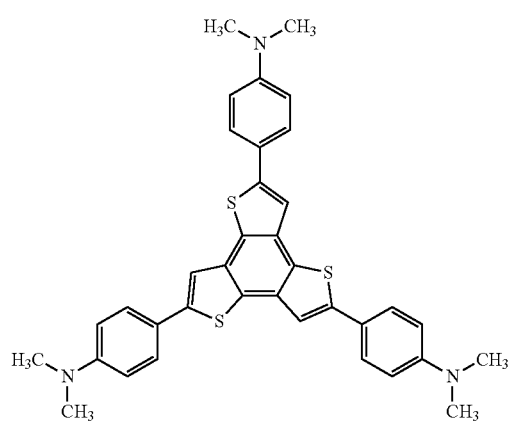
1010
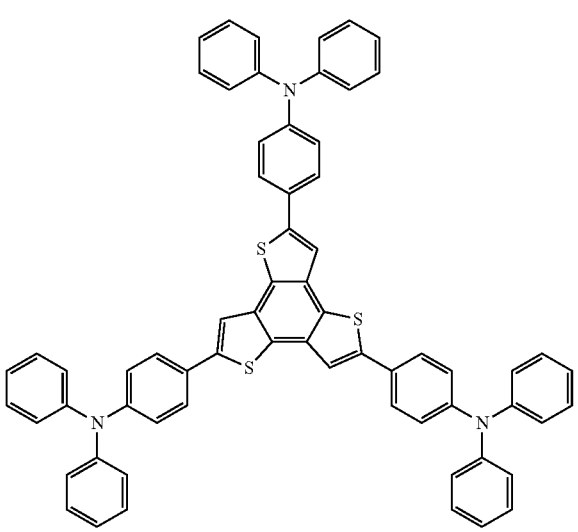
1011
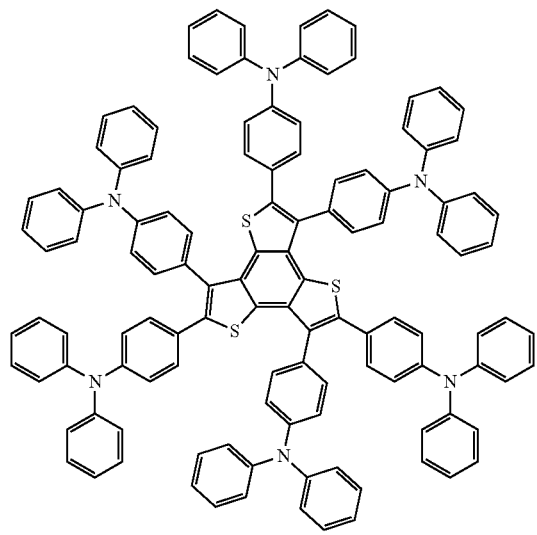
1012
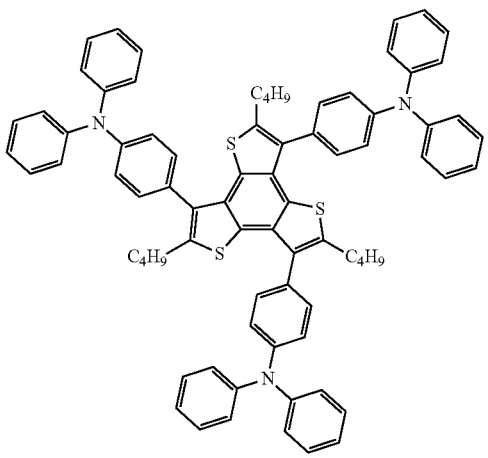

-continued
1013
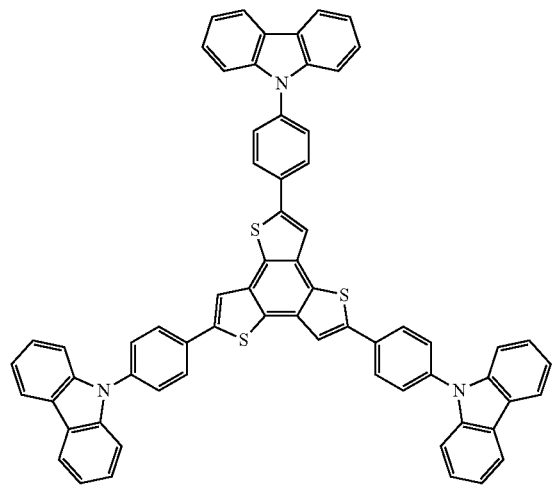
1014
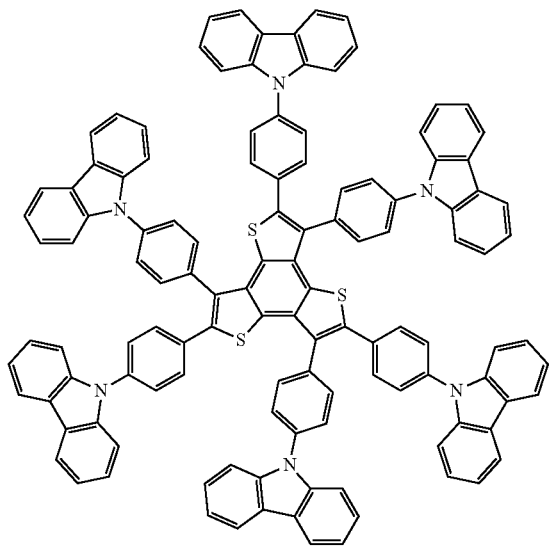
1015
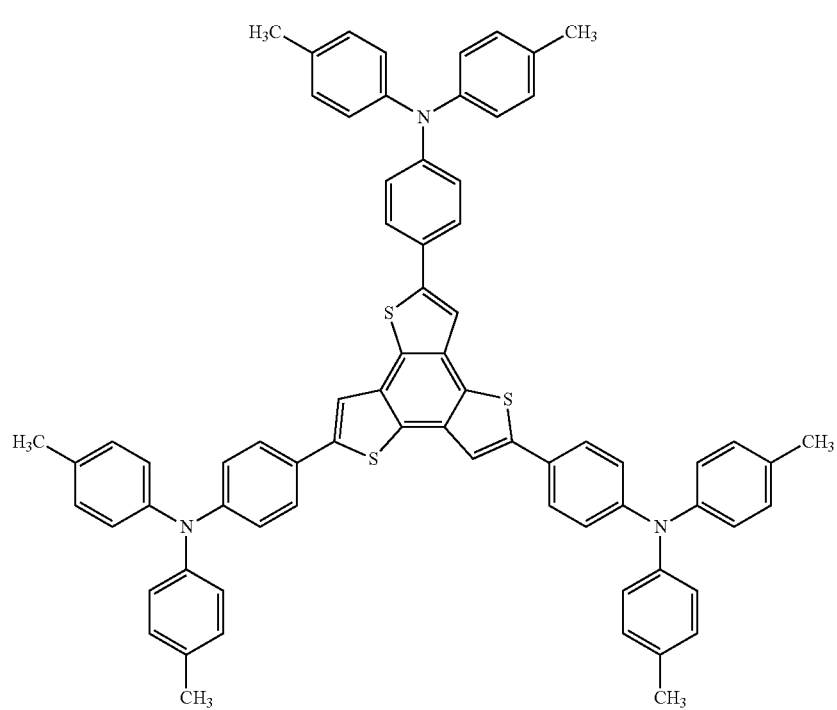

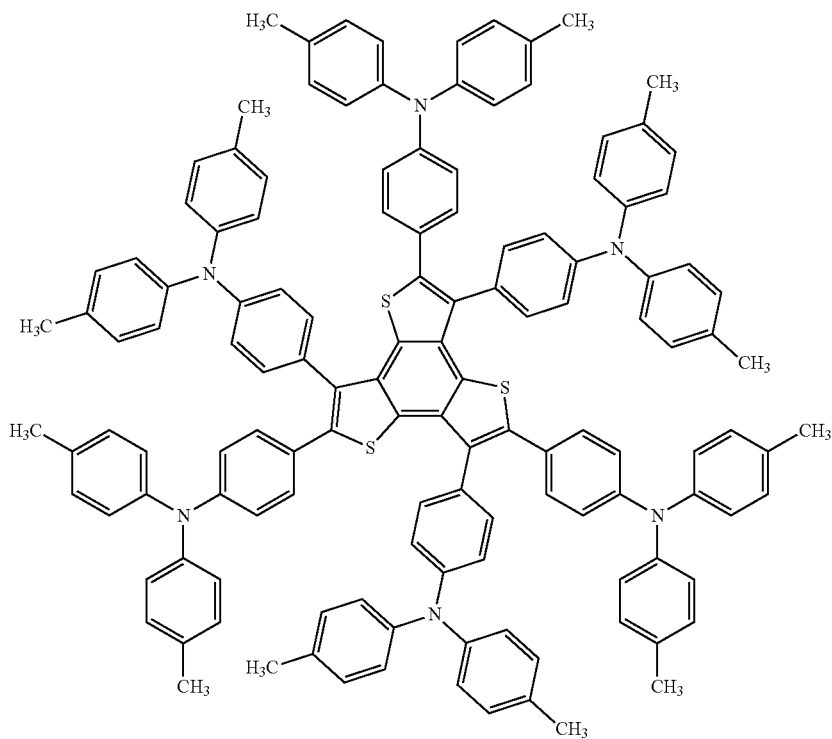
1016
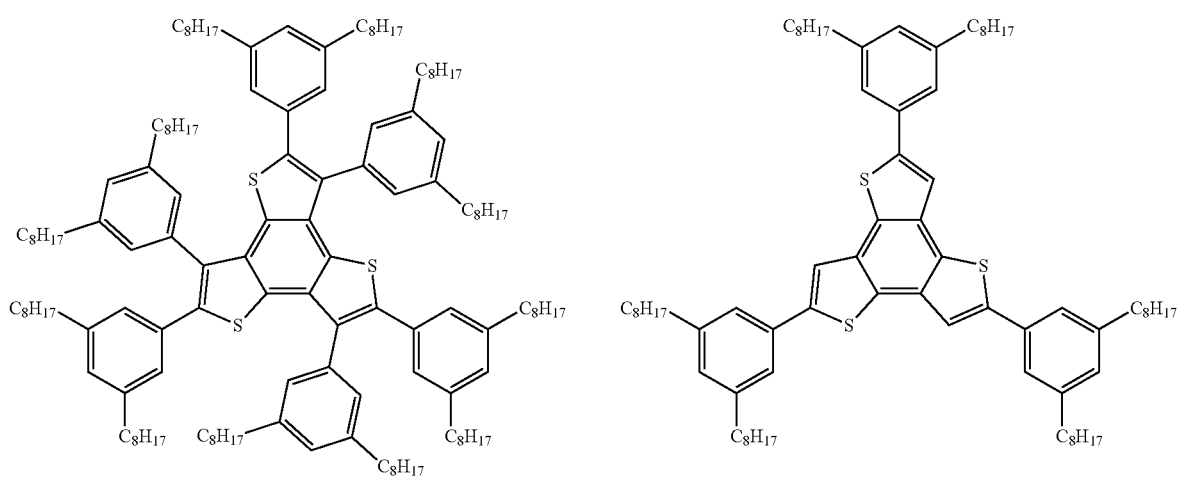
1017
1018

-continued
1019
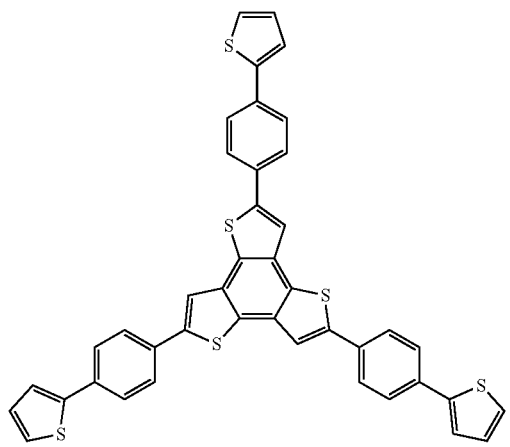
1020
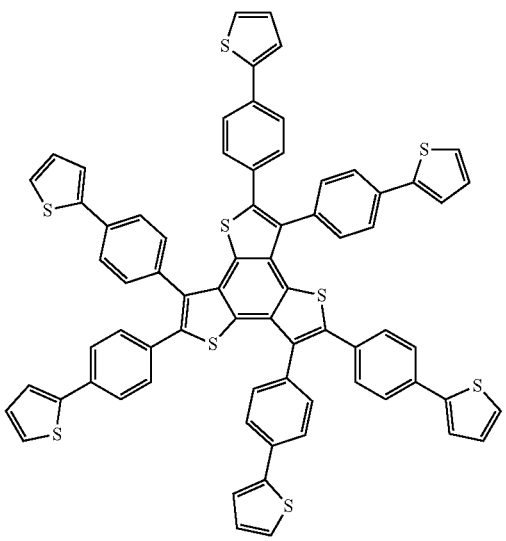
1021
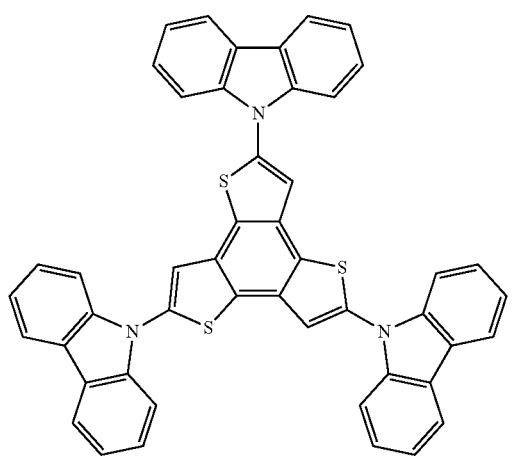
1022
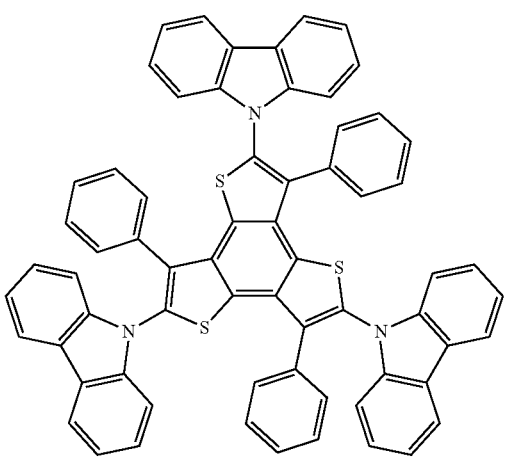
1023
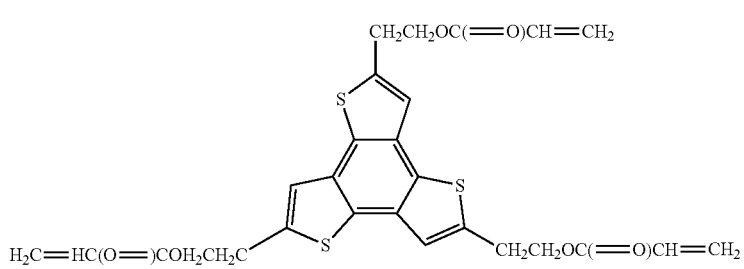
1024
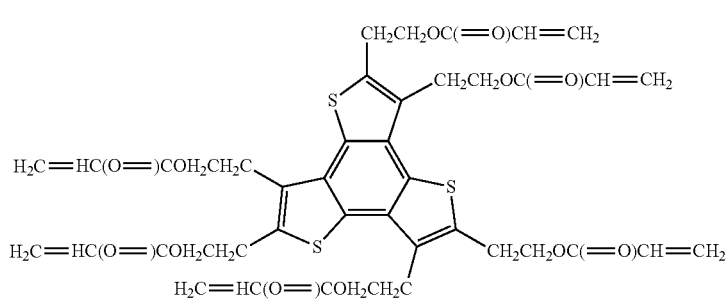

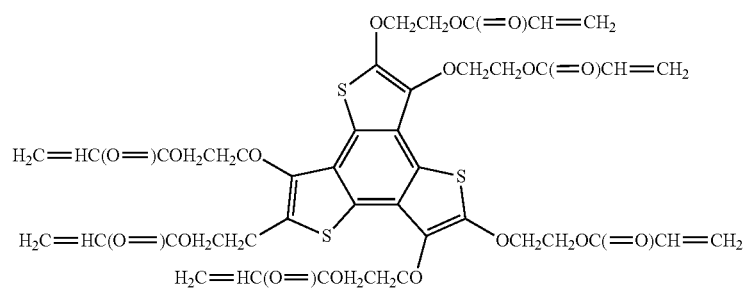
1025
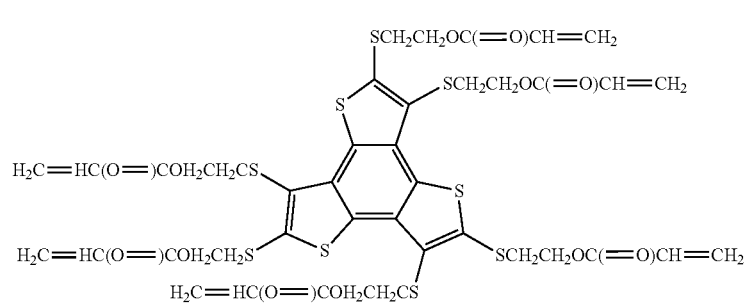
1026
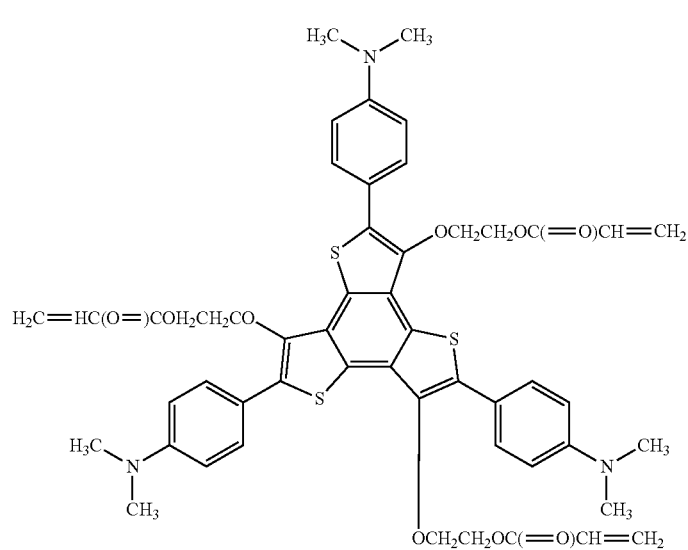
1027

-continued

1028

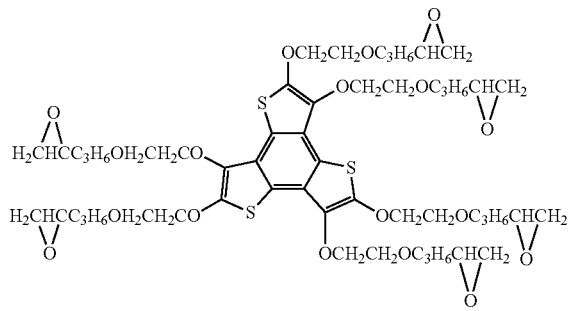

1029

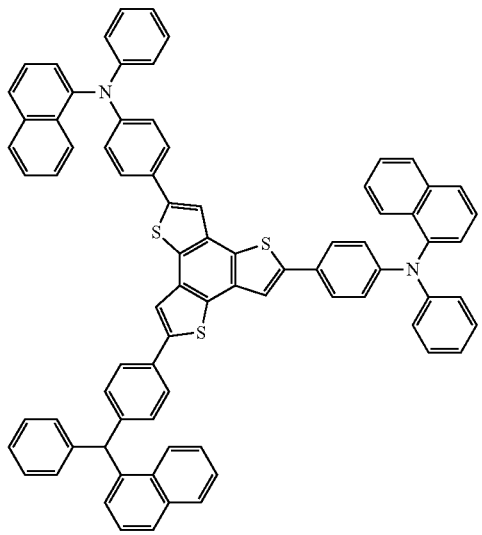

A heterocyclic compound represented by formula (1) of the present invention can be used together with a solvent and (or) a binder in the form of a composition.

As the solvent, any solvent can be used as long as it dissolve or disperse an organic semiconductor material and a polymer compound and it is present in the state of liquid within a proper temperature range. Specific examples of the solvent include, but are not limited to, benzene, toluene, xylene, mesitylene, monochlorobenzene, dichlorobenzene, trichlorobenzene, tetrachlorobenzene, tetrahydrofuran, methylene chloride, chloroform, ether, hexane, cyclohexane, heptane, acetonitrile, acetone, cyclopentanone, cyclohexanone, 2-butanone, 2,4-dimethyl-3-pentanone, ethyl acetate, 1-butanol, fluorobenzene, 1,2-dimethoxyethane, methyl naphthalene, decalin and tetrahydronaphthalene. These solvents can be used singly or in arbitral combination of two types or more.

The binder is, a polymer compound and, if necessary, a mixture of various other low molecular weight compounds and additives. The polymer compound refers to a macromolecule formed of an extremely large number of atoms via chemical bonds. A polymer having a structural unit such as a monomer repeat is included in the polymer compound. Generally, a compound having a molecular weight of about 10,000 or more is regarded as a polymer compound; however, in a broad sense, a polymer having a low molecular weight called an oligomer is also referred to as a polymer compound. The polymer compound of the present invention includes not only a compound having a large molecular weight as mentioned above but also a polymer having a relatively low molecular weight.

The binder of the present invention is a solid substance at room temperature, and preferably a polymer compound dissolved in a solvent. The specific polymer compounds used in the present invention are roughly classified into a synthetic organic polymer compounds, naturally occurring organic polymer compounds and inorganic polymer compounds. Specific examples include the following compounds and derivatives thereof, copolymers and mixtures of these. All polymer compounds described below can be used singly or in an arbitrary combination of two or more types.

Examples of synthetic organic polymer compound include a synthetic resin, plastic, a polyvinyl chloride polymer, a polyethylene polymer, a phenolic resin polymer, a polystyrene polymer, an acrylic resin polymer, an amide resin polymer, an ester resin polymer, a nylon polymer, a vinylon polymer, a polyethylene terephthalate polymer, a synthetic rubber polymer, a polyisoprene polymer, an acryl rubber polymer, an acrylonitrile rubber polymer and a urethane rubber polymer. Preferable examples thereof include a synthesis resin, a plastic, a polyvinyl chloride polymer, a polyethylene polymer, a phenolic resin polymer, a polystyrene polymer, an acrylic resin polymer, an amide resin polymer, an ester resin polymer, a nylon polymer, a vinylon polymer and a polyethylene terephthalate polymer. Further preferable examples thereof include a synthesis resin, a plastic, a polyvinyl chloride polymer, a polystyrene polymer, a polyethylene polymer, a phenolic resin polymer and an acrylic resin polymer.

Examples of the naturally occurring organic polymer include cellulose, starch and natural rubber. Cellulose and starch are more preferable.

Examples of the inorganic polymer compound include a silicone resin and a silicone rubber.

When these polymer compounds are classified in view of electric characteristics, they are roughly divided into conductive polymer compounds, semiconductor polymer compounds and insulating polymer compounds.

The conductive polymer compounds refer to polymer compounds characterized by having a developed π electron skeleton in the molecule and exhibiting electric conductivity. Specific examples of the conductive polymer compounds include a polyacetylene polymer, a polydiacetylene polymer, a polyparaphenylene polymer, a polyaniline polymer, a polythiophene polymer, a polypyrrole polymer, a polyparaphenylenevinylene polymer, a polyethylene dioxythiophene polymer, a polyethylenedioxythiophene/polystyrene sulfonic acid mixture (generic name: PEDOT-PSS), nucleic acid and derivatives of these. Most of them are improved in conductivity by doping. Of these conductive polymer compounds, a polyacetylene polymer, a polyparaphenylene polymer, a polyaniline polymer, a polythiophene polymer, a polypyrrole polymer and a polyparaphenylenevinylene polymer are more preferable.

The semiconductor polymer compounds refer to polymer compounds characterized by exhibiting a semiconductor property. Specific examples of the semiconductor polymer compounds include a polyacetylene polymer, a polydiacetylene polymer, a polyparaphenylene polymer, a polyaniline polymer, a polythiophene polymer, a polypyrrole polymer, a polyparaphenylenevinylene polymer, a polyethylenedioxythiophene polymer, nucleic acid and derivatives of these. Specific examples thereof that are more preferable include a polyacetylene polymer, a polyaniline polymer, a polythiophene polymer, a polypyrrole polymer and a polyparaphenylenevinylene polymer. The semiconductor polymer compound exhibits conductivity by doping and sometimes exhibits conductivity depending upon the amount of dopant.

The insulating polymer compounds are polymer compounds characterized by exhibiting insulating properties. Most of the polymer compounds except the conductive or semiconductor polymer compounds are insulating polymer compounds. Specific examples of these that are more preferable include an acryl polymer, a polyethylene polymer, a polymethacrylate polymer, a polystyrene polymer, a polyethylene terephthalate polymer, a nylon polymer, a polyamide polymer, a polyester polymer, a vinylon polymer, a polyisoprene polymer, a cellulose polymer, a copolymerization polymer and derivatives of these.

As long as the effect obtained by the composition of the present invention is maintained, other additives, for example, a carrier generator, a conductive substance, a viscosity moderator, a surface tension moderator, a leveling agent, a penetrating agent, a wet moderator and a rheology moderator may be appropriately added.

In the composition of the present invention, the content of a compound of formula (1) falls within the range of usually 0.01% to 95%, preferably 0.05% to 50% and more preferably 0.1% to 20%. The "%" is based on weight and unless otherwise specified, the same is applied hereinafter.

In the composition of the present invention, the content of a solvent falls within the range of usually 5% to 99.99%, preferably 50% to 99.95% and more preferably 80% to 99.9%.

In the composition of the present invention, a binder may or may not be used. When a binder is used, the content thereof suitably falls within the range of usually 1% to 500% and preferably 5% to 300% relative to the heterocyclic compound represented by the above formula (1).

In the composition of the present invention, other additives may or may not be used. When additives are used, the content thereof falls within the range of usually 0.1% to 100%, preferably 0.2% to 50% and more preferably 0.5% to 30% relative to the compound of formula (1).

The composition of the present invention can be prepared by dissolving or dispersing a heterocyclic compound represented by the above formula (1) and a binder in a solvent so as to satisfy, for example, the aforementioned contents and applying a heat treatment depending upon each solubility and stirring; however, a method for preparing the composition is not limited to this. Furthermore, as described above, the binder and other additives may or may not be used. When other additives are added as mentioned above, the additives are appropriately added so as not to leave insoluble components or insoluble components may be removed by a treatment such as filtration.

The thin film of the present invention refers to a thin film formed of a heterocyclic compound represented by the formula (1) of the present invention or a composition thereof. Although the film thickness of the thin film varies depending upon the use, it is usually 0.1 nm to 100 μm, preferably 0.5 nm to 30 μm and more preferably 1 nm to 20 μm.

Examples of a method for forming a thin film of the present invention generally include a vacuum process such as a resistance heating vapor deposition, an electron beam vapor deposition, a sputtering and a molecular stacking method; a solution process such as a spin coat method, a drop cast method, a dip coat method and a spray method; a relief printing method such as a flexo printing and a resin relief printing; a flat-plate printing method such as an offset printing method, a dry offset printing method, a pad printing method and a lithographic printing; an intaglio printing method such as gravure printing; a screen printing method such as a silk screen printing method, a mimeographic printing method and a lithograph printing method; an inkjet printing method and a micro contact print method and a combination method of these.

Usually a vacuum process such as resistance heating vapor deposition process and a solution process such as a spin coat process and a dip coat process, an inkjet process, screen printing, relief printing are preferable.

The organic electronics device of the present invention contains a heterocyclic compound represented by the above formula (1) as an electron material for use in electronics. Examples of the organic electronics device include a thin-film transistor, an organic EL device, a liquid crystal display, a photoelectric conversion device, an organic solar battery device and an organic semiconductor laser device. These will be more specifically described.

In order to use a heterocyclic compound represented by the formula (1) of the present invention as an active layer of a semiconductor such as a thin-film transistor device, an organic EL device and an organic semiconductor laser device, the heterocyclic compound must be an organic semiconductor compound exhibiting a semiconductor property.

First, the thin-film transistor will be more specifically described.

The thin-film transistor has two electrodes (source electrode and drain electrode) in contact with a semiconductor. The current flowing between the electrodes is controlled by voltage applied to another electrode called a gate electrode.

Generally, in the thin-film transistor device, a MIS (Metal-Insulator-Semiconductor) structure where a gate electrode is insulated by an insulating film is frequently used. The structure where a metal oxide film is used as the insulating film is called a MOS structure. Besides these, there is a structure where a gate electrode is formed via the Schottky barrier, that is, a MES structure. In the case of a thin-film transistor using an organic semiconductor material, the MIS structure is frequently used.

Hereinafter, referring to the drawings, the organic thin-film transistor of the present invention will be more specifically described; however, the present invention is not limited to these structures.

FIG. 1 shows some embodiments of the thin-film transistor (device) of the present invention. In each embodiment, reference numeral 1 represents a source electrode, 2 a semiconductor layer, 3 a drain electrode, 4 an insulating layer, 5 an gate electrode and 6 a substrate, respectively. The arrangement of individual layers and electrodes can be appropriately selected depending upon the use of the device. A to D are called a horizontal transistor substrate since current flows in a direction parallel to the substrate. A is called as a bottom contact structure and B is called as a top contact structure. Furthermore, C is a structure frequently used for forming an organic single crystalline transistor and having source and drain electrodes and an insulating layer provided on a semiconductor and further a gate electrode is formed thereon. D is a structure called a top & bottom contact type transistor. E is a schematic view of a transistor having a vertical structure, that is, a static induction transistor (SIT). In the SIT, since current flow spreads in a plane, a large amount of carriers can migrate at a time. Since a source electrode and a drain electrode are arranged vertically, the distance between the electrodes can be reduced. As a result, a response is made at a high speed. Accordingly, SIT can be preferably applied to uses for supplying a large amount of current and for switching at a high speed. In FIG. 1E, a substrate is not shown; however, usually a substrate is provided outside the source and drain electrodes represented by reference numerals 1 and 3, respectively, in FIG. 1E.

Individual structural elements in each embodiment will be described.

It is necessary for a substrate 6 to hold the layers to be formed thereon without being removed. Examples of the substrate that can be used include an insulating material such as a resin plate, a film, paper, glass, quartz and ceramic; a conductive substrate formed of e.g., a metal and an alloy and having an insulating layer formed thereon by coating; and a material formed of a resin and an inorganic material in various combinations. Examples of the resin film that can be used include polyethylene terephthalate, polyethylene naphthalate, polyethersulfone, polyamide, polyimide, polycarbonate, cellulose triacetate and polyether imide. When a resin film and paper is used, flexibility can be imparted to a device. The device becomes flexible and light and practical performance thereof is improved. The thickness of the substrate is usually 1 µm and preferably 5 µm to 5 mm.

In the source electrode 1, drain electrode 3 and gate electrode 5, a material having conductivity is used. Example thereof that can be used include a metal such as platinum, gold, silver, aluminium, chromium, tungsten, tantalum, nickel, cobalt, copper, iron, lead, tin, titanium, indium, palladium, molybdenum, magnesium, calcium, barium, lithium, potassium and sodium and alloys containing these; a conductive oxide such as $InO_2$, $ZnO_2$, $SnO_2$ and ITO; a conductive polymer compound such as polyaniline, polypyrrole, polythiophene, polyacetylene, polyparaphenylene, vinylene and polydiacetylene; semiconductors such as silicon, germanium and gallium arsenic; and a carbon material such as carbon black, fullerene, carbon nanotube and graphite. Furthermore, the conductive polymer compound and semiconductor may have a dopant. Examples of the dopant include an inorganic acid such as hydrochloric acid and sulfuric acid; organic acids having an acidic functional group such as sulfonic acid; a lewis acid such as $PF_5$, $AsF_5$ and $FeCl_3$; a halogen atom such as iodine; and a metal atom such as lithium, sodium and potassium. Boron, phosphorus and arsenic are frequently used as a dopant for an inorganic semiconductor such as silicon. Furthermore, a composite material having carbon black and a metal particle dispersed in the dopant is also used.

Furthermore, the distance (channel length) between the source and drain electrodes is an important factor for determining the characteristics of a device. The channel length is usually 0.1 to 300 µm and preferably 0.5 to 100 µm. If the channel length is short, the amount of current increases; however, conversely, leak current generates. Therefore, a proper channel length is required. The width (channel width) between the source and drain electrode is usually 10 to 10000 µm and preferably 100 to 5000 µm. Furthermore, a further longer channel width can be formed by employing a comb structure as the structure of the electrode. An appropriate length can be selected depending upon a requisite amount of current and the structure of a device.

The structures (shape) of source and drain electrodes each will be described. Even if the structures of the source and drain electrodes are the same or different. In the case of a bottom contact structure, generally each of the electrodes is preferably formed into a rectangular solid by a lithographic method. The length of the electrode may be the same as the channel width (mentioned above). The width of the electrode is not particularly defined; however the shorter the width, the more preferable in order to reduce the area of a device as long as electric characteristics can be stabilized. The width of the electrode is usually 0.1 to 1000 µm and preferably 0.5 to 100 µm. The thickness of the electrode is usually 0.1 to 1000 nm, preferably 1 to 500 nm and more preferably 5 to 200 nm. To the electrodes 1, 3, 5, wiring is connected. The wiring is formed from substantially the same materials as used in the electrodes.

As the insulating layer 4, a material having an insulating property is used. Examples thereof that can be used include polymers such as polyparaxylylene, polyacrylate, polymethyl methacrylate, polystyrene, polyvinyl phenol, polyamide, polyimide, polycarbonate, polyester, polyvinyl alcohol, polyvinyl acetate, polyurethane, polysulfone, epoxy resin and phenolic resin and copolymers of these in combination; metal oxides such as silicon dioxide, aluminum oxide, titanium oxide and tantalum oxide; ferroelectric metal oxides such as $SrTiO_3$ and $BaTiO_3$; nitrides such as silicon nitride and aluminum nitride; sulfides; and dielectric substances such as a fluoride; or a polymer having particles of a dielectric substance dispersed therein. The film thickness of the insulating layer 4 varies depending upon the material, however, it is usually 0.1 nm to 100 µm, preferably 0.5 nm to 50 µm and more preferably 1 nm to 10 µm.

As the material for the semiconductor layer 2, a heterocyclic compound represented by the formula (1) of the present invention or a composition thereof is used. The compound or a composition thereof is used to form a semiconductor layer 2 as a thin film by the method previously described. To improve the characteristics of a thin-film transistor and impart other characteristics, if necessary, other organic semiconductor materials and various types of additives may be added. Furthermore, the semiconductor layer 2 may be formed of a plurality of layers.

In the thin-film transistor of the present invention, at least one of heterocyclic compounds represented by the above formula (1) is used as an organic semiconductor material. A thin film is formed by using a heterocyclic compound represented by the above formula (1) and a composition thereof. When a solvent is used in the composition, the composition can be used after the solvent is substantially evaporated. When an organic semiconductor layer is formed by the vapor deposition method described later, it is particularly preferable that a single compound is used as an organic semiconductor material rather than a mixture of a plurality of heterocyclic compounds represented by the formula (1). However, as described above, e.g., for improving the characteristics of a transistor, addition of additives such as a dopant is not interrupted. The case where a semiconductor layer is formed by a solution process is not limited to this.

The additives mentioned above may be added within the range of usually 0.01 to 10 wt %, preferably 0.05 to 5 wt % and more preferably 0.1 to 3 wt % based on the total amount of organic semiconductor material as 1.

Furthermore, the semiconductor layer may consist of a plurality of layers; however, it is more preferably a single-layer structure. The thinner the film thickness of the semiconductor layer 2, the more preferable, as long as a requisite function is maintained. This is because, in the horizontal thin-film transistor as shown in A, B and D, the characteristics of the device do not depend upon the film thickness as long as the film has a predetermined thickness or more; on the other hand, when the film thickness increases, leakage current often increases. The film thickness of a semiconductor layer for exerting a requisite function is usually 1 nm to 10 μm, preferably 5 nm to 5 μm, and more preferably 10 nm to 3 μm.

To the thin-film transistor of the present invention, for example, between the substrate layer and the insulating film layer, between the insulating film layer and the semiconductor layer, and the outer surface of a device, if necessary, another layer may be provided. For example, when a protective layer is formed on the organic semiconductor layer directly or via another layer, the effect of the ambient air such as humidity can be reduced. Furthermore, the ON/OFF ratio of the device can be increased. Likewise, electric characteristics can be advantageously stabilized.

Examples of the material for the protective layer that is preferably used include, but are not particularly limited to, films formed of various types of resins such as an epoxy resin, an acrylic resin such as polymethyl methacrylate, polyurethane, polyimide, polyvinyl alcohol, fluorine resin and polyolefin; inorganic oxide films formed of e.g., silicon oxide, aluminum oxide and silicon nitride; and films formed of a dielectric substance such as a nitride film. Particularly, a resin (polymer) having small oxygen and water transmissivities and a small coefficient of water absorption is preferable. Recently, a protective material developed for an organic EL display can be used. The film thickness of the protective layer can be arbitrarily selected depending upon the purpose thereof; however, it is usually 100 nm to 1 mm.

Furthermore, by previously applying a surface treatment to a substrate or an insulating layer on which an organic semiconductor layer is stacked, characteristics of a thin-film transistor device can be improved. For example, by controlling the hydrophilic/hydrophobic degree of a substrate surface, the quality of the film that is stacked thereon can be improved. Particularly, the organic semiconductor material may sometimes change in characteristics depending upon the state of the film such as molecular orientation. Therefore, when a surface treatment is applied to e.g., a substrate, the molecular orientation of an interface portion between e.g., the substrate and the organic semiconductor layer to be formed later is controlled and the number of trap sites on the substrate and the insulating layer is reduced. As a result, characteristics such as a carrier mobility are conceivably improved.

The trap site refers to a functional group such as a hydroxy group present in an untreated substrate. If such a functional group is present, electrons are attracted to the functional group, with the result that carrier mobility reduces. Therefore, it is often effective to reduce the number of trap sites for improving characteristics such as carrier mobility.

Examples of the substrate treatment for improving characteristics as mentioned above include a hydrophobic treatment with e.g., hexamethyldisilazane, cyclohexene, octyltrichlorosilane and octadecyltrichlorosilane; an acid treatment with e.g., hydrochloric acid, sulfuric acid and acetic acid; an alkali treatment with e.g., sodium hydroxide, potassium hydroxide, calcium hydroxide and ammonia; an ozone treatment; a fluorination treatment; a plasma treatment with e.g., oxygen and argon; a treatment by forming a Langmuir-Blodgett film; a treatment by forming a thin film of another insulating material or semiconductor thin film; a mechanical treatment; an electric treatment such as corona discharge; and a rubbing treatment using a fiber.

In these embodiments, for example, a method of forming each of the substrate layer and the insulating film layer, and the insulating film layer and the organic semiconductor layer, for example, a vacuum vaporization method, a sputter method, a coating method, a printing method and a sol-gel method are appropriately employed.

Next, a method for manufacturing the thin-film transistor device according to the present invention will be described, taking a bottom contact type thin-film transistor shown in FIG. 1, embodiment example A, as an example, and based on FIG. 2. The manufacturing method can be similarly applied to e.g., the thin-film transistor of another embodiment as mentioned above.

(Re: Substrate of Thin-Film Transistor and Substrate Treatment)

Figure 2:
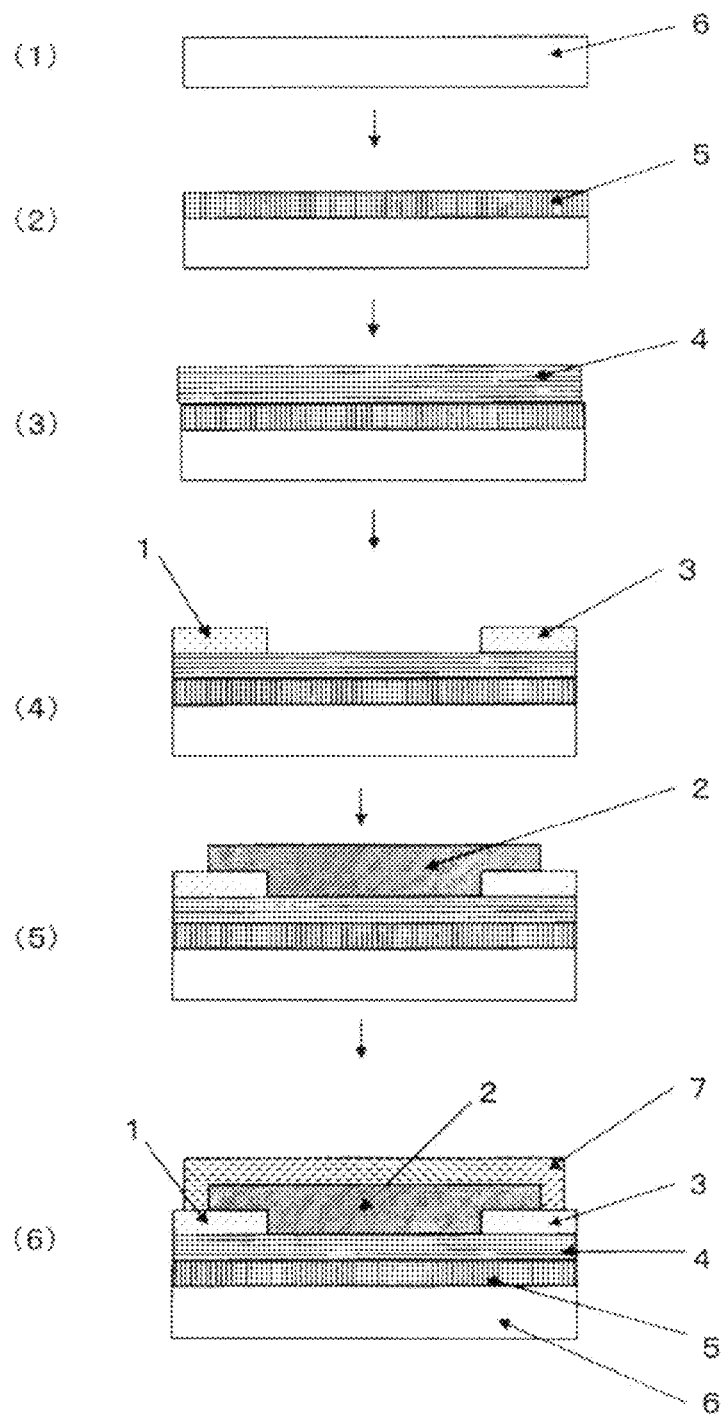
FIG. 2 a schematic view showing steps of manufacturing an embodiment of a thin-film transistor of the present invention.

The thin-film transistor of the present invention is formed by providing a various requisite layers and electrodes on the substrate 6 (see FIG. 2 (1)). As the substrate, the aforementioned materials can be used. Onto the substrate, e.g., the aforementioned surface treatments can be applied. The thinner the thickness of the substrate 6, the more preferable, as long as a requisite function is maintained. Although the thickness varies depending upon the material, it is usually 1 μm to 10 mm and preferably 5 μm to 5 mm. Furthermore, if necessary, a substrate may have a function of an electrode.

(Re: Formation of Gate Electrode)

The gate electrode 5 is formed on the substrate 6 (see FIG. 2 (2)). The aforementioned materials can be used as the electrode material. An electrode film can be formed using various methods. Examples thereof that can be employed include a vacuum vaporization method, a sputter method, a coating method, a hot printing method, a printing method and a sol-gel method. During or after film formation, if necessary, it is preferable that patterning is performed so as to have desired shape. Patterning can be performed using various methods, including a photolithographic method in which patterning and etching of a photoresist are combined. Furthermore, patterning can be performed using a printing method such as an inkjet printing, a screen printing, an offset printing and a relief printing; a soft lithographic method such as a micro contact printing method, and a combination method of these methods. The film thickness of the gate electrode 5 varies depending upon the material; however, it is usually 0.1 nm to 10 μm, preferably 0.5 nm to 5 μm and more preferably 1 nm to 3 μm. Furthermore, when a gate electrode also serves as a substrate, the film thickness may be larger than the aforementioned one.

(Re: Formation of the Insulating Layer)

The insulating layer 4 is formed on the gate electrode 5 (see FIG. 2 (3)). As an insulating material, e.g., the insulating materials described above can be used. In forming the insulating layer 4, various methods may be used. Examples thereof include a coating method such as spin coating, spray coating, dip coating, casting, bar coating and blade coating; a printing method such as a screen printing, an offset printing, an inkjet; and a dry process such as a vacuum vaporization method, a molecular beam epitaxial growth method, an ion cluster beam method, an ion plating method, a sputtering method, an atmospheric pressure plasma method and a CVD method. Other than these, e.g., a sol-gel method and a method of forming an oxide film on a metal, such as alumite on aluminum and silicon dioxide on silicon can be employed. Note that, at the site at which the insulating layer and the semiconductor layer are into contact with each other, in order to satisfactorily orient molecules constituting a semiconductor at the interface between both layers, e.g., molecules of a heterocyclic compound represented by the formula (1), a predetermined surface treatment may be applied to the insulating layer. As the surface treatment method, the same surface treatment applied to a substrate can be used. The thinner the film thickness of the insulating layer 4, the more preferable, as long as the function thereof is maintained. The film thickness is usually 0.1 nm to 100 µm, preferably 0.5 nm to 50 µm and more preferably 5 nm to 10 µm.

(Formation of Source Electrode and Drain Electrode)

The source electrode 1 and drain electrode 3 may be formed in accordance with e.g., a method for forming the gate electrode 5 (see FIG. 2 (4)). Various additives can be used to reduce contact resistance with the organic semiconductor layer.

(Formation of Organic Semiconductor Layer)

As the organic semiconductor material, as described above, a heterocyclic compound represented by the formula (1) or a composition thereof can be used. A film of an organic semiconductor layer can be formed using various methods, which are roughly divided into a vacuum-process formation method such as a sputtering method, a CVD method, a molecular beam epitaxial growth method and a vacuum vaporization method; a coating method such as a dip coat method, a die coater method, a roll coater method, a bar coater method and a spin coat method; and a solution-process formation method such as an inkjet method, a screen printing method, an offset printing method and a micro contact printing method.

When a heterocyclic compound represented by the above formula (1) of the invention of the present application is used as an organic semiconductor material to form an organic semiconductor layer, a method for forming the organic semiconductor layer by a solution process such as printing and a vacuum process is mentioned.

First, a method for obtaining an organic semiconductor layer by forming a film of an organic semiconductor material by a vacuum process will be described. An organic semiconductor material as mentioned above is heated in a crucible or a metal boat under vacuum, and vapor of the organic semiconductor material is attached (deposited) (vapor deposition) on a substrate (insulating layer, an exposed portions of the source electrode and drain electrode). Such a method, that is, a vacuum vaporization method, is preferably employed. At this time, a vacuum degree is usually $1.0 \times 10^{-1}$ Pa or less and preferably $1.0 \times 10^{-3}$ Pa or less. Furthermore, depending upon the temperature of a substrate during the vapor deposition, characteristics of the organic semiconductor film and further a thin-film transistor sometimes change. Therefore, it is preferable to select substrate temperature carefully. The substrate temperature during the vapor deposition is usually 0 to 200° C., preferably 10 to 150° C., more preferably 15 to 120° C., further preferably 25 to 100° C. and particularly preferably 40 to 80° C.

Furthermore, the vapor deposition rate is usually 0.001 nm/second to 10 nm/second and preferably 0.01 nm/second to 1 nm/second. The film thickness of the organic semiconductor layer formed of an organic semiconductor material is usually 1 nm to 10 µm, preferably 5 nm to 5 µm and more preferably 10 nm to 3 µm.

Note that in place of the vapor deposition method for forming an organic semiconductor layer by heating and evaporating an organic semiconductor material and depositing on a substrate, a sputtering method, in which accelerated ions such as argon is bombarded to a material target to eject atoms from the material and deposited onto a substrate, may be employed.

Next, a method for obtaining an organic semiconductor layer by forming a film by a solution process will be described. A heterocyclic compound represented by the formula (1) of the present invention is dissolved in e.g., a solvent. Furthermore, the resultant solution, if necessary, a composition having a binder added thereto, is applied to a substrate (insulating layer, exposed portions of a source electrode and a drain electrode). Examples of a coating method that can be employed include a coating method such as casting, spin coating, dip coating, blade coating, wire-bar coating and spray coating; a printing method such as inkjet printing, screen printing, offset printing and relief printing, and a soft lithographic method such as micro contact printing, and further, a combination method of these methods.

Furthermore, as an analogous method to a coating method, e.g., the Langmuir-Blodgett method in which a monomolecular film of an organic semiconductor layer is formed by adding ink as mentioned above onto a water surface dropwise and transferred to a substrate to stack it and a method of sandwiching a liquid crystal or a molten material with two substrates or introducing it between the substrates by capillary action, can be employed.

An environment such as the temperature of a substrate and a composition during film formation time is important. Since characteristics of a transistor are sometimes changed by the temperature of a substrate and a composition, it is preferable that the temperature of a substrate and a composition is carefully selected. The substrate temperature during the vapor deposition is usually 0 to 200° C., preferably 10 to 120° C. and more preferably 15 to 100° C. Since the characteristics of the transistor vary depending upon the solvent used in the composition, particular attention should be given.

The thinner the film thickness of the organic semiconductor layer formed by this method, the more preferable, as long as the function is maintained. When the film thickness increases, a risk of leakage current may increase. The film thickness of the organic semiconductor layer is usually 1 nm to 10 µm, preferably 5 nm to 5 µm and more preferably 10 nm to 3 µm.

The organic semiconductor layer thus formed (see FIG. 2 (5)) can be further improved in characteristics by a post treatment. For example, it is considered that distortion in a film produced during film formation time is mitigated, the number of e.g., pin holes is reduced and alignment and orientation of a film can be controlled by a heat treatment. Consequently, an organic semiconductor property can be improved and stabilized. When the thin-film transistor of the present invention is manufactured, it is effective to apply such a heat treatment in order to improve the property. The heat treatment is performed after the organic semiconductor layer is formed by heating the substrate. The temperature of the heat treatment is not particularly limited; however, it is usually from room temperature to about 150° C., preferably from 40 to 120° C. and further preferably from 45 to 100° C. The time for the heat treatment is not particularly limited; however, it is usually from 1 minute to 24 hours and preferably about 2 minutes to 3 hours. The atmosphere herein may be air or an atmosphere of an inert gas such as nitrogen or argon.

As other post treatment method for an organic semiconductor layer, there is a treatment with e.g., an oxidizable or reducible gas such as oxygen or hydrogen and a treatment with an oxidizable or reducible liquid. The property change is inducible by oxidation or reduction. This is often employed e.g. in order to increase or reduce carrier density in a film.

Furthermore, the property of the organic semiconductor layer can be changed by a process called doping, i.e., by adding a small amount of element, atomic group, molecule, polymer to an organic semiconductor layer. Examples thereof that can be doped include an acid such as oxygen, hydrogen, hydrochloric acid, sulfuric acid and sulfonic acid; a lewis acid such as $PF_5$, $AsF_5$ and $FeCl_3$; a halogen atom such as iodine; and a metal atom such as sodium and potassium. This can be attained by bringing these gases into contact with an organic semiconductor layer, soaking an organic semiconductor layer in a solution or applying an electrochemical doping treatment. These doping processes may not be performed after formation of an organic semiconductor layer. A dopant may be added during synthesis of the organic semiconductor compound. Alternatively, in a process where an organic semiconductor layer is formed by using ink for forming an organic semiconductor device, a dopant can be added to the ink or in a step of forming a thin film. Furthermore, codeposition may be made by adding a material for use in doping to a material for forming an organic semiconductor layer at the vapor deposition process. Furthermore, a doping material is mixed with an ambient atmosphere when an organic semiconductor layer is formed (an organic semiconductor layer is formed under an ambient atmosphere containing a doping material). Furthermore, ions can be accelerated in vacuum and bombarded to a film, thereby doping them into a film.

Examples of the effect of these doping processes include a change in electric conductivity due to an increase or decrease of a carrier density, a change in polarity of carrier (p-type, n-type) and a change in the Fermi level. Such doping is frequently used particularly in a semiconductor device using an inorganic material such as silicon.

(Re: Protective Layer)

Formation of a protective layer 7 on an organic semiconductor layer is advantageous since the ambient atmospheric effect can be minimized and electric characteristics of an organic thin-film transistor can be stabilized (see FIG. 2 (6)). A material for the protective layer, a material as mentioned above is used. As the film thickness of the protective layer 7, any film thickness may be employed depending upon the purpose; however, it is usually 100 nm to 1 mm.

Various methods can be employed in forming a film of the protective layer. When a protective layer is formed of a resin, for example, a method of applying a resin solution and drying it to form a resin film; and a method of applying or depositing a resin monomer and then polymerizing it may be mentioned. After the film is formed, a crosslinking treatment may be applied. When a protective layer is formed of an inorganic material, for example, a formation method performed in a vacuum process, such as a sputtering method and a vapor deposition method and a formation method performed in a solution process such as a sol-gel method can be used.

In the thin-film transistor of the present invention, a protective layer can be provided not only on the organic semiconductor layer but also between individual layers, if necessary. These layers are sometimes helpful to stabilize electric characteristics of a thin-film transistor.

According to the present invention, since a heterocyclic compound represented by the above formula (1) is used as an organic semiconductor material, manufacturing can be made in a relatively low temperature process. Therefore, a flexible material, such as a plastic plate and a plastic film, which has not been used under conditions exposed to high temperature, can be used as a substrate. As a result, an irrefrangible device of a light weight having an excellent flexibility can be manufactured and can be used as e.g., a switching device of an active matrix of a display.

The thin-film transistor of the present invention can be used also as digital devices and analog devices such as a memory circuit device, a signal driver circuit device and a signal processing circuit device. Furthermore, they are used in combination to form IC cards and IC tags. Furthermore, the thin-film transistor of the present invention, since characteristics thereof can be changed by external stimulation such as a chemical substance, can be used an FET sensor.

Next, organic EL device of the present invention will be more specifically described.

An organic EL device is a solid and can be used in application such as a self-luminous large-area color display and lighting. Since these points have attracted attention, numerous developments have been made. As a structure of the organic DL device, the following structures are known: a structure formed of opposed electrodes consisting of cathode and an anode, between which two layers, i.e., a light emitting layer and a charge transport layer are present; a structure formed of opposed electrodes between which a laminate of three layers, i.e., an electron transport layer, a light emitting layer and a hole transport layer, are present; a structure formed of opposed electrodes between which three layers or more are present. A structure having a light emitting layer formed of a single layer is also known.

The hole transport layer herein has a function of injecting holes from the anode and transporting the holes to a light emitting layer, thereby facilitating injection of holes to the light emitting layer and a function of blocking electrons. Furthermore, the electron transport layer has a function of injecting electrons from the cathode, transporting the electrons to a light emitting layer, thereby facilitating injection of the electrons into the light emitting layer and a function of blocking holes. Furthermore, in the light emitting layer, the electrons and holes separately injected are reunited to generate excitons. Energy is emitted in the process where the excitons radiate and lose activity. This energy is detected as emission of light. Now, preferable embodiments of the organic EL device of the present invention will be described below.

The organic EL device of the present invention is a device having a single or a plurality of organic thin films between anode and cathode electrodes, and emitting light by electric energy.

The anode that can be used in the organic EL device of the present invention is an electrode having a function of injecting holes into a hole injection layer, a hole transport layer and a light emitting layer. Generally, a metal oxide, a metal, an alloy and a conductive material having a work function of 4.5 eV or more are suitable. Examples thereof include, but are not particularly limited to, a conductive metal oxide such as tin oxide (NESA), indium oxide, indium tin oxide (ITO) and indium zinc oxide (IZO), a metal such as gold, silver, platinum, chromium, aluminium, iron, cobalt, nickel and tungsten, an inorganic conductive substance such as copper iodide and copper sulfide, a conductive polymer such as polythiophene, polypyrrole and polyaniline and carbon. Of these, ITO and NESA are preferably used.

The anode may be formed by using, if necessary, a plurality of materials and constituted of two layers or more. The resistance of the anode is not limited as long as a sufficient current for light emission of a device can be supplied; however, the resistance is preferably low in view of power consumption of the device. For example, if an ITO substrate has a sheet resistance of 300Ω/□ or less, it functions as a device electrode. However, since a substrate having about several Ω/□ can be supplied, it is desirable to use a low resistance product. The thickness of ITO can be arbitrarily selected in accordance with a resistance value; however, it is usually used in the range of between 5 and 500 nm and preferably between 10 and 300 nm. Examples of a method for forming a film such as ITO include a vapor deposition method, an electron beam method, a sputtering method, a chemical reaction method and a coating method.

The cathode that can be used in the organic EL device of the present invention is an electrode having a function of injecting electrons into an electron injection layer, an electron transport layer and a light emitting layer. Generally, a metal and an alloy having a low work function (about 4 eV or less) are suitable. Examples thereof include, but are not particularly limited to platinum, gold, silver, copper, iron, tin, zinc, aluminium, indium, chromium, lithium, sodium, potassium, calcium and magnesium. To improve device characteristics by increasing an electron injection efficiency, lithium, sodium, potassium, calcium and magnesium are preferable. As the alloy, an alloy including a metal having a low work function such as aluminium or silver can be used. Alternatively, these may be stacked to form the electrode structure. As the layered-structure electrode, an inorganic salt such as lithium fluoride can be used. Furthermore, when light is allowed to emitted not from the anode side but from the cathode side, a transparent film-electrode, which can be formed at low temperature, may be employed. Examples of a film-formation method include, but are not particularly limited to, a vapor deposition method, an electron beam method, a sputtering method, a chemical reaction method and a coating method. The resistance of the cathode is not limited as long as a sufficient current for light emission of a device can be supplied; however, the resistance is preferably low in view of power consumption of the device. That is, several hundreds to several $\Omega/\square$ is preferable. The film thickness to be used usually falls within the range of 5 to 500 nm and preferably 10 to 300 nm.

Furthermore, sealing and protection are made. A cathode is protected by an oxide or a nitride such as titanium oxide, silicon nitride, silicon oxide, silicon oxynitride and germanium oxide or a mixture of these, polyvinyl alcohol, vinyl chloride, a hydrocarbon polymer or a fluorine polymer and sealed with a dehydrating agent such as barium oxide, phosphorus pentoxide and calcium oxide.

Furthermore, to take out light emission, it is preferable to form an electrode on a substrate having a transparency generally within a light emission wavelength range of a device. Examples of the transparent substrate include a glass substrate and a polymer substrate. In the glass substrate, soda lime glass, non-alkali glass and quartz are used. The glass substrate may have a thickness sufficient to keep mechanical/thermal strength, preferably a thickness of 0.5 mm or more. As a material for glass, a material releasing a low amount of ions by solution is preferable. Non-alkali glass is rather preferable. For example of such glass, commercially available soda lime glass having a barrier coating such as $SiO_2$ can be used. Furthermore, examples of a substrate formed of a polymer except glass include polycarbonate, polypropylene, polyethersulfone, polyethylene terephthalate and acryl substrate.

In the organic EL device of the present invention, an organic thin film is formed of a single layer or a plurality of layers between anode and cathode electrodes. By adding a compound represented by the formula (1) to the organic thin film, a device emitting light due to electric energy can be obtained.

In the present invention, the "layer" of the single layer or a plurality of layers forming the organic thin film refers to a hole transport layer, an electron transport layer, a hole transport light emitting layer, an electron transport light emitting layer, a hole block layer, an electron block layer, a hole injection layer, an electron injection layer and a light emitting layer or a single layer having the functions possessed by these layers, as shown in the following structural example 9). In the present invention, examples of the structure of the layer forming the organic thin film include the following structural examples 1) to 9). Any one of the structures may be used.

Structural Examples

1) Hole transport layer/electron transport light emitting layer.

2) Hole transport layer/light emitting layer/electron transport layer.

3) Hole transport light emitting layer/electron transport layer.

4) Hole transport layer/light emitting layer/hole block layer.

5) Hole transport layer/light emitting layer/hole block layer/electron transport layer.

6) Hole transport light emitting layer/hole block layer/electron transport layer.

7) Structure formed by further adding a single hole injection layer before the hole transport layer or the hole transport light emitting layer in each of the combination of layers 1) to 6).

8) Structure formed by further adding a single electron injection layer before the electron transport layer or the electron transport light emitting layer in each of the combination of layers 1) to 7).

9) Structure having a single layer containing the mixture of the materials used in the combination of layers 1) to 8).

The structure 9) may be a single layer formed of materials generally called a bipolar light emitting material; or merely a single layer containing a light-emitting material, a hole transport material or an electron transport material. Generally, a multi-layer structure makes it possible to efficiently transport charges, in other words, holes and/or electrons, and reunite these charges. Furthermore, quenching of charges can be suppressed and thereby preventing stability of a device from decreasing, with the result that efficiency of light emission can be improved.

The hole injection layer and transport layer are formed by stacking a hole transport material alone or a mixture of two or more hole transport materials. Examples of the hole transport material that can be preferably used include a triphenyl amine such as N,N'-diphenyl-N,N'-di(3-methylphenyl)-4,4'-diphenyl-1,1'-diamine and N,N'-dinaphthyl-N,N'-diphenyl-4,4'-diphenyl-1,1'-diamine and a bis(N-allylcarbazole) or a bis(N-alkylcarbazole), a heterocyclic compound represented by a pyrazoline derivative, a stilbene compound, a hydrazone compound, a triazole derivative, an oxadiazole derivative and a porphyrin derivative, a polymer such as a polycarbonate and a styrene derivative having a monomer as mentioned above as a side chain, polyvinylcarbazole and polysilane. A hole transport material is not particularly limited as long as it forms a thin film required for forming a device and it is a material capable of injecting holes from an electrode and transporting holes. Examples of the hole injection layer for improving a hole injection property and provided between a hole transport layer and an anode include a layer formed of a star burst amine such as a phthalocyanine derivative and m-MTDATA, and a layer formed of a polymer such as polythiophene (e.g., PEDOT) and a polyvinylcarbazole derivative.

For the electron transport material, it is necessary to efficiently transport electrons from a negative electrode between the electrodes to which an electric field is applied. The electron transport material preferably has a high electron injection efficiency and efficiently transports electrons injected. To satisfy this, the electron transport material is required to be a substance having high electron affinity, large electron mobility, excellent stability, rarely generating impurities serving as a trap during manufacturing and use. Examples of such a substance satisfying these conditions include, but are not particularly limited to, a quinolinol derivative/metal complex represented by tris(8-quinolinolato)aluminium complex, a tropolone/metal complex, a perylene derivative, a perinone derivative, a naphthalimide derivative, a naphthalic acid derivative, an oxazole derivative, an oxadiazole derivative, a thiazole derivative, a thiadiazole derivative, a triazole derivative, a bisstyryl derivative, a pyrazine derivative, a phenanthroline derivative, a benzoxazole derivative and a quinoxaline derivative. These electron transport materials may be used singly or stacked with a layer of an electron transport material or in combination as a mixture. Examples of the electron injection layer provided between an electron transport layer and a cathode to improve electron injection property include a metal such as cesium, lithium or strontium and lithium fluoride.

The hole block layer is formed of a hole block substance alone or formed by layering or mixing two types or more hole block substances. Preferable examples of the hole block substance include a phenanthroline derivative such as bathophenanthroline and bathocuproine, a silole derivative, a quinolinol derivative/metal complex, an oxadiazole derivative and an oxazole derivative. The hole block substance is not particularly limited as long as it is a compound capable of blocking holes from discharging out of a device from the cathode side and preventing luminous efficiency from decreasing.

The light emitting layer refers to an organic thin film emitting light, for example, can refer to a hole transport layer, an electron transport layer or a bipolar transport layer capable of emitting intensive light. The light emitting layer is satisfactorily formed of a light-emitting material (e.g., host material, dopant material). This is either a mixture of a host material and a dopant material or a host material alone. Each of the host material and the dopant material may be a single material or a mixture of plurality of materials. The dopant material may be contained either wholly or partly in the whole host material. The dopant material may be either stacked or dispersed. Examples of the light emitting layer include a hole transport layer and an electron transport layer as mentioned above. Examples of the material to be used in the light emitting layer include a carbazole derivative, an anthracene derivative, a naphthalene derivative, a phenanthrene derivative, a phenylbutadiene derivative, a styryl derivative, a pyrene derivative, a perylene derivative, a quinoline derivative, a tetracene derivative, a perylene derivative, a quinacridone derivative, a coumarin derivative, a porphyrin derivative, a phosphorescence metal complex (e.g., Ir complex, Pt complex, Eu complex).

Examples of a method for forming a thin film include generally a vacuum process such as resistance heating vapor deposition, electron beam vapor deposition, sputtering and a molecular stacking method; a solution process such as coating including casting, spin coating, dip coating, blade coating, wire-bar coating and spray coating; a printing method including inkjet printing, screen printing, offset printing and relief printing; and a soft lithographic method including a micro contact printing method. Furthermore, a method in which these methods are used in combination can be employed. The thickness of each layer varies depending upon the resistance values/charge mobility of individual substances and thus is not limited; however, it is selected from the range between 0.5 and 5000 nm, preferably between 1 and 1000 nm and more preferably between 5 and 500 nm.

Of the organic thin films that the organic EL device has in the present invention, a single or a plurality of thin films such as a light emitting layer, a hole transport layer and an electron transport layer present between the anode and cathode electrodes are formed so as to contain a heterocyclic compound represented by the formula (1). In this manner, a device efficiently emitting light even at low electric energy can be obtained.

The organic EL device of the present invention can be obtained by forming a single or a plurality of layers containing a heterocyclic compound represented by the above formula (1) between an anode and a cathode. In particular, the site in which a heterocyclic compound represented by the above formula (1) is used is not limited; however, a heterocyclic compound can be preferably used in a hole transport layer and a light emitting layer and as a host material in combination with a dopant material.

In the organic EL device of the present invention, a heterocyclic compound represented by the above formula (1) can be preferably used as a hole transport layer and a light emitting layer. The heterocyclic compound can be used, for example, in combination with an electron transport material or a hole transport material and a light-emitting material or as a mixture. Examples thereof preferably include, but are not particularly limited to, a quinolinol derivative/metal complex represented by tris(8-quinolinolato)aluminium complex, a tropolone/metal complex, a perylene derivative, a perinone derivative, a naphthalimide derivative, a naphthalic acid derivative, a bisstyryl derivative, a pyrazine derivative, a phenanthroline derivative, a benzoxazole derivative, a quinoxaline derivative, a triphenyl amine, a bis(N-allylcarbazole) or a bis(N-alkylcarbazole), a heterocyclic compound represented by a pyrazoline derivative, a stilbene compound, a hydrazone compound and an oxadiazole derivative. These can be used singly or layered with a different material or used as a mixture.

When a heterocyclic compound represented by the above formula (1) is used in combination with a dopant material as a host material, specific examples of the dopant material include a perylene derivative such as bis(diisopropyl phenyl) perylenetetracarboxylic imide, a perinone derivative, 4-(dicyanomethylene)-2-methyl-6-(p-dimethylaminostyryl)-4H-pyran (DCM) and its analogue, a metal phthalocyanine derivative such as magnesium phthalocyanine and aluminium chlorophthalocyanine, a rhodamine compound, a deazaflavin derivative, a coumarin derivative, an oxazine compound, a squarylium compound, a violanthrone compound, Nile red and a pyrromethene derivative such as 5-cyanopyrromethene-$BF_4$ complex. Furthermore, a phosphorescence material such as acetyl acetone and benzoyl acetone, an Eu complex with phenanthroline used as a ligand, a porphyrin such as an Ir complex, an Ru complex, a Pt complex and an Os complex, an ortho metal complex can be used; however, the dopant material is not limited to these. When two types of dopant materials are mixed, if an assist dopant such as rubrene is used, energy can be efficiently transferred from a host pigment to obtain light emission improved in color purity. In either case, it is preferable to use a dopant having a high fluorescence quantum yield to obtain high brightness property.

When the amount of dopant material (to be used) is extremely large, a concentration quenching phenomenon occurs. Thus, a dopant material is used usually in an amount of 30 mass % or less relative to a host material, preferably 20 mass % or less, further preferably 10 mass % or less. As a method of doping a dopant material to a host material in a light emitting layer, a method of depositing it together with the host material is mentioned. In this case, a dopant material is previously mixed with a host material and may be subjected to co-vapor deposition. Furthermore, it is possible to use a dopant material by sandwiching it between host materials. In this case, a single or two or more dopant layers may be laminated with a layer of a host material.

The dopant may form each of a layer by itself and may be used in mixture. Furthermore, a dopant material can be used by dissolving or dispersing it in a polymer binder such as a solvent-soluble resin including polyvinyl chloride, polycarbonate, polystyrene, polystyrene sulfonic acid, poly(N-vinylcarbazole), poly(methyl)(metha)acrylate, polybutyl methacrylate, polyester, polysulfone, polyphenylene oxide, polybutadiene, a hydrocarbon resin, a ketone resin, a phenoxy resin, polysulfone, polyamide, ethylcellulose, vinyl acetate, an ABS resin and a polyurethane resin; and a hardening resin including a phenolic resin, a xylene resin, a petroleum resin, a urea resin, a melamine resin, an unsaturated polyester resin, an alkyd resin, an epoxy resin and a silicone resin.

A thin film used in an organic EL device according to the present invention is formed of a heterocyclic compound represented by the above formula (1) or a composition thereof generally by a vacuum process such as resistance heating vapor deposition, electron beam vapor deposition, sputtering and molecular stacking method; a solution process such as coating including casting, spin coating, dip coating, blade coating, wire-bar coating and spray coating; a printing method including inkjet printing, screen printing, offset printing and relief printing; and soft lithographic method including a micro contact printing method. Furthermore, these methods may be employed in combination.

The resistance heating vapor deposition, electron beam vapor deposition, sputtering, molecular stacking method, coating method by dissolving or dispersing in a solvent and a resin (e.g., spin coat, cast, dip coat), a LB method, an inkjet method are not particularly limited. Usually, the resistance heating vapor deposition is preferable in view of properties. The thickness of each layer is set in accordance with a resistance value of a light emitting substance, and thus is not limited; however, it is selected from the range between 0.5 and 5000 nm, preferably between 1 and 1000 nm and more preferably between 5 and 500 nm.

The organic EL device of the present invention can be suitably used as a flat panel display. It can be further used as a flat a backlight. In this case, not only a backlight emitting color light but also a backlight emitting white light can be used. A backlight is principally used for the purpose of improving visibility of a display apparatus not emitting light by itself, and employed in e.g., a liquid crystal display apparatus, a clock, an audio instrument, an automobile panel, a display board and an indicator. Particularly, a conventional backlight for use in a liquid crystal display apparatus, in particular, for a personal computer (reducing in thickness remains a problem) is formed of a fluorescent light or a light guide plate, and thus it is difficult to reduce the thickness. However, since a backlight using the light-emitting device of the present invention is characterized by being thin and light, the problem is overcome. Similarly, the organic EL device of the present invention can be usefully used in lighting.

When a heterocyclic compound represented by the formula (1) of the present invention is used, an organic EL display apparatus having a high luminous efficiency and a long life can be obtained. Furthermore, the thin-film transistor devices of the present invention are used in combination, an organic EL display apparatus capable of electrically controlling an ON/OFF phenomenon of applied voltage with high accuracy can be provided at low cost.

Next, the liquid crystal display of the present invention will be described.

When a heterocyclic compound represented by the formula (1) of the present invention is used in e.g., a liquid crystal display, it is important to have a liquid crystalline property. On the other hand, the orientation of a compound can be controlled by use of the liquid crystalline property to improve a semiconductor property of the organic electronics device.

In the specification, the liquid crystal display includes not only a liquid crystal cell but also an optically anisotropic thin film such as a polarization device and an optical compensation sheet.

A derivative of a heterocyclic compound represented by the formula (1) of the present invention is used as a disk-form liquid crystal compound and considered to be suitably used as a structural component of a discotheque liquid crystal phase. At present, the discotheque liquid crystal is applied to an optical compensation sheet and attracts attention. The optical compensation sheet is also called a retardation film. By virtue of use of the retardation film, a liquid crystal display apparatus with an enlarged view angle can be provided without changing color of a displayed image.

Some of the heterocyclic compounds represented by the formula (1) of the present invention have a liquid crystal phase, particularly a discotheque liquid crystal phase. These may be used singly or as a mixture and used by mixing with a compound other than that of the present invention. The heterocyclic compound of the invention may be, for example, a derivative having or not having a liquid crystalline property and is not particularly limited. When a heterocyclic compound represented by the formula (1) of the present invention is used as a thin film, the film can be formed on a support substrate by a vacuum process such as vapor deposition, a solution process such as coating including casting, spin coating, dip coating, blade coating, wire-bar coating and spray coating; a printing method including inkjet printing, screen printing, offset printing and relief printing; and soft lithographic method including a micro contact printing method, and further a method in which these methods are used in combination.

The film thickness is usually 0.1 μm to 30 μm and preferably 0.2 μm to 20 μm.

In coating, a composition as described above can be used. Specific examples of a solvent include, but are not limited to, benzene, toluene, xylene, mesitylene, monochlorobenzene, dichlorobenzene, trichlorobenzene, tetrachlorobenzene, tetrahydrofuran, methylene chloride, chloroform, ether, hexane, cyclohexane, heptane, acetonitrile, acetone, cyclopentanone, cyclohexanone, 2-butanone, 2,4-dimethyl-3-pentanone, ethyl acetate, 1-butanol, fluorobenzene, 1,2-dimethoxyethane, methyl naphthalene, decalin and tetrahydronaphthalene. These solvents may be used singly or in arbitral combination with two or more types. When the composition is used in the form of film, the films can be layered. When the films are layered, the layer may be constituted of the compound of the present invention alone; however, may be constituted of layers formed of a material except the compound of the present invention and a support substrate in addition to the compound of the present invention. Furthermore, the composition of the present invention may employ a binder.

Examples of the support substrate include a substrate formed of glass or a polymer (e.g., polycarbonate, polypropylene, polyether sulfone, polyethylene terephthalate, acryl substrate).

When a compound used in the present invention has a polymerizable substituent, a bond between the compounds can be formed with heat or light. More specifically, on a support substrate, the liquid crystal thin film is formed by coating or a printing method, followed by drying. Thereafter, a discotheque phase is formed at a temperature within a liquid crystal phase forming temperature range and subsequently subjected to thermal polymerization or optical crosslinked polymerization to obtain a thin film of a desired optical compensation sheet.

(Re: Photoelectric Conversion Device)

The semiconductor property of a heterocyclic compound represented by the formula (1) of the present invention is expected to be used for an organic photoelectric conversion device. Examples of the photoelectric conversion device include an image sensor as a solid imaging device, i.e., a charge combining device (CCD) having a function of converting a screen image signal of e.g., a motion picture and a stationary picture to a digital signal. Also, use as an organic photoelectric conversion device is expected by use of more inexpensive, a large area processability, flexible function intrinsic to an organic substance.

(Re: Organic Solar Battery Device)

The organic semiconductor property of a heterocyclic compound represented by the formula (1) of the present invention is expected to be used as a flexible and inexpensive organic solar battery device manufactured by a simple process. More specifically, an organic solar battery device does not use an electrolyte unlike a color sensitizing solar battery and is favorable and advantageous in view of flexibility and improving life. Conventionally, development of a solar battery using an organic thin film semiconductor using a conductive polymer and fullerene in combination has been in a main stream; however, a power conversion efficiency is a matter of concern.

If development proceeds, a heterocyclic compound represented by the formula (1) of the present invention is expected to provide a means for solving this problem.

(Re: Organic Semiconductor Laser Device)

A heterocyclic compound represented by the formula (1) of the present invention is a compound having an organic semiconductor property, and therefore use as an organic semiconductor laser device is expected. More specifically, in an organic semiconductor device containing a heterocyclic compound represented by the formula (1) of the present invention, a resonator structure is integrated and if a density in an excitation state can be sufficiently increased by efficiently injecting carriers, it is expected that light is amplified to emit laser. In the art, laser oscillation due to light excitation is only observed. It is said that it is very difficult to produce a high-density excitation state by injecting carriers required for laser oscillation by electric excitation highly densely to an organic semiconductor device. However, if an organic semiconductor device containing a heterocyclic compound represented by the formula (1) of the present invention is used, the possibility that light emission (electroluminescence) highly efficiently occurs is expected.

EXAMPLES

The present invention will be more specifically described by way of Examples; however, the present invention is not limited to these Examples. In Examples, unless otherwise specified, "parts" represents parts by mass, % represents mass % and (Compound No.) corresponds to the compound described in specific Examples above. Unless otherwise specified, as the reaction temperature, the temperature within a reaction system was described.

Compounds obtained in Synthesis Examples were, as needed, subjected to measurements such as MS (mass analysis spectrum), maximum absorption (λ max) and mp (melting point) to determine the structural formulas. Measurement instruments are as follows.

MS spectrum: Shimadzu QP-5050A
Absorption spectrum: Shimadzu UV-3150

Synthesis Example 1

Synthesis of 1,3,5-Trichloro-2,4,6-triiodobenzene (Scheme 3-(7))

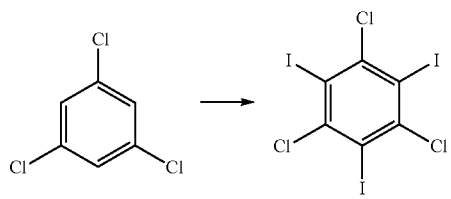

In a 100 mL three-neck flask, 1,3,5-trichlorobenzene (5.0 g, 27.6 mmol), iodine (40.3 g, 31.8 mmol) and a 98% concentrated sulfuric acid solution (75 mL) were placed and heated for 72 hours at 140° C. This was washed sequentially with an aqueous sodium hydrogen sulfite solution, a saturated aqueous sodium hydrogen carbonate solution and water in this order and dried. The resultant substance was recrystallized from THF to obtain a colorless needle crystal (14.3 g, 93%).

M.S. (70 eV, EI) m/z=558 (M$^+$); m.p.>300° C. (sealed tube)

Synthesis Example 2

Synthesis of 1,3,5-Trichloro-2,4,6-tris[(trimethylsilyl) ethynyl]benzene (corresponding to Scheme 3-(8))

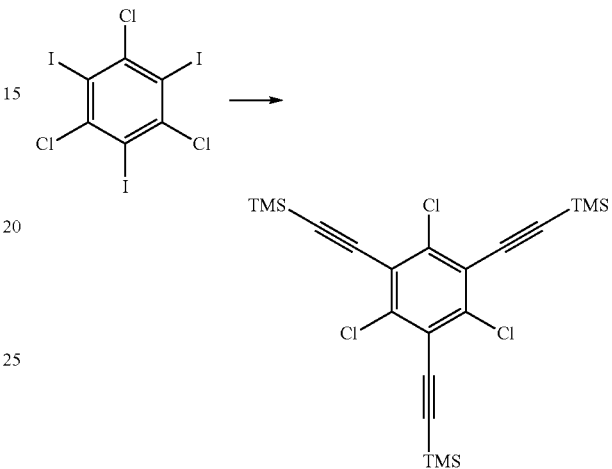

Under a nitrogen atmosphere, in a 50 mL three-neck flask, 1,3,5-trichloro-2,4,6-triiodobenzene (5.0 g, 8.94 mmol) obtained in Synthesis Example 1, diisopropyl amine (4.5 mL) and THF (29.8 mL) were placed and degassed by Ar bubbling for 30 minutes. Pd(PPh$_3$)$_4$ (931 mg, 0.81 mmol), CuI (307 mg, 1.6 mmol) and trimethylsilylacetylene (5.68 mL, 40.2 mmol) were added and refluxed for 63 hours.

After the reaction was terminated with a 1N hydrochloric acid solution (20 mL), the reaction solution was extracted with ethyl acetate (30 mL×5), washed with an aqueous sodium hydrogen carbonate solution (150 mL×1) and saturated saline solution (150 mL×2) and dried over anhydrous magnesium sulfate. After the solvent was distilled away under reduced pressure, the residue was purified by column chromatography (silica gel, hexane, butch, original point). The resultant solid substance was recrystallized from acetonitrile to obtain a yellow solid substance (2.915 g, 69%).

$^1$H-NMR (270 MHz, CDCl$_3$) δ0.28 (s, 18H); $^{13}$C-NMR (67.8 MHz, CDCl$_3$) δ-0.2, 97.4, 108.1, 122.7, 139.1; M.S. (70 eV, EI) m/z=468 (M); m.p.159.7-161.1° C.

Synthesis Example 3

Synthesis of benzo[1,2-b:3,4-b':5,6-b"]trithiophene (Scheme 1-(2))

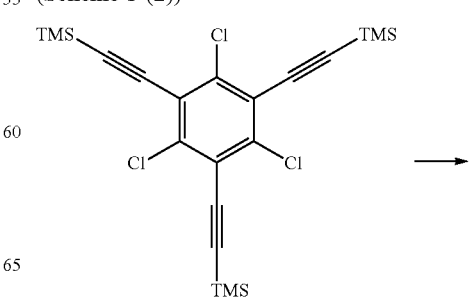

-continued

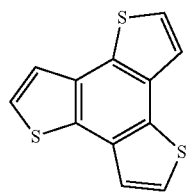

In a 30 mL round-bottom flask, sodium sulfide nonahydrate (7.74 g, 32.2 mmol) and NMP (138 mL) were placed and stirred for 15 minutes. Subsequently, 1,3,5-trichloro-2,4,6-tris(trimethylsilylethynyl)benzene (3.0 g, 6.38 mmol) obtained in Synthesis Example 2 was added and heated at 180-190° C. for 38 hours. After completion of the reaction, the reaction mixture was poured into a saturated aqueous ammonium chloride solution (700 mL) and a precipitated solid substance was obtained by filtration. The resultant solid substance was extracted with chloroform (210 mL), washed with saturated saline solution and dried over anhydrous magnesium sulfate. After the solvent was distilled away under reduced pressure and purification was performed by column chromatography (hexane, butch, Rf=0.5) to obtain a white solid substance (814 mg, 62%).

$^1$H-NMR (270 MHz, CDCl$_3$) δ7.64 (d, J=5.4 Hz, 3H) 7.54 (d, J=5.4 Hz, 3H);
$^{13}$C-NMR (99.5 MHz, CDCl$_3$) δ131.94, 131.55, 125.11, 122.44; M.S. (70 eV, EI) m/z=246 (M$^+$);
m.p.156.7-157.7° C.

Synthesis Example 4

Synthesis of 1,3,5-Trichloro-2,4,6-trioctyn-1-ylbenzene (corresponding to Scheme 3-(8))

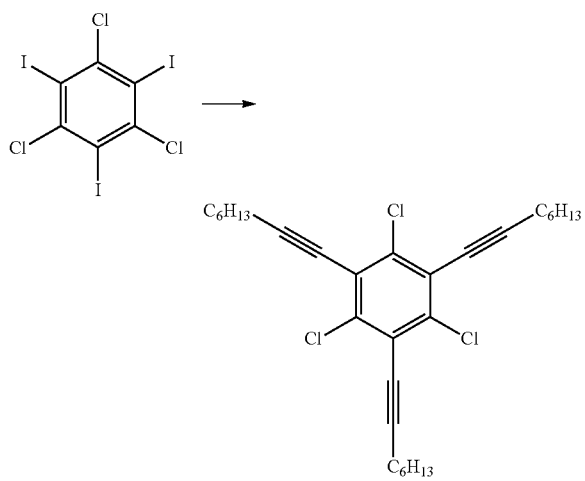

Under a nitrogen atmosphere, in a 20 mL two-neck flask, 1,3,5-trichloro-2,4,6-triiodobenzene (1.0 g, 1.8 mmol) obtained in Synthesis Example 1, diisopropyl amine (0.8 mL) and toluene (9.0 mL) were placed and degassed by Ar bubbling for 30 minutes. Pd (PPh$_3$)$_4$ (186 mg, 0.16 mmol), CuI (61 mg, 7.2 mmol) and 1-octyne (1.0 mL, 7.2 mmol) were added and refluxed for 14 hours. After the reaction was terminated with water (10 mL), the reaction mixture was extracted with chloroform (10 mL×3), washed with an aqueous sodium hydrogen carbonate solution (30 mL×1) and saturated saline solution (30 mL×2) and dried over anhydrous magnesium sulfate. After the solvent was distilled away under reduced pressure, the residue was subjected to column chromatography (silica gel, hexane, butch, original point) and purified by HPLC (JAIGEL, 1H-2H, Rv 194 mL) to obtain yellow oil (528 mg, 58%).

$^1$H-NMR (400 MHz, CDCl$_3$) δ2.53 (t, J=7.0 Hz, 6H), 1.67-1.61 (m, 6H), 1.56-1.47 (m, 6H), 1.34-1.29 (m, 4H), 0.90 (t, J=7.0 Hz, 9H); $^{13}$C-NMR (99.5 MHz, CDCl$_3$) δ137.9, 123.5, 103.4, 75.4, 31.8, 28.9, 28.7, 23.0, 20.3, 14.5; M.S. (70 eV, EI) m/z=506 (M); Anal. Calcd for C$_{30}$H$_{39}$Cl$_3$: C, 71.21; H, 7.77%. Found: C, 71.10; H, 7.88%.

Example 1

Synthesis of 2,5,8-Trihexylbenzo[1,2-b:4,5-b':5,6-b"]trithiophene (5)

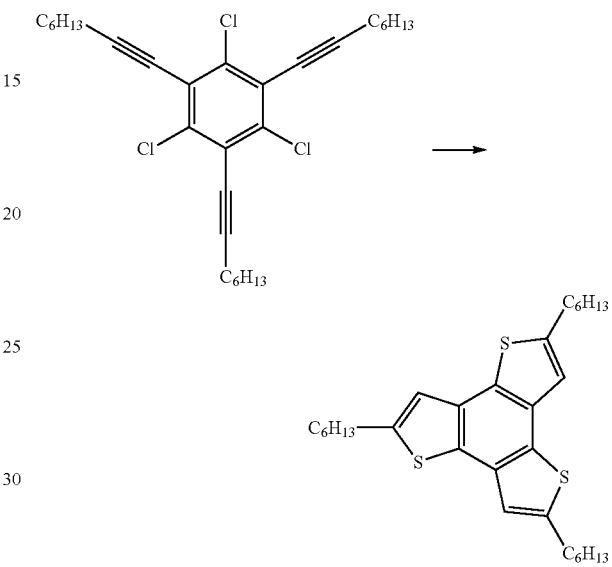

In a 30 mL round-bottom flask, sodium sulfide nonahydrate (720 mg, 3.0 mmol) and NMP (18 mL) were placed and stirred for 15 minutes. Subsequently, 1,3,5-trichloro-2,4,6-trioctyn-1-ylbenzene (3.0 g, 6.38 mmol) obtained in Synthesis Example 4 was added and heated at 180-190° C. for 12 hours. After completion of the reaction, the reaction mixture was poured into a saturated aqueous ammonium chloride solution (180 mL), extracted with toluene (100 mL×2), washed with saturated saline solution (200 mL×3) and dried over anhydrous magnesium sulfate. After the solvent was distilled away under reduced pressure, the residue was purified by column chromatography (silica gel, hexane, Rf=0.5) to obtain a colorless solid substance (1440 mg, 57%).

$^1$H-NMR (400 MHz, CDCl$_3$) δ 7.18 (s, 3H), 2.97 (t, J=7.6, 6H), 1.77 (quint, J=8.0 Hz, 6H), 1.43-1.32 (m, 18H), 0.90 (t, J=7.2 Hz, 9H); $^{13}$C-NMR (99.5 MHz, CDCl$_3$) δ145.6, 131.5, 129.3, 119.0, 31.8, 31.6, 30.9, 28.9, 22.7, 14.3; M.S. (70 eV, EI) m/z=498 (M); m.p. 36.1-38.3; Anal. Calcd for C$_{30}$H$_{42}$S$_3$: C, 72.23; H, 8.49%. Found: C, 72.26; H, 8.55%.

Synthesis Example 5

Synthesis of 1,3,5-Trichloro-2,4,6-tris(phenylethynyl)benzene (corresponding to Scheme 3-(8))

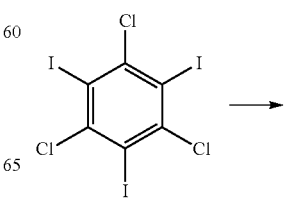

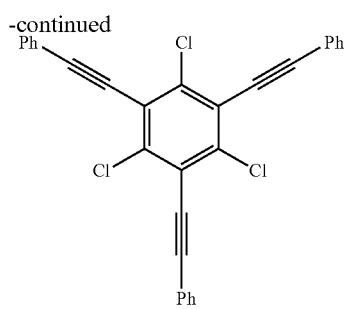

Under a nitrogen atmosphere, in a 100 mL three-neck flask, 1,3,5-trichloro-2,4,6-triiodobenzene (5.0 g, 8.94 mmol) obtained in Synthesis Example 1, diisopropylamine (4.5 mL) and THF (40 mL) were placed and degassed by Ar bubbling for 30 minutes. Pd(PPh$_3$)$_4$ (200 mg, 0.17 mmol), CuI (310 mg, 1.6 mmol) and ethynyl benzene (3.92 mL, 35.8 mmol) were added and refluxed for 20 hours. After the reaction was terminated with a 1N hydrochloric acid solution (20 mL), the reaction mixture was extracted with methylene chloride (50 mL×3), washed with an aqueous sodium hydrogen carbonate solution (150 mL×1) and saturated saline solution (150 mL×2) and dried over anhydrous magnesium sulfate. After the solvent was distilled away under reduced pressure, a by-product(s) was removed by column chromatography (silica gel, hexane, butch) and purification was performed by column chromatography (silica gel, hexane: methylene chloride=10:1, Rf=0.38). The resultant solid substance was dissolved in hot benzene and reprecipitated from hexane to obtain a white solid substance (3.3 g, 77%).
$^1$H-NMR (400 MHz, CDCl$_3$) δ7.64-7.60 (m, 6H), 7.42-7.35 (m, 9H);
$^{13}$C-NMR (99.5 MHz, CDCl$_3$) δ138.1, 132.1, 129.5, 128.6, 123.1, 122.4, 101.1, 83.3;
M.S. (70 eV, EI) m/z=482 (M$^+$); mp186.8-187.3° C.

Example 2

Synthesis of 2,5,8-Triphenylbenzo[1,2-b:3,4-b':5,6-b"]trithiophene (142)

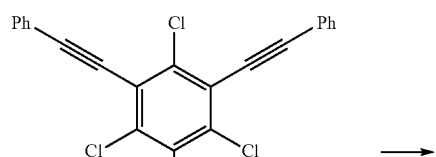

In a 30 mL round-bottom flask, sodium sulfide nonahydrate (720 mg, 3.0 mmol) and NMP (18 mL) were placed and stirred for 15 minutes. Subsequently, 1,3,5-trichloro-2,4,6-tris(phenylethynyl)benzene (253 mg, 0.50 mmol) obtained in Synthesis Example 5 was added and heated at 180-190° C. for 12 hours. After completion of the reaction, the reaction mixture was poured in a saturated aqueous ammonium chloride solution (180 mL). A precipitated solid substance was obtained by filtration, washed with water (100 mL), ethanol (100 mL) and benzene (50 mL) and dried under vacuum. The residue was recrystallized from toluene to obtain a yellow needle crystal (141 mg, 71%).
$^1$H-NMR (400 MHz, CDCl$_3$) δ7.82-7.79 (m, 9H), 7.51-7.45 (m, 6H), 7.41-7.38 (m, 3H);
$^{13}$C-NMR (99.5 MHz, CDCl$_3$) 143.7, 134.3, 132.5, 131.2, 129.2, 128.4, 126.5, 117.9;
M.S. (70 eV, EI) m/z=474 (M$^+$); mp >300° C.; Anal. Calcd for C$_{30}$H$_{18}$S$_3$:C, 75.91; H, 3.82%. Found: C, 75.91; H, 3.74%.

Example 3

Synthesis of 2-Benzo[1,2-b:4,5-b':5,6-b"]trithiophenealdehyde (80)

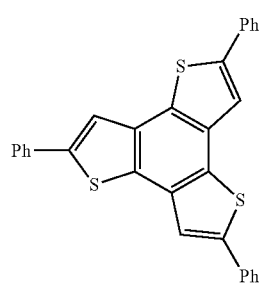

Under a nitrogen atmosphere, in a test tube, benzo[1,2-b:4,5-b':5,6-b"]trithiophene (100 mg, 0.405 mmol) obtained in Synthesis Example 3, DMF (0.10 mL, 1.34 mmol) and 1,2-dichloroethane (1.3 mL) were placed. In an ice bath, phosphorus oxychloride (0.13 mL, 1.34 mmol) was added and refluxed for 17 hours. Subsequently, DMF (0.10 mL, 13.4 mmol) and phosphorus oxychloride (0.13 mL, 1.34 mmol) were added, and refluxed for further 17 hours. After a 10% aqueous potassium hydroxide solution was added, the reaction mixture was extracted with chloroform (10 mL×2), washed with saturated saline solution (40 mL×3) and dried over anhydrous magnesium sulfate. After the solvent was distilled away under reduced pressure, the residue was purified by column chromatography (silica gel, chloroform, Rf=0.4) to obtain a yellow solid substance (92.7 mg, 83%).
$^1$H-NMR (400 MHz, CDCl$_3$) δ10.07 (s, 1H), 8.12 (s, 1H), 7.56-7.51 (m, 4H);
$^{13}$C-NMR (99.5 MHz, CDCl$_3$) δ183.9, 141.9, 136.5, 135.4, 132.5, 132.2, 131.9, 131.1, 130.7, 126.0, 125.8, 122.6, 122.41; M.S. (70 eV, EI) m/z=274 (M$^+$)

Example 4

Synthesis of 2,5,8-Tribromobenzo[1,2-b:3,4-b':5,6-b"]trithiophene (33)

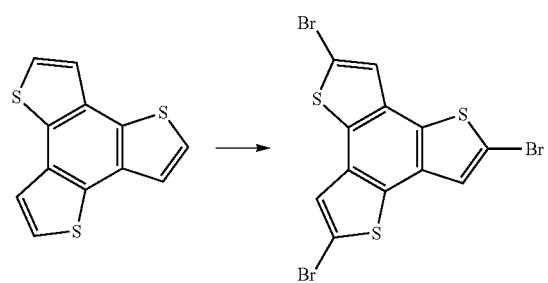

Under a nitrogen atmosphere, in a 50 mL three-neck flask, benzo[1,2-b:4,5-b':5,6-b"]trithiophene (800 mg, 3.25 mmol)

obtained in Synthesis Example 3, methylene chloride (22.7 mL) and acetic acid (5.7 mL) were added. Under light exclusion conditions, NBS (1.73 g, 9.74 mmol) was added little by little and stirred at room temperature 48 hours. After completion of the reaction, water (20 mL) was added. A precipitated solid substance was obtained by filtration and washed with ethanol (50 mL) and THF (20 mL) to obtain a light purple solid substance (1.2 g, 76%).
$^1$H-NMR (270 MHz, CDCL$_3$) δ7.51 (s, 3H); M.S. (70 eV, EI) m/z=484 (M$^+$)

Example 5

Synthesis of 2,5,8-Tris(4-(N,N-Diphenylamino)phenyl) benzo[1,2-b:3,4-b':5,6-b"]trithiophene (1010): Tpa-BTT

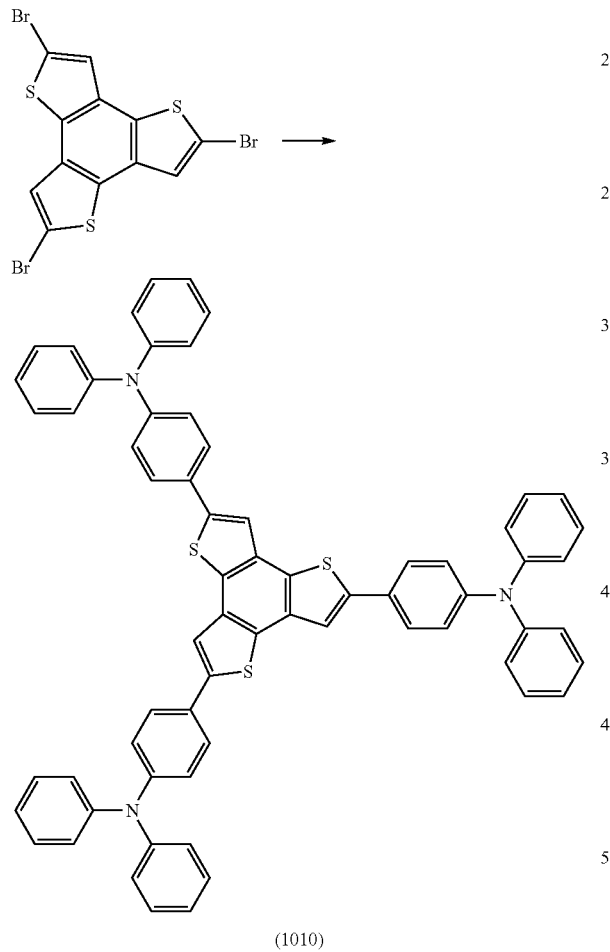

(1010)

Under a nitrogen atmosphere, 2,5,8-tribromobenzo[1,2-b: 3,4-b':5,6-b"]trithiophene (450 mg, 0.93 mmol) obtained in Example 4, 4-(diphenylamino)phenyl boronic acid (1.2 g, 4.19 mmol) and tripotassium phosphate hydrate (4.74 g, 22.4 mmol) were suspended in DMF (18.9 mL) and degassed by Ar bubbling for 40 minutes. Pd(PPh$_3$)$_4$ (161 mg, 0.14 mmol) was added and heated at 90-100° C. for 16.5 hours. After completion of the reaction, water (10 mL) was added. A precipitated solid substance was obtained by filtration, washed with water (50 mL) and acetone (10 mL) and dried under reduced pressure. Extraction was continuously performed with chloroform by means of Soxhlet. The extract was dissolved in hot chloroform and reprecipitated from acetonitrile to obtain a light yellow substance (780 mg, 86%).
$^1$H-NMR (400 MHz, CDCl$_3$) δ7.07 (t, J=6.0 Hz, 6H), 7.14 (dd, J=9.6 Hz, 12H), 7.16 (d, J=8.8 Hz, 6H), 7.30 (dd, J=7.6 Hz, 12H), 7.65 (dt, J=6.0, 3.6 Hz, 6H). 7.69 (s, 3H); M.S. (70 eV, EI) m/z=484 (M$^+$);
mp>300° C.; Anal. Calcd for C$_{66}$H$_{45}$N$_3$S$_3$: C, 81.20; H, 4.65; N, 4.30%. Found: C, 80.96; H, 4.34; N, 4.31%.

Example 6

Synthesis of 2,5,8-Tris(4-(N-(1-naphthyl)-N-phenylamino)phenyl)benzo[1,2-b:3,4-b':5,6-b"]trithiophene (1029): Ndpa-BTT

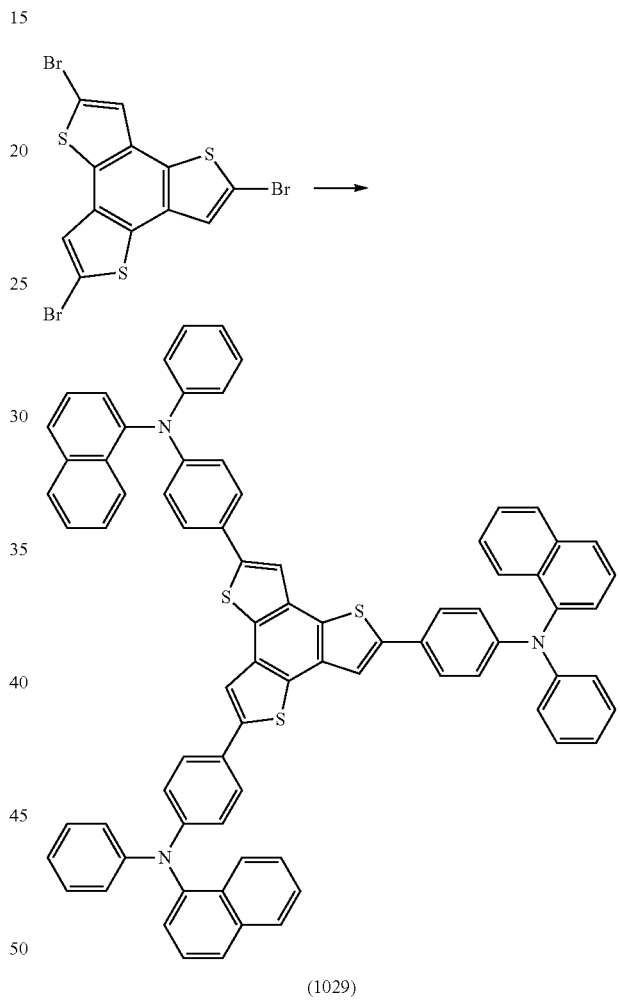

(1029)

Under a nitrogen atmosphere, 2,5,8-tribromobenzo[1,2-b: 3,4-b':5,6-b"]trithiophene (450 mg, 0.93 mmol) obtained in Example 4, 4-(1-naphthylphenylamino)phenyl boronic acid (1.42 g, 4.19 mmol) and tripotassium phosphate hydrate (4.74 g, 22.4 mmol) were suspended in DMF (18.9 mL) and degassed by Ar bubbling for 30 minutes. Pd(PPh$_3$)$_4$ (161 mg, 0.14 mmol) was added and heated at 90-100° C. for 18 hours. After completion of the reaction, water (20 mL) was added. A precipitated solid substance was obtained by filtration, washed with water (50 mL) and acetone (10 mL) and dried under reduced pressure. Extraction was continuously performed with chloroform by means of Soxhlet. The extract was dissolved in hot chloroform and reprecipitated from acetonitrile to obtain a light yellow substance (969 mg, 92%).

H-NMR (400 MHz, CDCl$_3$) δ6=6.99 (d, J=8.0 Hz, 3H), 7.03 (d, J=8.8 Hz, 6H), 7.13 (d, J=8.0 Hz, 6H), 7.24 (d, J=8.0 Hz, 6H), 7.39 (t, J=8.8 Hz, 6H), 7.47 (t, J=8.8 Hz, 3H), 7.52 (d, J=8.0 Hz, 3H), 7.58 (d, J=8.8 Hz, 6H), 7.61 (s, 3H), 7.81 (d, J=7.6 Hz, 3H), 7.91 (d, J=8.4 Hz, 3H), 7.95 (d, J=8.4 Hz, 3H), MS(MALDI-TOF,1,8,9-trihydroxyanthracene matrix) m/z=1127.27

Example 7

Formation of Thin-Film Transistor Device and Evaluation Thereof—Part 1

A 200 nm n-doped silicon wafer with a SiO$_2$ thermal oxidation film was placed in a vapor deposition apparatus, which was evacuated until degree of vacuum of the apparatus reached 5.0×10$^{-3}$ Pa or less. In accordance with a resistance heating vapor deposition method, compound No. 142 was vapor deposited on the electrode to a thickness of 50 nm under the conditions of a substrate temperature of about 25° C. to form a semiconductor layer (2). Subsequently, to the substrate, a shadow mask for forming an electrode was attached and placed in a vapor deposition apparatus, which was evacuated until degree of vacuum in the apparatus reached 1.0×10$^{-4}$ Pa or less. By the resistance heating vapor deposition method, gold electrodes, that is, a source electrode (1) and a drain electrode (3), were vapor deposited to a thickness of 80 nm to obtain a TC (top contact) type organic transistor device of the present invention.

Figure 3:
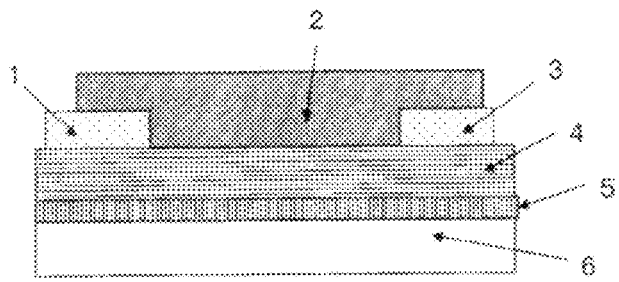
FIG. 3 is a schematic view showing the thin-film transistor of the present invention obtained in Example 7.
Figure 4:
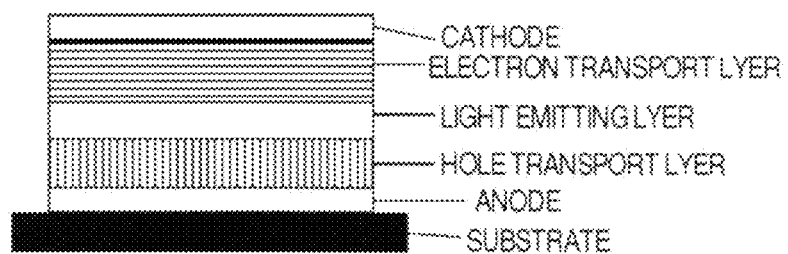
FIG. 4 shows the structure of organic EL devices of Examples 8 and 9.
Figure 5:
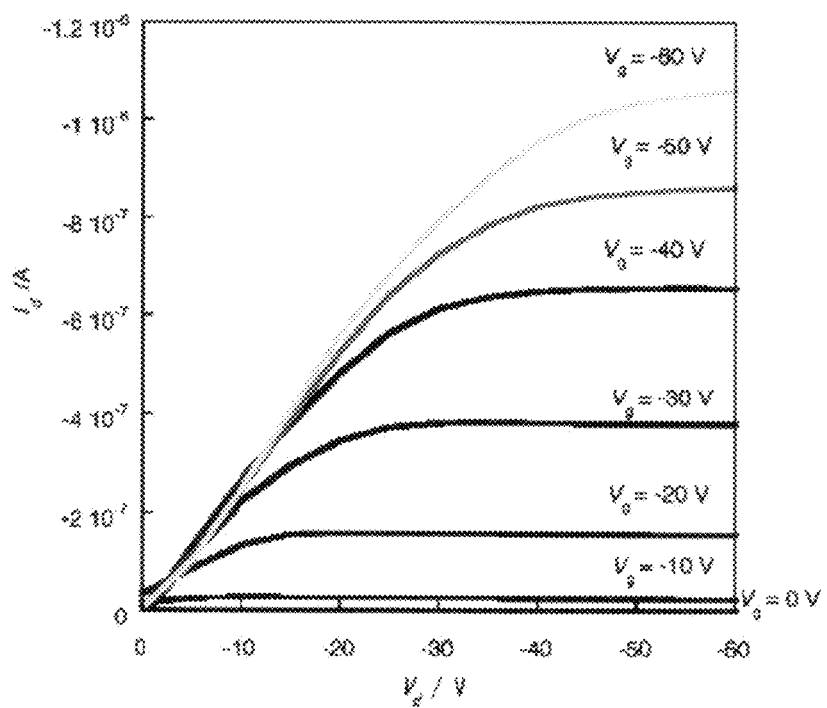
FIG. 5 shows a drain current-drain voltage curve of the organic thin-film transistor in Example 7.
Figure 6:
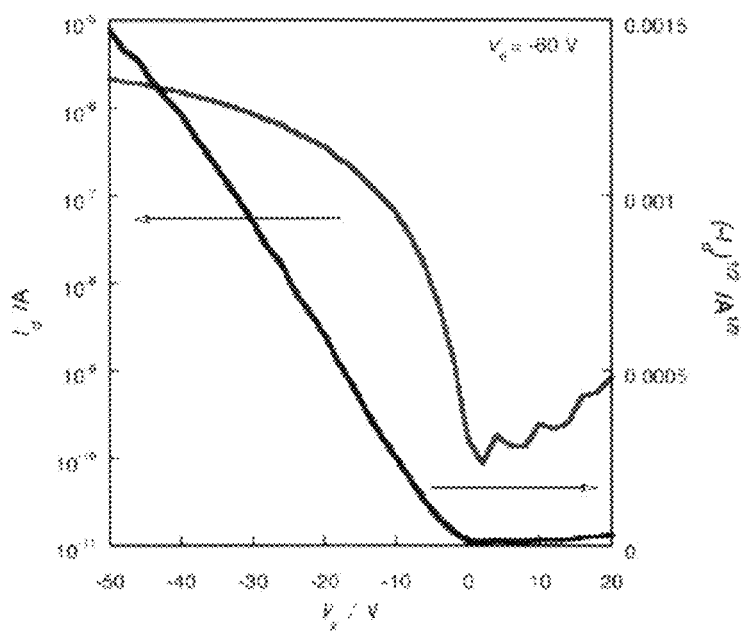
FIG. 6 shows a drain current-gate voltage curve of the organic thin-film transistor in Example 7.
Figure 7:
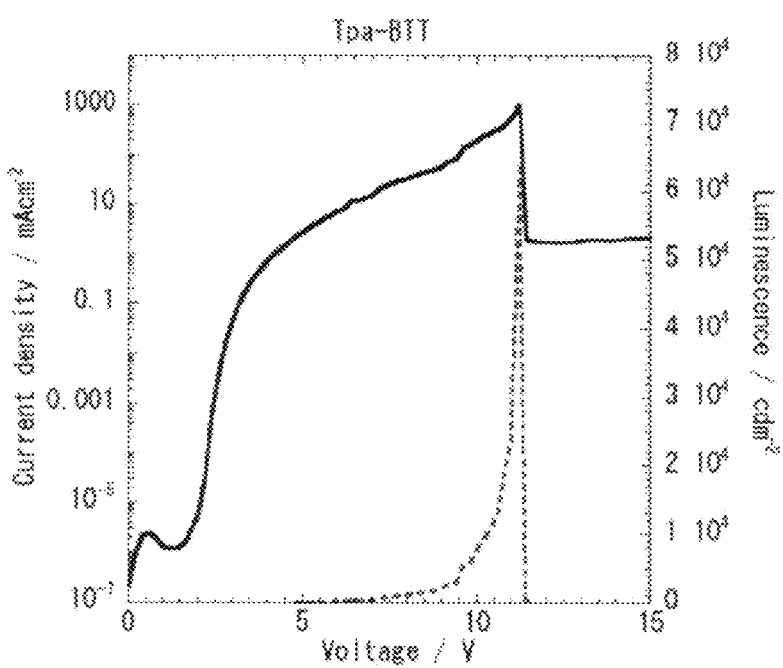
FIG. 7 shows an I-V-L characteristic graph (Tpa-BTT) of the organic EL device of Example 8.
Figure 8:
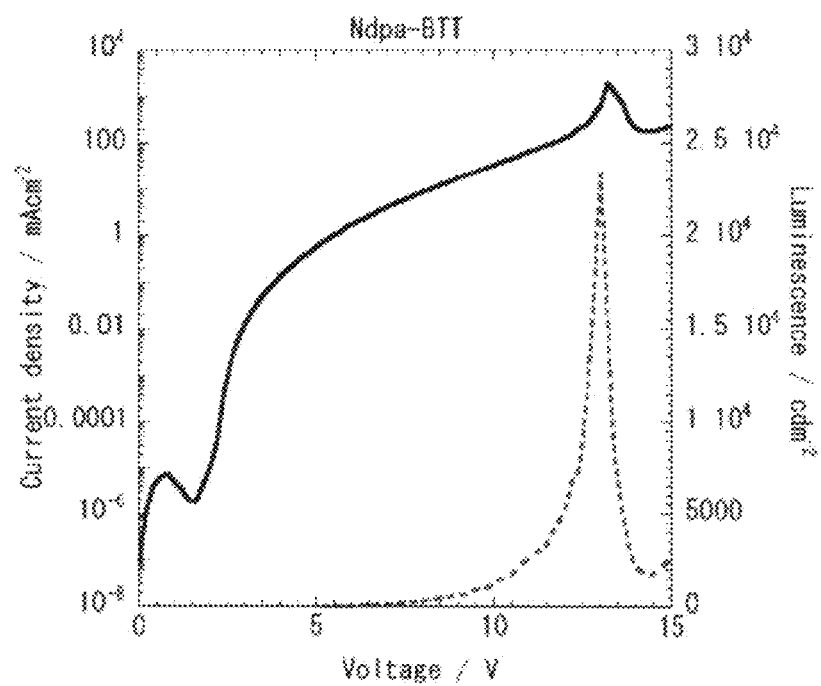
FIG. 8 shows an I-V-L characteristic graph (Ndpa-BTT) of the organic EL device in Example 9.

Note that in the field effect transistor of the Example, the thermal oxidation film of the n-doped silicon wafer with a thermal oxidation film has the function of an insulating layer (4) and the n-doped silicon wafer has the functions of a substrate (6) as well as a gate electrode (5) (see FIG. 3).

The resultant field effect transistor was placed in a prober. A semiconductor property was measured by use of a semiconductor parameter analyzer 4155C (manufactured by Agilent). The semiconductor property was measured by scanning at a gate voltage of 10V to −100V by a 20V step and at a drain voltage of 0V to −60V. In this way, a drain current-drain voltage was measured. As a result, current saturation was observed. Furthermore, the drain current was set to −60V and a gate voltage was measured by scanning from 20V to −50V. In this way, a gate voltage-drain current was measured. From the resultant voltage current curve, it was found that the device was a p-type semiconductor, a carrier mobility was 10$^{-3}$ cm$^2$/Vs and a threshold voltage was −12V.

Example 8

Formation of Organic EL Device and Evaluation Thereof—Part 1

A glass substrate (manufactured by Tokyo Sanyo Vacuum Industries Co., Ltd. 14Ω/☐ or less) having an ITO transparent conducting layer (150 nm) formed by deposition was cut into pieces of 25×25 mm and etching was performed. The resultant substrate was ultrasonically washed with a neutral detergent for 10 minutes, ultrasonically washed with ion-exchanged water for 5 minutes×2 times, ultrasonically washed with acetone for 5 minutes×2 times, and then ultrasonically washed with isopropyl alcohol for 5 minutes×2 times. The substrate was washed with UV-ozone for 10 minutes immediately before formation of a device and placed in a vacuum deposition apparatus, which was evacuated until degree of vacuum in the apparatus reached 3.0×10$^{-3}$ Pa or less. By the resistance heating vapor deposition method, first, No. 1010 compound (Tpa-BTT) of Example 10 (Synthesis Example) as a hole transport material was vapor-deposited to a thickness of 50 nm to form a hole transport layer. Then, tris(8-quinolinolato)aluminium (AlQ3) was vapor deposited to a thickness of 50 nm as a light emitting layer as well as an electron transport layer. Furthermore, lithium fluoride was vapor deposited to a thickness of 0.8 nm and aluminium was vapor deposited to a thickness of 100 nm to form a cathode. In this manner, a round type organic EL device of φ2 mm in diameter was prepared. The structure of the organic EL device is shown in FIG. 1.

When the organic EL device has a current density of 100 mA/cm$^2$, the driving voltage was 9.5V. Furthermore, the current efficiency was 3.64 cd/A (1000 cd/m$^2$).

Example 9

Formation of Organic EL Device and Evaluation Thereof—Part 2

An organic EL device was prepared in the same manner as in Example 8 except that compound No. 1029 (Ndpa-BTT) was used in place of compound No. 1010 (Tpa-BTT) of Example 5. The organic EL device had a current density of 100 mA/cm$^2$, a driving voltage of 11.7 V and a current efficiency of 3.89 cd/A (1000 cd/m$^2$).

Example 10

Formation of Organic EL Device and Evaluation Thereof—Part 3

An organic EL device was prepared in the same manner as in Example 8 except that compound No. 67 (described later) was used in place of compound No. 1010 (Tpa-BTT) of Example 5. The organic EL device had a current density of 100 mA/cm$^2$, a driving voltage of 7.8 V and a current efficiency of 4.2 cd/A (1000 cd/m$^2$).

Example 11

Formation of Thin-Film Transistor Device and Evaluation Thereof—Part 2

A thin-film transistor device was formed in the same manner as in Example 7 except that compound No. 1013 (described above) was used in place of compound No. 142 of Example 7. The device was a p-type semiconductor and has a carrier mobility of 8×10$^{-4}$ cm$^2$/Vs and a threshold voltage of −20 V.

Example 12

Synthesis of 2,5,8-Tris(4-(N-carbazolyl)phenyl)benzo[1,2-b:3,4-b':5,6-b"]trithiophene (1013)

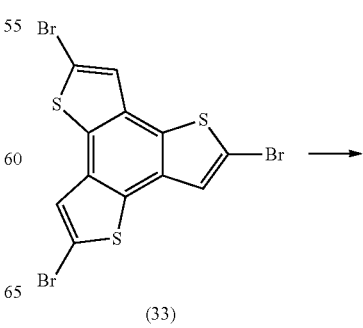

(33)

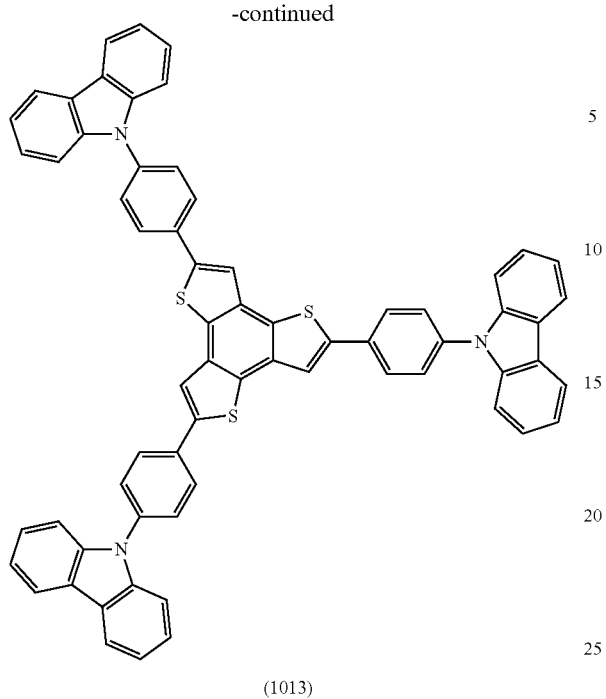

(1013)

Under a nitrogen atmosphere, 2,5,8-tribromobenzo[1,2-b:3,4-b':5,6-b"]trithiophene (33) (500 mg, 1.04 mmol) obtained in Example 4, 4-(N-carbazolyl)phenyl boronic acid (1.34 g, 4.66 mmol) and tripotassium phosphate hydrate (3.96 g, 18.6 mmol) were suspended in DMF (40 mL) and degassed by Ar bubbling for 30 minutes. Pd(PPh$_3$)$_4$ (179 mg, 0.155 mmol) was added and heated at 90-100° C. for 18 hours. After completion of the reaction, water (30 mL) was added. A precipitated solid substance was obtained by filtration, washed with water (50 mL) and acetone (10 mL) and dried under reduced pressure. Vacuum sublimation purification was performed to obtain a light yellow substance (47.7 mg, 5%). MS (MALDI-TOF,1,8,9-trihydroxyanthracene matrix) m/z=966.34

Example 13

Synthesis of 2,5,8-Tris(diphenylamino)benzo[1,2-b:3,4-b':5,6-b"]trithiophene (67)

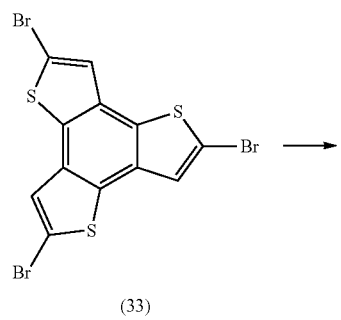

(33)

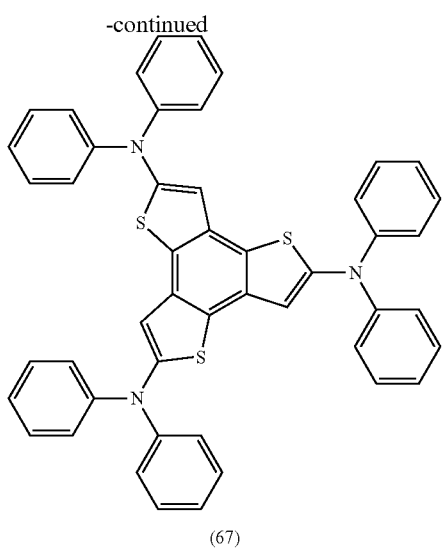

(67)

Under a nitrogen atmosphere, 2,5,8-tribromobenzo[1,2-b:3,4-b':5,6-b"]trithiophene (33) (500 mg, 1.04 mmol) obtained in Example 4, diphenyl amine (0.78 g, 4.66 mmol) and tertiary butoxy sodium (0.39 g, 4.0 mmol) were suspended in xylene (10 mL) and degassed by Ar bubbling for 30 minutes. Pd(OAc)$_2$ (2.3 mg, 0.01 mmol) and tri(tert-butyl) phosphine (10 mg) were added and heated at a reflux temperature for 34 hours. After completion of the reaction, water (10 mL) was added. The mixture was extracted with chloroform, washed and dried over anhydrous magnesium sulfate, and a solvent was distilled away under reduced pressure. The residue was dissolved in methylene chloride, reprecipitated from acetonitrile. The precipitated solid substance was obtained by filtration, washed with water (50 mL) and dried under reduced pressure. Vacuum sublimation purification was performed to obtain a light yellow substance (300 mg, 39%).

H-NMR (400 MHz, CDCl$_3$) δ=6.87 (s, 3H), 7.08 (t, J=8.4 Hz, 6H), 7.21 (d, J=7.6 Hz, 12H), 7.28 (dd, J=7.2 Hz, J=8.8 Hz, 12H),

;MS (EI, 70 eV) m/z=747 (M$^+$); m.p.130.6-132.2

Abs.λmax340 nm (∈=60800); Emis.λmax410 nm

Example 14

Alkylation Reaction of BTT via Lithiation

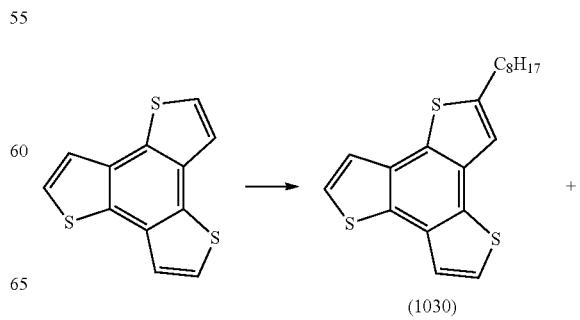

(1030)

-continued

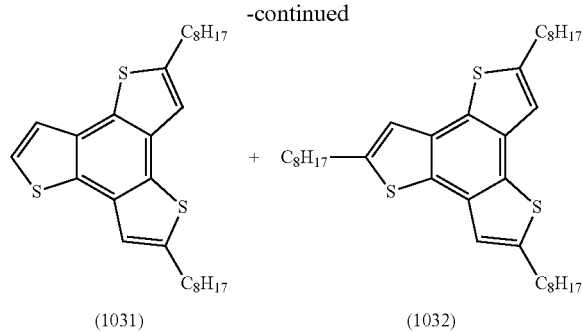

(1031)     (1032)

Under a nitrogen atmosphere, in a 50 mL three-neck flask, benzo[1,2-b:4,5-b':5,6-b"]trithiophene (Schemel-(2)) (800 mg, 3.25 mmol) obtained in Synthesis Example 3 and tetrahydrofuran (22.7 mL) were placed and cooled to 0° C. To this, a 1.59 mol/ln-butyllithium hexane solution (4.5 mL, 7.15 mmol) was added and stirred for 2 hours. Thereafter, temperature was increased to 60° C. To the mixture, n-octyl bromide (2.5 g, 13.0 mmol) was added and reacted for 12 hours. After completion of the reaction, water (20 mL) was added. A precipitated solid substance was obtained by filtration, washed with water (20 mL) to obtain a light yellow substance. The resultant solid substance was separated and analyzed by HPLC. As a result, it was found that a production ratio of raw materials (Scheme 1-(2)):1030:1031:1032 is 3:29:39:21.

Example 15

Acylation Reaction of BTT via the Friedel-Crafts Reaction

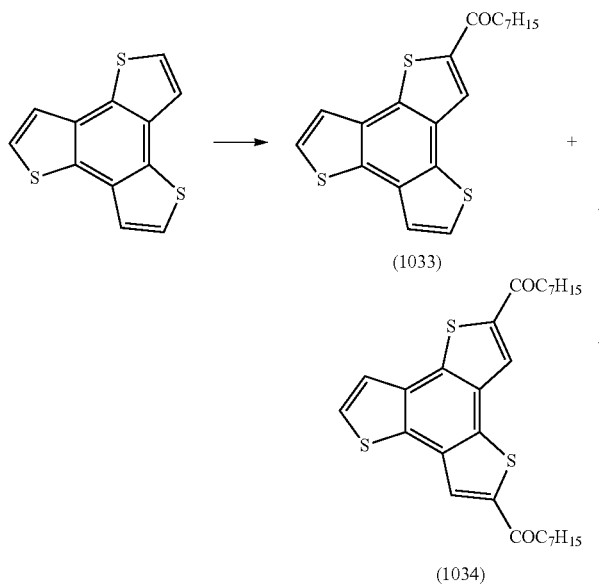

(1033)

(1034)

Under a nitrogen atmosphere, in a 50 mL three-neck flask benzo[1,2-b:4,5-b':5,6-b"]trithiophene (Scheme 1-(2)) (800 mg, 3.25 mmol), obtained in Synthesis Example 3 and methylene chloride (22.7 mL) were placed and cooled to −78° C. To this, aluminum chloride (2.11 g, 13.0 mmol) and octanoyl chloride (1.16 g, 13.0 mmol) were added and stirred for 2 hours and then temperature was increased to room temperature. After completion of the reaction, water (20 mL) was added. A precipitated solid substance was obtained by filtration, washed with water (20 mL) to obtain a light yellow solid substance. The resultant solid substance was separated and analyzed by HPLC. As a result, it was found that a production ratio of 1033:1034 is 21:32.

Example 16

Dibromination Reaction of BTT by NBS Bromination Reaction

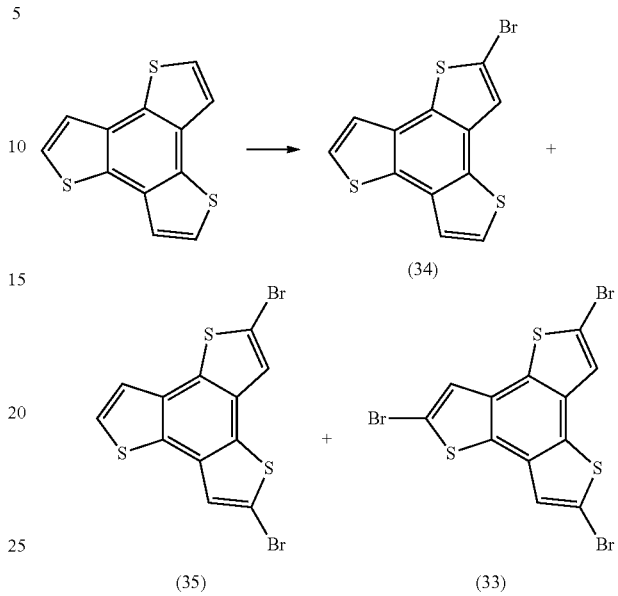

(34)

(35)     (33)

Under a nitrogen atmosphere, in a 50 mL three-neck flask, benzo[1,2-b:4,5-b':5,6-b"]trithiophene (Scheme 1-(2)) (800 mg, 3.25 mmol) obtained in Synthesis Example 3, methylene chloride (22.7 mL) and acetic acid (5.7 mL) were added. Under light exclusion conditions, NBS (1.16 g, 6.5 mmol) was added little by little and stirred at room temperature for 24 hours. After completion of the reaction, water (20 mL) was added. A precipitated solid substance was obtained by filtration and washed with ethanol (50 mL) and water (20 mL) to obtain a light purple solid substance. The resultant solid substance was analyzed by HPLC. As a result, it was found that a production ratio of 34:35:33 is 0.01:1:0.17.

Example 17

Sonogashira Coupling of Dibromo BTT

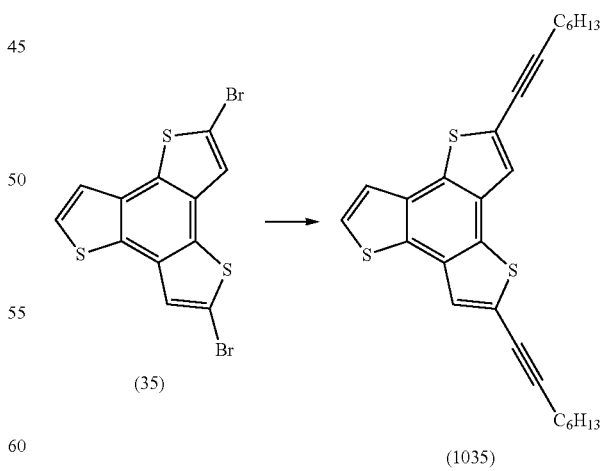

(35)

(1035)

Under a nitrogen atmosphere, in a 20 mL two neck flask a mixture containing 2,5-dibromobenzo[1,2-b:4,5-b':5,6-b"]trithiophene (35) (300 mg) obtained in Example 16, diisopropyl amine (0.6 mL) and toluene (7.0 mL) were placed and degassed by Ar bubbling for 30 minutes. Pd(PPh$_3$)$_4$ (140 mg, 0.12 mmol), CuI (46 mg, 5.4 mmol) and 1-octyne (0.75 mL, 5.4 mmol) were added and refluxed for 16 hours. After the reaction was terminated with water (10 mL), the mixture was extracted with chloroform (10 mL×3), washed with an aqueous sodium hydrogen carbonate solution (20 mL×1) and saturated saline solution (20 mL×2) and dried over anhydrous magnesium sulfate. After the solvent was distilled away under reduced pressure, the residue was purified by (silica gel, hexane) was performed by column chromatography and purified by HPLC to obtain a white solid substance (120 mg).

Example 18

Synthesis of 2,5,8-Trihexylbenzo[1,2-b:4,5-b':5,6-b"]triselenophene (1036)

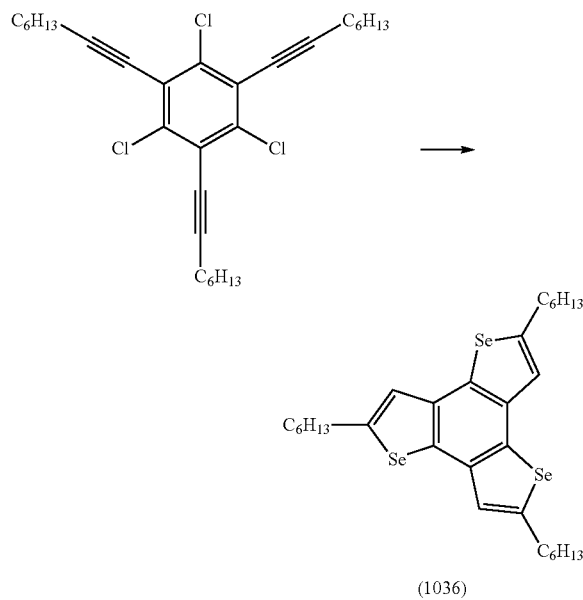

Under a nitrogen atmosphere, selenium (99 mg, 1.25 mmol) and NaBH$_4$ (47.3 mg, 1.25 mmol) were dissolved in ethanol and stirred for 30 minutes while maintaining at 5° C. Subsequently, 1,3,5-trichloro-2,4,6-trioctyn-1-ylbenzene (167 mg, 0.33 mmol) obtained in Synthesis Example 4 and NMP (12 mL) were added and heated at 180-190° C. for 20 hours. After completion of the reaction, a saturated aqueous ammonium chloride solution (180 mL) was poured. A precipitated solid substance was obtained by filtration, washed with water (100 mL), ethanol (100 mL) and acetone (50 mL) and dried under vacuum to obtain a yellow solid substance (169 mg, 80%).

Example 19

Synthesis of 2,5,8-Triphenylbenzo[1,2-b:3,4-b':5,6-b"]trithiophene (1037)

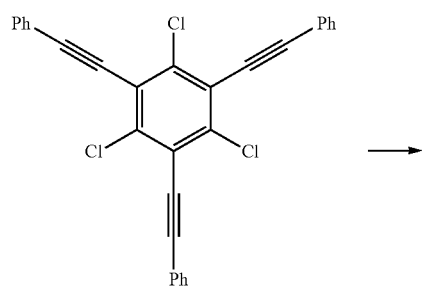

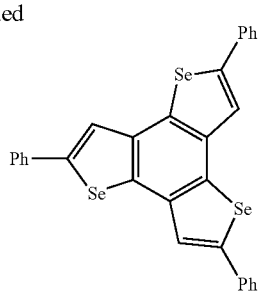

Under a nitrogen atmosphere, selenium (99 mg, 1.25 mmol) and NaBH$_4$ (47.3 mg, 1.25 mmol) were dissolved in ethanol and stirred for 30 minutes whiles maintaining at 5° C. Subsequently, 1,3,5-trichloro-2,4,6-tris(phenylethynyl)benzene (160 mg, 0.33 mmol) obtained in Synthesis Example 5 and NMP (12 mL) were added, heated at 180-190° C. for 20 hours. After completion of the reaction, the reaction mixture was poured in a saturated aqueous ammonium chloride solution (180 mL). A precipitated solid substance was obtained by filtration, washed with water (100 mL), ethanol (100 mL) and acetone (50 mL) and dried under vacuum to obtain a yellow solid substance (164 mg, 81%).

Example 20

Synthesis of 2,5,8-Tris(N-carbazolylamino)benzo[1,2-b:3,4-b':5,6-b"]trithiophene (1021)

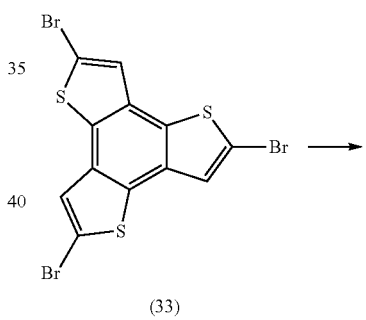

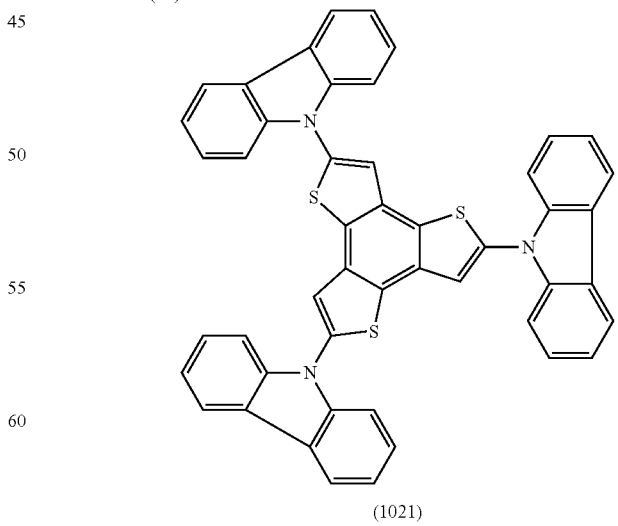

Under a nitrogen atmosphere, 2,5,8-tribromobenzo[1,2-b:3,4-b':5,6-b"]trithiophene (33) (500 mg, 1.04 mmol) obtained in Example 4, carbazole (0.78 g, 4.68 mmol), potassium carbonate (1.29 g, 9.36 mmol) and CuI (29.7 mg, 0.156 mmol) were suspended in nitrobenzene (3.5 mL) and reacted with heating at 210° C. for 3 hours. After completion of the reaction, methanol was added. A precipitated solid substance was obtained by filtration, washed with water and methanol and dried under reduced pressure. The resultant solid substance was subjected to column chromatography (silica gel, dichloromethane) and reprecipitated from dichloromethane and acetonitrile to obtain a solid substance (640 mg), which was further subjected to vacuum sublimation purification to obtain a light yellow substance.

H-NMR (400 MHz, CDCl$_3$) δ7.36 (dd, J=7.2, 7.6 Hz, 6H), 7.50 (dd, J=8.0, 6.0 Hz, 6H), 7.69 (d, J=9.2 Hz, 6H), 7.78 (s, 3H), 8.15 (d, J=J=6.8 Hz, 6H),

MS (EI, 70 eV) m/z=741 (M$^+$); m.p.204.5-206.2° C.

As is apparent from the aforementioned Examples, a heterocyclic compound obtained by the present invention and represented by formula (1) can be said to be an extremely useful compound having characteristic values excellent as an organic thin-film transistor and an organic EL device and high general versatility as an organic electronics device.

REFERENCE SIGNS LIST

The same numerals are used to denote the same names in FIG. 1 to FIG. 3.
- 1 Source electrode
- 2 Semiconductor layer
- 3 Drain electrode
- 4 Insulating layer
- 5 Gate electrode
- 6 Substrate
- 7 Protective layer

The invention claimed is:

1. A heterocyclic compound represented by the following formula (1):

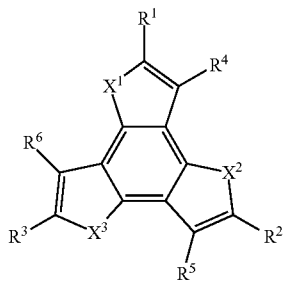

(1)

wherein X$^1$, X$^2$ and X$^3$ each independently represent a sulfur atom or a selenium atom; R$^1$ to R$^6$ each independently represent an aromatic hydrocarbon group selected from the group consisting of a substituted or unsubstituted phenyl group, a substituted or unsubstituted naphthyl group, a substituted or unsubstituted anthryl group, a substituted or unsubstituted phenanthryl group, a substituted or unsubstituted pyrenyl group, a substituted or unsubstituted benzopyrenyl group, a substituted or unsubstituted condensed polycyclic hydrocarbon group, a substituted or unsubstituted heterocyclic hydrocarbon group selected from the group consisting of a substituted or unsubstituted pyridyl group, a substituted or unsubstituted pyrazyl group, a substituted or unsubstituted pyrimidyl group, a substituted or unsubstituted quinolyl group, a substituted or unsubstituted isoquinolyl group, a substituted or unsubstituted pyrrolyl group, a substituted or unsubstituted indolenyl group, a substituted or unsubstituted imidazolyl group, a substituted or unsubstituted carbazolyl group, a substituted or unsubstituted furyl group, a substituted or unsubstituted pyranyl group and a substituted or unsubstituted pyridonyl group, and a condensed heterocyclic hydrocarbon group; an aliphatic hydrocarbon group, a halogen atom, a hydroxyl group, an alkoxyl group, a mercapto group, an alkylthio group, a boronic acid group, a nitro group, a substituted amino group, an amide group, an acyl group, a carboxyl group, an acyloxy group, a cyano group, a sulfo group, a sulfamoyl group, an alkylsulfamoyl group, a carbamoyl group, an alkylcarbamoyl group or a hydrogen atom, provided that they do not simultaneously represent a hydrogen atom.

2. The heterocyclic compound according to claim 1, wherein, in the formula (1), X$^1$, X$^2$ and X$^3$ each are a sulfur atom.

3. The heterocyclic compound according to claim 1 or 2, wherein, in the formula (1), three or more of R$^1$ to R$^6$ each independently represent an aromatic hydrocarbon group, an aliphatic hydrocarbon group, a halogen atom, a hydroxyl group, an alkoxyl group, a mercapto group, an alkylthio group, a boronic acid group, a nitro group, a substituted amino group, an amide group, an acyl group, a carboxyl group, an acyloxy group, a cyano group, a sulfo group, a sulfamoyl group, an alkylsulfamoyl group, a carbamoyl group or an alkylcarbamoyl group, and the remainder are hydrogen atom(s).

4. A process of making a heterocyclic compound according to claim 1, comprising reacting a compound represented by the following formula (1-2) with a sulfur compound or a selenium compound,

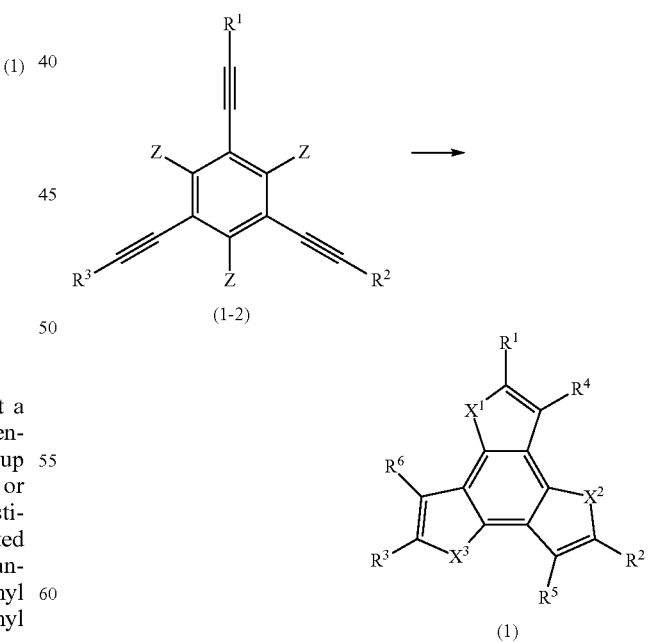

wherein X$^1$, X$^2$ and X$^3$ in formula (1) each independently represent a sulfur atom or a selenium atom; R$^1$ to R$^6$ in formula (1-2) and formula (1) each independently represent an aromatic hydrocarbon group, an aliphatic hydrocarbon group, a halogen atom, a hydroxyl group, an alkoxyl group, a mercapto group, an alkylthio group, a boronic acid group, a nitro group, a substituted amino group, an amide group, an acyl group, a carboxyl group, an acyloxy group, a cyano group, a sulfo group, a sulfamoyl group, an alkylsulfamoyl group, a carbamoyl group, an alkylcarbamoyl group or a hydrogen atom, provided that they do not simultaneously represent a hydrogen atom, and Z in formula (1-2) represents a halogen atom.

5. The heterocyclic compound according to claim 1, wherein, in formula (1), at least one of $R^1$ to $R^6$ is said aromatic hydrocarbon group.

6. A heterocyclic compound represented by the following formula (1):

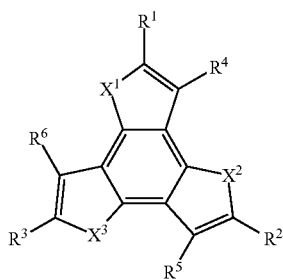

(1)

wherein $X^1$, $X^2$ and $X^3$ each independently represent a sulfur atom or a selenium atom; $R^1$ to $R^6$ each independently represent an aromatic hydrocarbon group, an aliphatic hydrocarbon group, a halogen atom, a hydroxyl group, an alkoxyl group, a mercapto group, an alkylthio group, a boronic acid group, a nitro group, a substituted amino group, an amide group, an acyl group, a carboxyl group, an acyloxy group, a cyano group, a sulfo group, a sulfamoyl group, an alkylsulfamoyl group, a carbamoyl group, an alkylcarbamoyl group or a hydrogen atom, provided that they do not simultaneously represent a hydrogen atom, and wherein at least one of $R^1$ to $R^6$ is an aromatic hydrocarbon group, and the aromatic hydrocarbon group has an amino group.

7. A heterocyclic compound represented by the following formula (1):

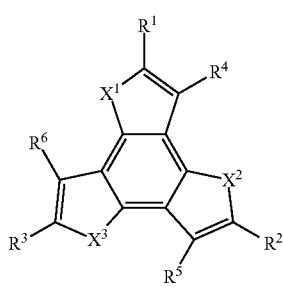

(1)

wherein $X^1$, $X^2$ and $X^3$ each independently represent a sulfur atom or a selenium atom; $R^1$ to $R^6$ each independently represent an aromatic hydrocarbon group, an aliphatic hydrocarbon group, a halogen atom, a hydroxyl group, an alkoxyl group, a mercapto group, an alkylthio group, a boronic acid group, a nitro group, a substituted amino group, an amide group, an acyl group, a carboxyl group, an acyloxy group, a cyano group, a sulfo group, a sulfamoyl group, an alkylsulfamoyl group, a carbamoyl group, an alkylcarbamoyl group or a hydrogen atom, provided that they do not simultaneously represent a hydrogen atom, and wherein, at least one of $R^1$ to $R^6$ is an aromatic hydrocarbon group, and in formula (1), $R^1$, $R^3$ and $R^5$ each are an aromatic hydrocarbon group and $R^2$, $R^4$ and $R^6$ each are a hydrogen atom.

8. A heterocyclic compound represented by the following formula (1):

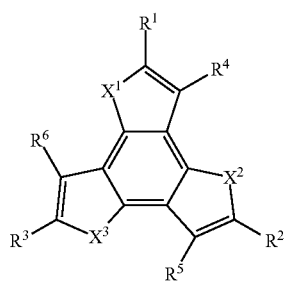

(1)

wherein $X^1$, $X^2$ and $X^3$ each independently represent a sulfur atom or a selenium atom; $R^1$ to $R^6$ each independently represent an aromatic hydrocarbon group, an aliphatic hydrocarbon group, a halogen atom, a hydroxyl group, an alkoxyl group, a mercapto group, an alkylthio group, a boronic acid group, a nitro group, a substituted amino group, an amide group, an acyl group, a carboxyl group, an acyloxy group, a cyano group, a sulfo group, a sulfamoyl group, an alkylsulfamoyl group, a carbamoyl group, an alkylcarbamoyl group or a hydrogen atom, provided that they do not simultaneously represent a hydrogen atom, and wherein, in formula (1), at least one of $R^1$ to $R^6$ is an aliphatic hydrocarbon group.

9. The heterocyclic compound according to claim 8, wherein, in formula (1), $R^1$, $R^3$ and $R^5$ each are an aliphatic hydrocarbon group and $R^2$, $R^4$ and $R^6$ each are a hydrogen atom.

10. The heterocyclic compound according to claim 8, wherein the aliphatic hydrocarbon group is a linear or branched alkyl group.

11. A heterocyclic compound represented by the following formula (1):

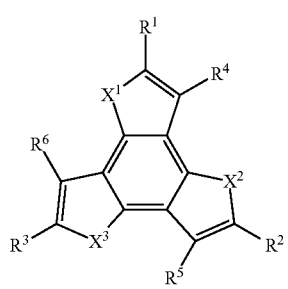

(1)

wherein $X^1$, $X^2$ and $X^3$ each independently represent a sulfur atom or a selenium atom; $R^1$ to $R^6$ each independently represent an aromatic hydrocarbon group, an aliphatic hydrocarbon group, a halogen atom, a hydroxyl group, an alkoxyl group, a mercapto group, an alkylthio group, a boronic acid group, a nitro group, a substituted amino group, an amide group, an acyl group, a carboxyl group, an acyloxy group, a cyano group, a sulfo group, a sulfamoyl group, an alkylsulfamoyl group, a carbamoyl group, an alkylcarbamoyl group or a hydrogen atom, provided that they do not simultaneously represent a hydrogen atom, and wherein, in formula (1), at least one of $R^1$ to $R^6$ is a halogen atom.

12. The heterocyclic compound according to claim 11, wherein, in formula (1), $R^1$ to $R^6$ each are a halogen atom.

13. The heterocyclic compound according to claim 11, wherein, in formula (1), $R^1$, $R^3$ and $R^5$ each are a halogen atom and $R^2$, $R^4$ and $R^6$ each are a hydrogen atom.

14. The heterocyclic compound according to claim 11, wherein, the halogen atom is a bromine atom.

15. A heterocyclic compound represented by the following formula (1):

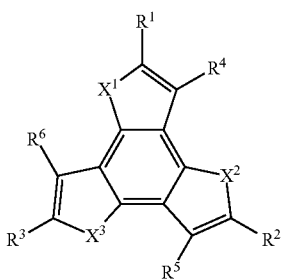

(1)

wherein $X^1$, $X^2$ and $X^3$ each independently represent a sulfur atom or a selenium atom; $R^1$ to $R^6$ each independently represent an aromatic hydrocarbon group, an aliphatic hydrocarbon group, a halogen atom, a hydroxyl group, an alkoxyl group, a mercapto group, an alkylthio group, a boronic acid group, a nitro group, a substituted amino group, an amide group, an acyl group, a carboxyl group, an acyloxy group, a cyano group, a sulfo group, a sulfamoyl group, an alkylsulfamoyl group, a carbamoyl group, an alkylcarbamoyl group, an aldehyde group, or a hydrogen atom, provided that they do not simultaneously represent a hydrogen atom, and wherein, in formula (1), at least one of $R^1$ to $R^6$ is said aldehyde group.

16. A composition containing the heterocyclic compound according to claim 1, further containing a solvent, a binder, or both a solvent and a binder.

17. A thin film formed of the heterocyclic compound according to claim 1.

18. An organic semiconductor material containing the heterocyclic compound according to claim 1.

19. A liquid crystal material containing the heterocyclic compound according to claim 1.

20. An organic electronics device comprising the heterocyclic compound according to claim 1.

21. The organic electronics device according to claim 20, wherein the device is a photoelectric conversion device, an organic solar battery device, an organic EL device, an organic semiconductor laser device, a liquid crystal display device or a thin-film transistor device.

22. An organic EL device or a thin-film transistor device comprising the organic semiconductor material according to claim 18.

23. An organic EL display apparatus composed of the organic EL device according to claim 22.

24. A liquid crystal display device comprising the liquid crystal material according to claim 19.

25. A liquid crystal display apparatus having the liquid crystal display device according to claim 24 installed therein.

26. A thin film formed of the composition according to claim 16.

27. An organic semiconductor material containing the composition according to claim 16.

28. A liquid crystal material containing the composition according to claim 16.

29. An organic electronics device comprising the composition according to claim 16.

30. An organic electronics device comprising the liquid crystal material according to claim 19.

31. The organic electronics device according to claim 29, wherein the device is a photoelectric conversion device, an organic solar battery device, an organic EL device, an organic semiconductor laser device, a liquid crystal display device or a thin-filmed transistor device.

32. An organic EL device or a thin-filmed transistor device comprising the organic semiconductor material according to claim 27.

33. An organic EL display apparatus composed of the organic EL device according to claim 32.

34. A liquid crystal display device comprising the liquid crystal material according to claim 28.

35. A liquid crystal display apparatus having the liquid crystal display device according to claim 34 installed therein.

36. The organic electronics device according to claim 30, wherein the device is a photoelectric conversion device, an organic solar battery device, an organic EL device, an organic semiconductor laser device, a liquid crystal display device or a thin-film transistor device.

\* \* \* \* \*